United States Patent
Bar-Ziv et al.

(10) Patent No.: US 11,396,012 B2
(45) Date of Patent: Jul. 26, 2022

(54) MICROFLUIDIC DEVICE FOR ANALYZING GENE EXPRESSION

(71) Applicant: Yeda Research and Development Co. Ltd., Rehovot (IL)

(72) Inventors: Roy Bar-Ziv, Rehovot (IL); Eyal Karzbrun, Rehovot (IL); Alexandra Tayar, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 15/027,471

(22) PCT Filed: Oct. 7, 2014

(86) PCT No.: PCT/IL2014/050889
§ 371 (c)(1),
(2) Date: Apr. 6, 2016

(87) PCT Pub. No.: WO2015/052717
PCT Pub. Date: Apr. 16, 2015

(65) Prior Publication Data
US 2016/0243547 A1 Aug. 25, 2016

Related U.S. Application Data

(60) Provisional application No. 61/887,457, filed on Oct. 7, 2013.

(51) Int. Cl.
| | |
|---|---|
| *C12Q 1/68* | (2018.01) |
| *B01L 3/00* | (2006.01) |
| *C12P 21/02* | (2006.01) |
| *B05D 1/40* | (2006.01) |
| *B01J 19/00* | (2006.01) |

(52) U.S. Cl.
CPC ..... *B01L 3/502715* (2013.01); *B01J 19/0093* (2013.01); *B01L 3/502707* (2013.01); *B01L 3/502738* (2013.01); *B01L 3/502746* (2013.01); *C12P 21/02* (2013.01); *B01L 2200/0694* (2013.01); *B01L 2200/10* (2013.01); *B01L 2200/12* (2013.01); *B01L 2300/0636* (2013.01); *B01L 2300/0816* (2013.01); *B01L 2300/0864* (2013.01); *B01L 2400/0472* (2013.01); *B01L 2400/0487* (2013.01); *B01L 2400/06* (2013.01); *C12Q 2565/629* (2013.01)

(58) Field of Classification Search
None
See application file for complete search history.

(56) References Cited

U.S. PATENT DOCUMENTS

| | | | |
|---|---|---|---|
| 8,449,837 B2 | 5/2013 | Levchenko et al. | |
| 8,592,221 B2 | 11/2013 | Fraden et al. | |
| 2005/0277125 A1* | 12/2005 | Benn | B01J 19/0046 435/6.11 |
| 2009/0142236 A1 | 6/2009 | Unger et al. | |
| 2009/0156423 A1* | 6/2009 | Stahler | B01J 19/0046 506/9 |
| 2009/0197274 A1 | 8/2009 | Takagi | |
| 2010/0112569 A1 | 5/2010 | Bar-Zvi et al. | |
| 2014/0256047 A1* | 9/2014 | Lee | C12N 15/87 435/461 |

FOREIGN PATENT DOCUMENTS

| | | |
|---|---|---|
| WO | WO 2008/090557 | 7/2008 |
| WO | WO 2015/052717 | 4/2015 |

OTHER PUBLICATIONS

Miyake et al, Transfection microarrayt and the applications, Mol. BioSyst., 2009, 5, 444-449.*
Sobek et al, Microarray Technology as a Universal Tool for High-Throughput Analysis of Biological SystemsCombinatorial Chemistry & High Throughput Screening, 2006, 9, 365-380.*
Wu M, Yuan F (2011) Membrane Binding of Plasmid DNA and Endocytic Pathways Are Involved in Electrotransfection of Mammalian Cells. PLoS ONE 2011, pp. 1-9.*
Karzbrun et al. "Programmable On-Chip DNA Compartments as Artificial Cells", Science, 345(6198): 829-832, Aug. 15, 2014.
Mei et al. "Cell-Free Protein Synthesis in Microfluidic Array Devices", Biotechnology Progress, 23(6): 1305-1311, Sep. 5, 2008.
Osaki et al. "Lipid-Coated Microdroplet Array for In Vitro Protein Synthesis", Analytical Chemistry, 83(8): 3186-3191, Mar. 18, 2007.
Buxboim et al. "A Single-Step Photolithographic Interface for Cell-Free Gene Expression and Active Biochips", Small, XP002618809, 3(3): 500-510, Mar. 5, 2007.

* cited by examiner

*Primary Examiner* — Maria Marvich

(57) ABSTRACT

A microfluidic device is disclosed which comprises:
(i) at least one reaction unit having a test chamber connected to at least one microchannel, wherein a surface of at least a portion of said reaction unit is attached to an isolated nucleic acid; and
(ii) a flow-through channel having at least one inlet port and at least one outlet port, said flow-through channel and said microchannel being of dimensions to allow reactant diffusion to and from said reaction unit, wherein the diffusion time of said reactant along the microchannel is shorter than the flow time along the microchannel.

25 Claims, 28 Drawing Sheets
(24 of 28 Drawing Sheet(s) Filed in Color)
Specification includes a Sequence Listing.

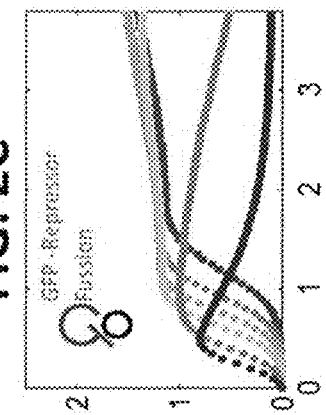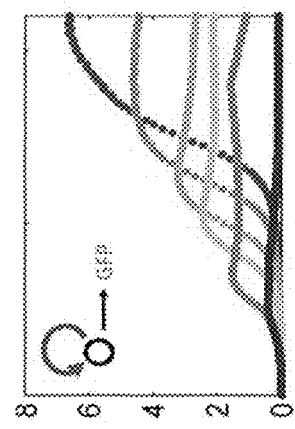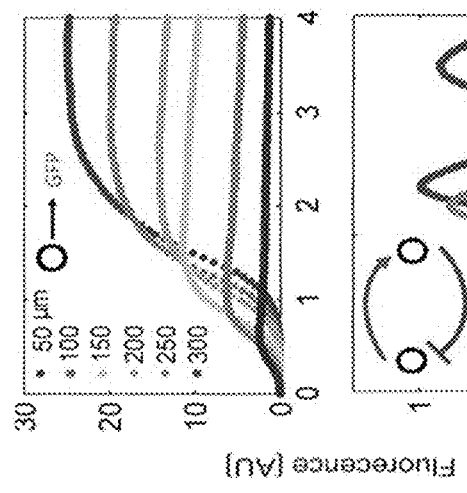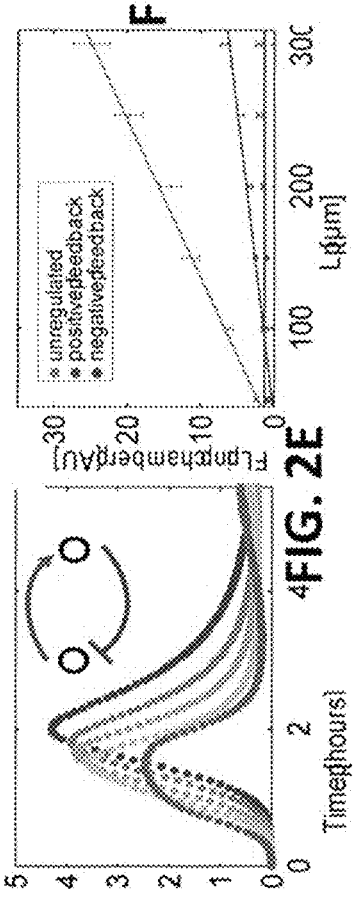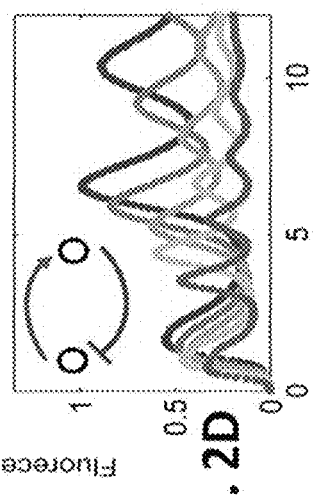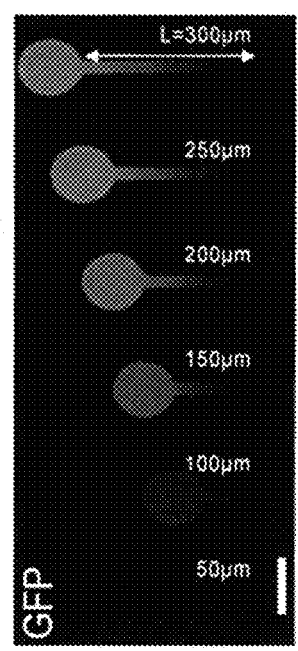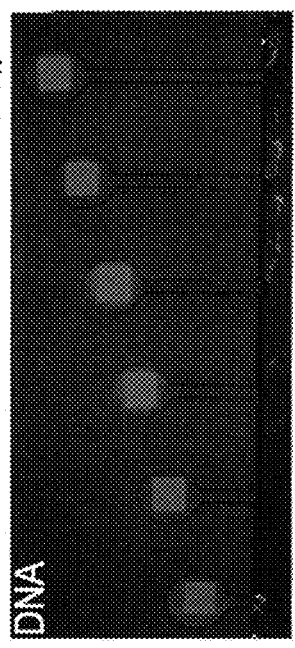

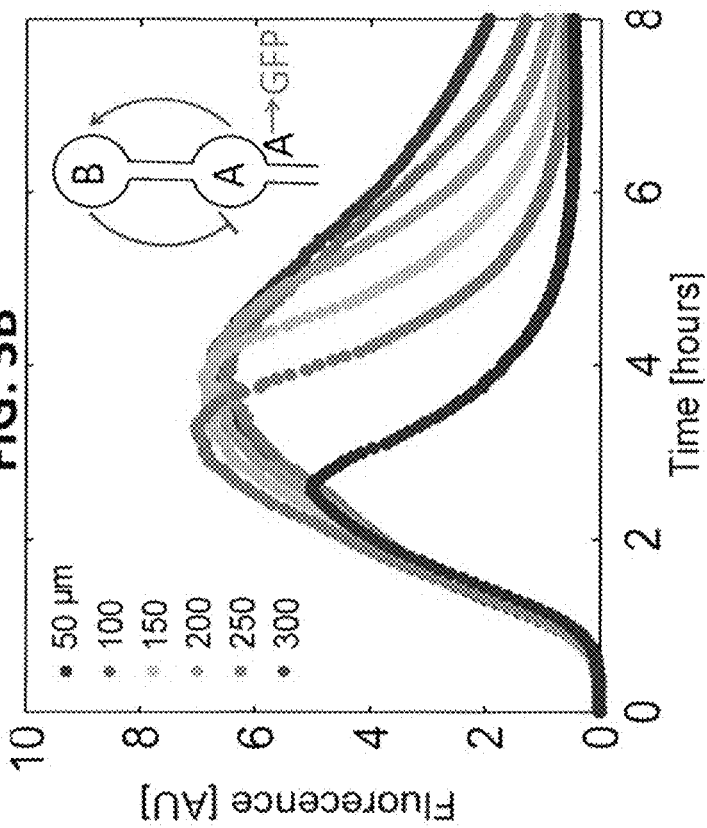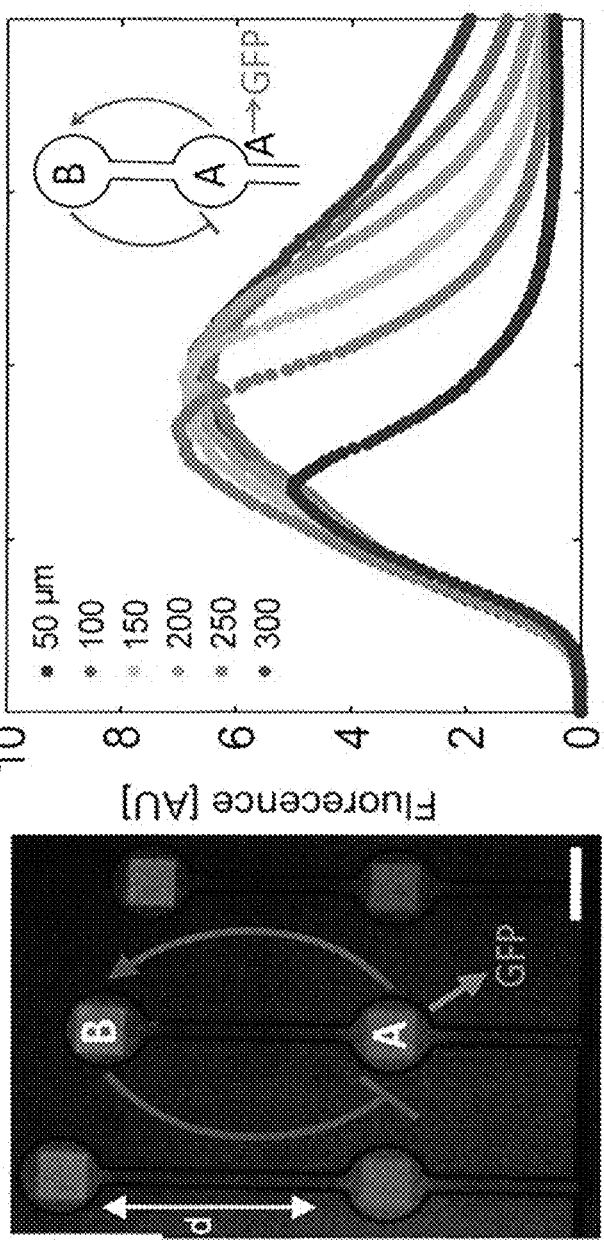
FIG. 3A
FIG. 3B

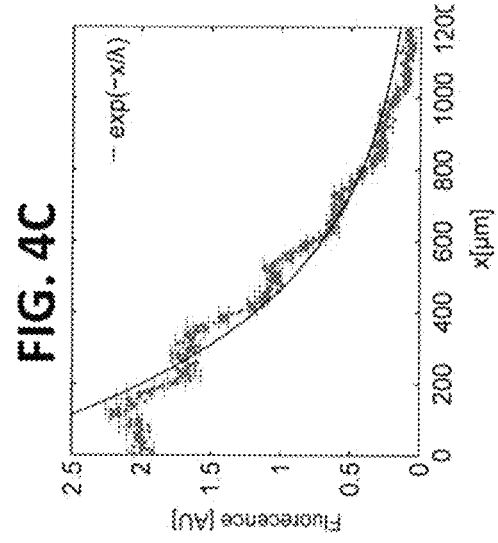
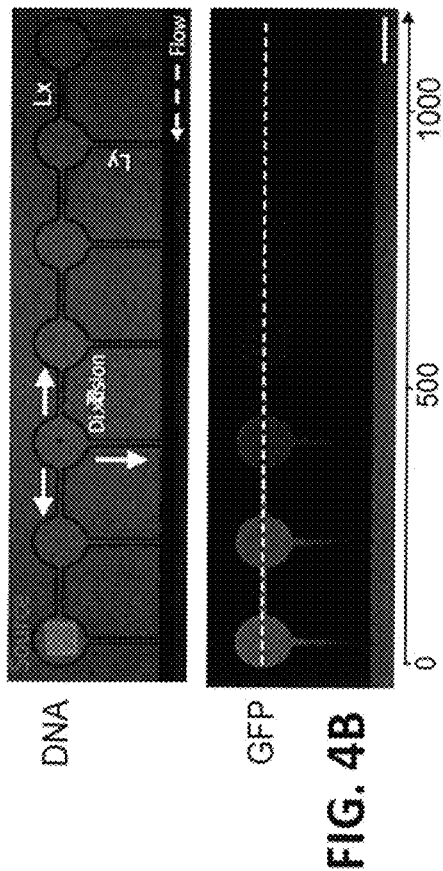
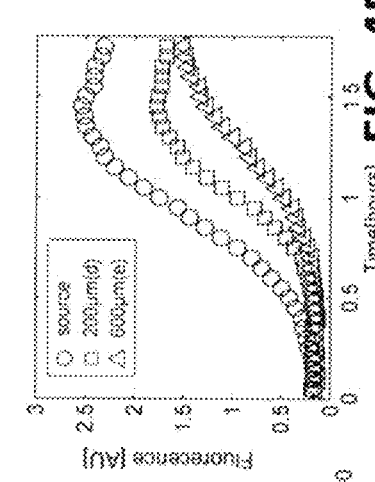
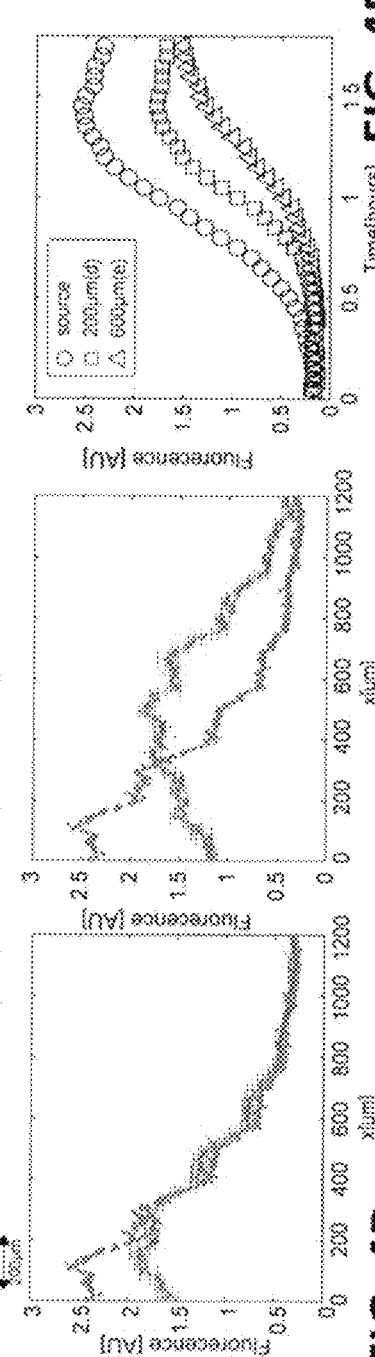
FIG. 4A
FIG. 4B
FIG. 4C
FIG. 4D
FIG. 4E
FIG. 4F

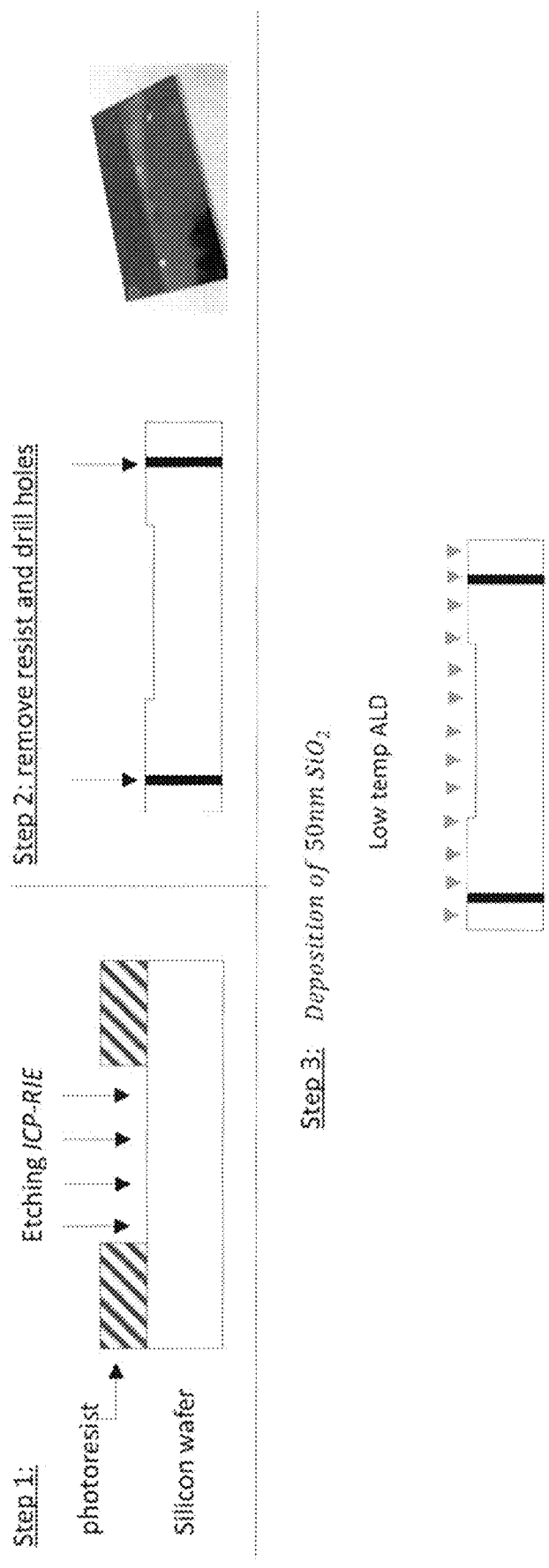

Step 4: Coating with a photoactivble monolayer

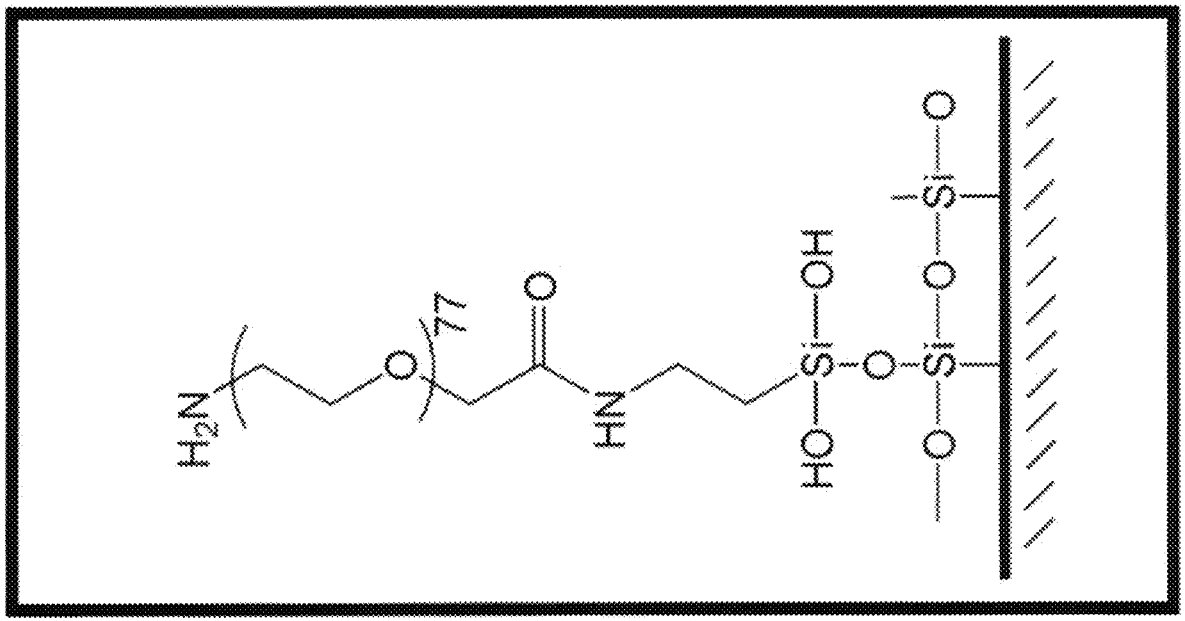
FIG. 6A Continued
Step 5: Lythography patterning
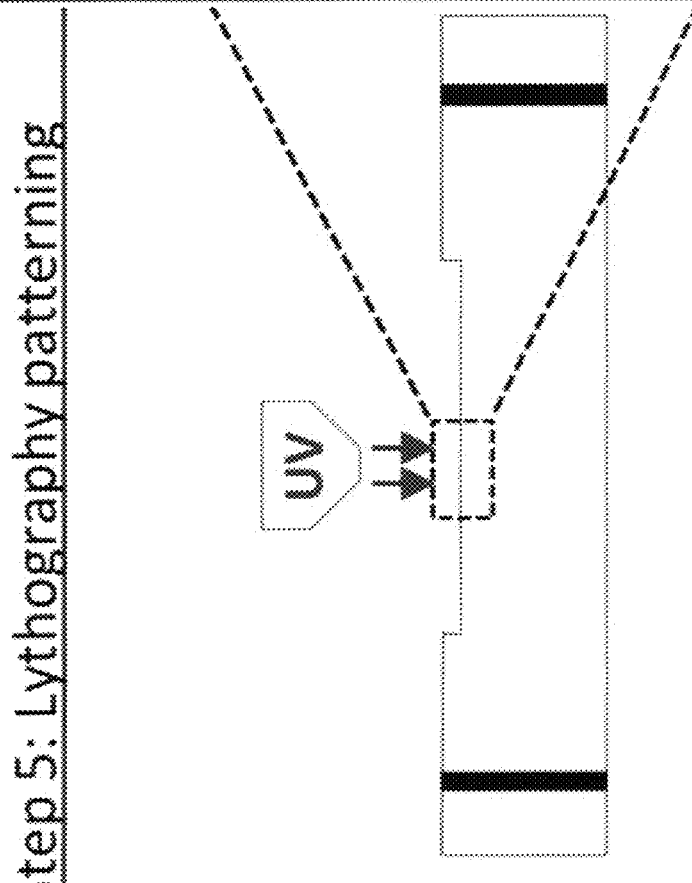

Step 6: Biotin-NHS conjugation

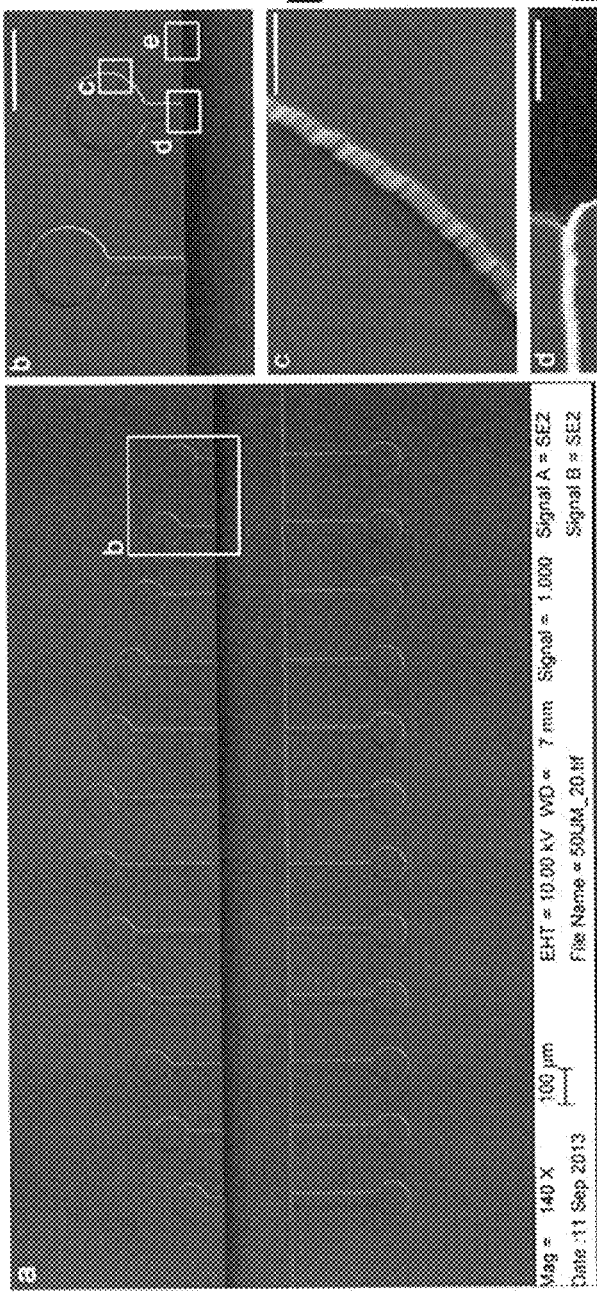
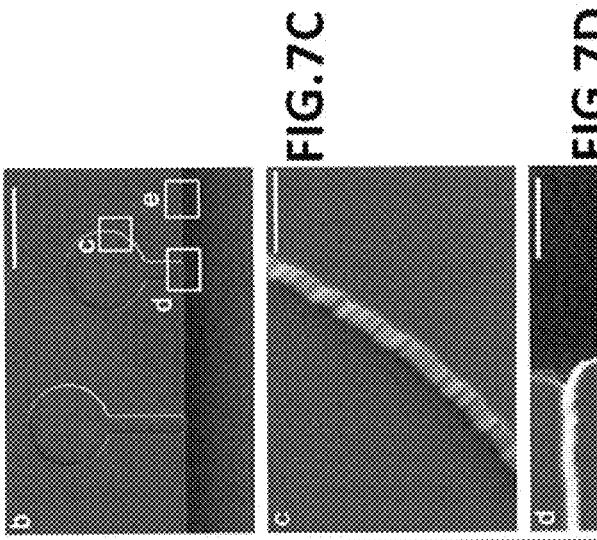
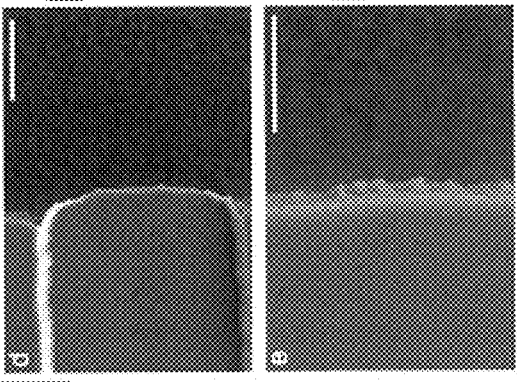
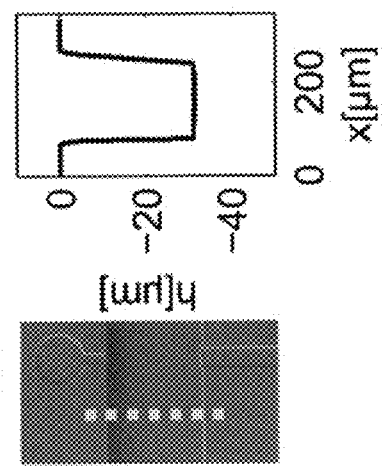
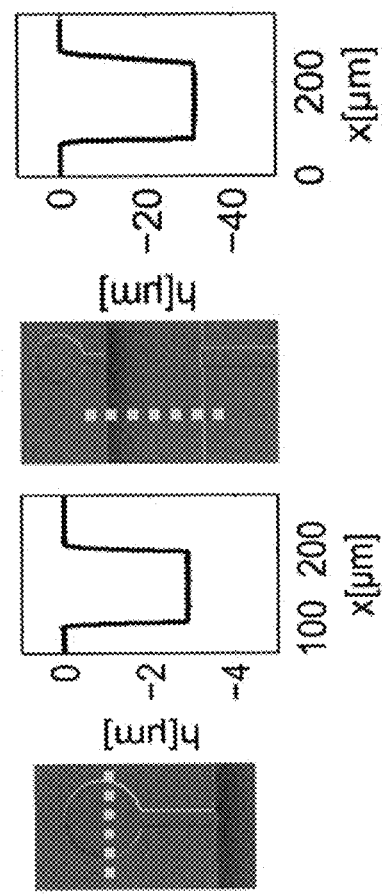
FIG. 7A FIG. 7B FIG. 7C FIG. 7D FIG. 7E FIG. 7F FIG. 7G

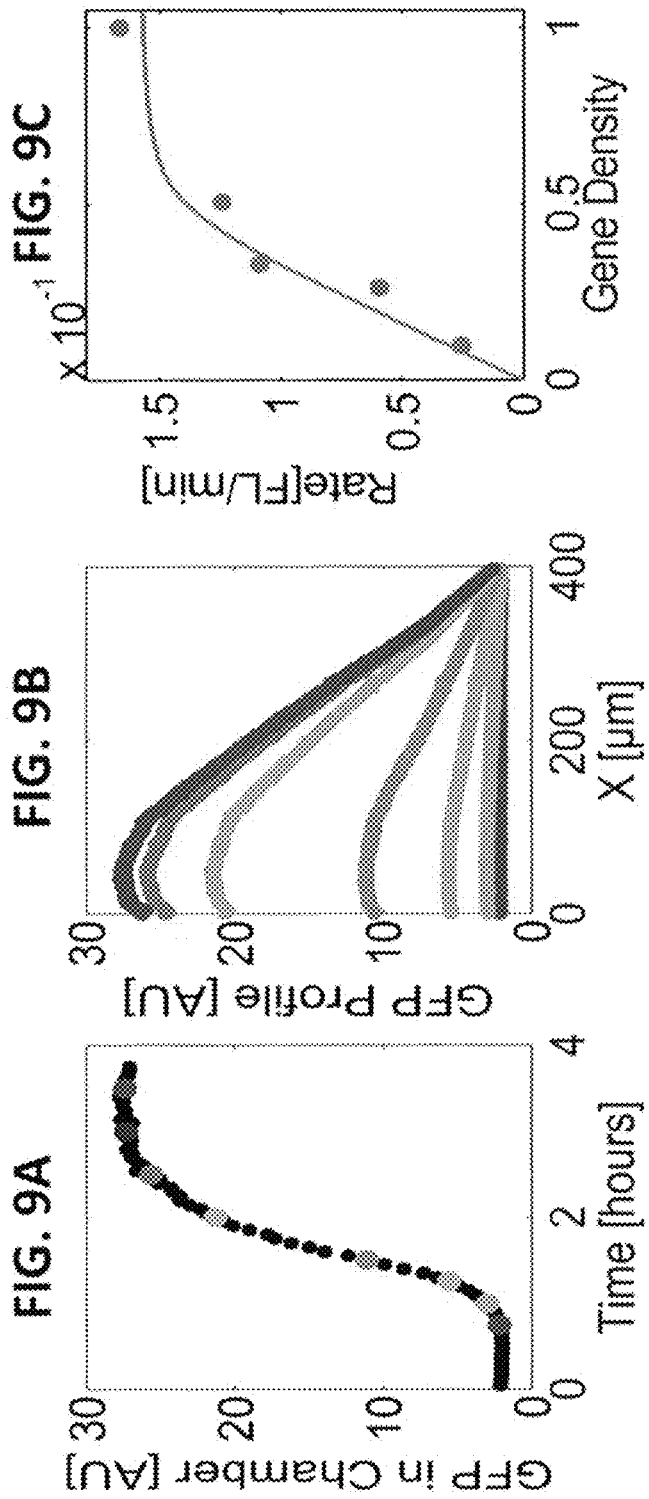

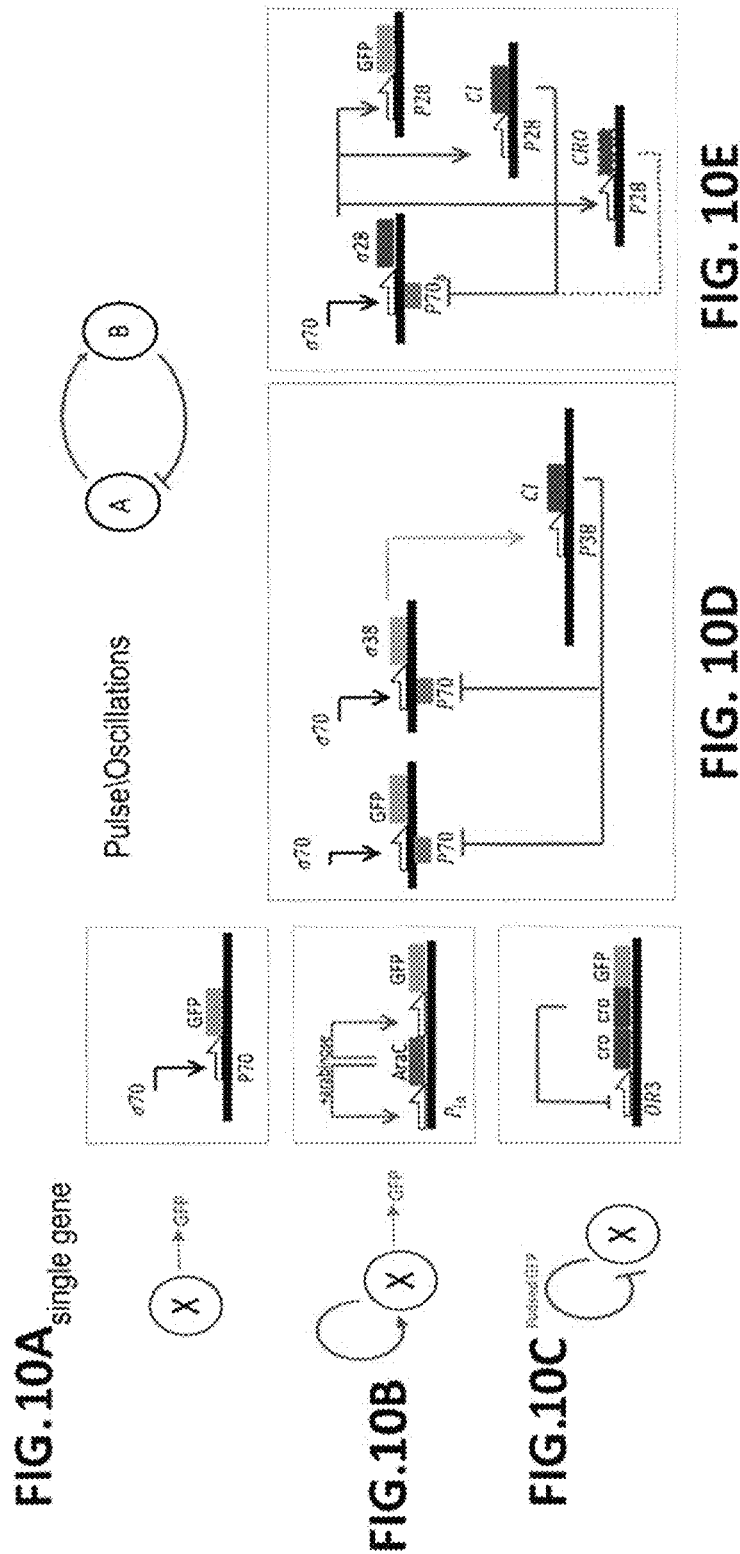

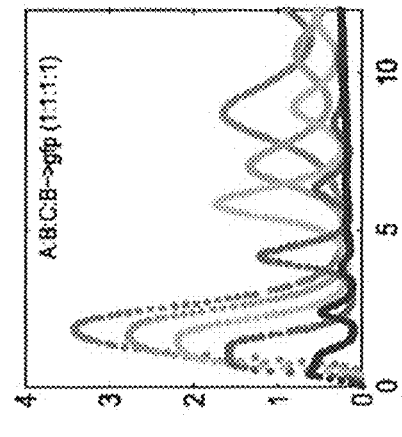
FIG. 15D
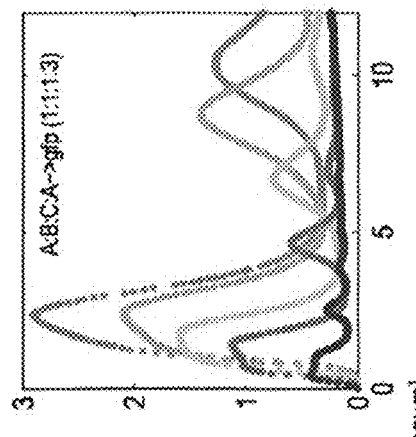
FIG. 15F
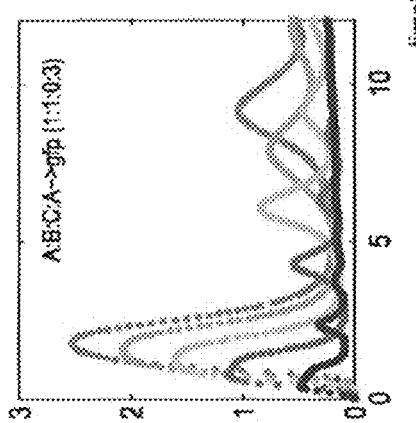
FIG. 15C
FIG. 15E
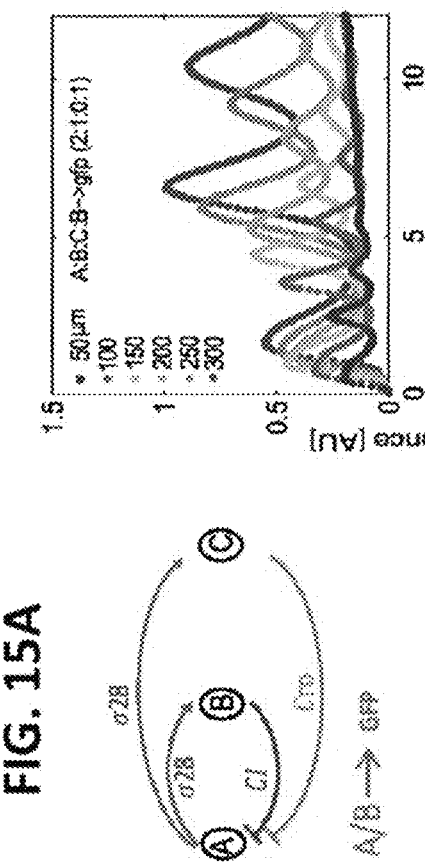
FIG. 15A
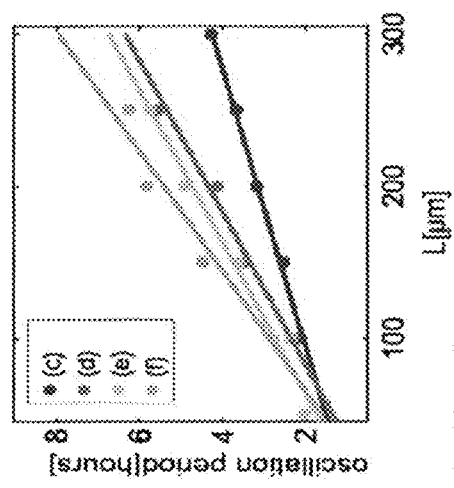
FIG. 15B

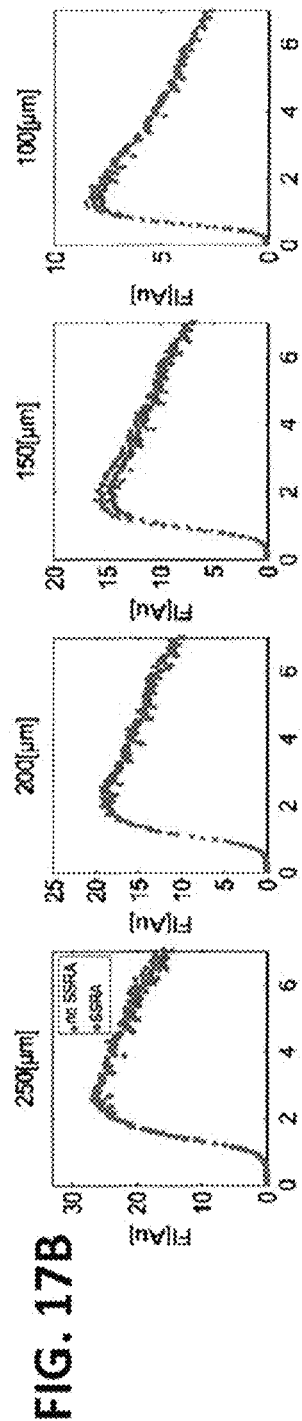
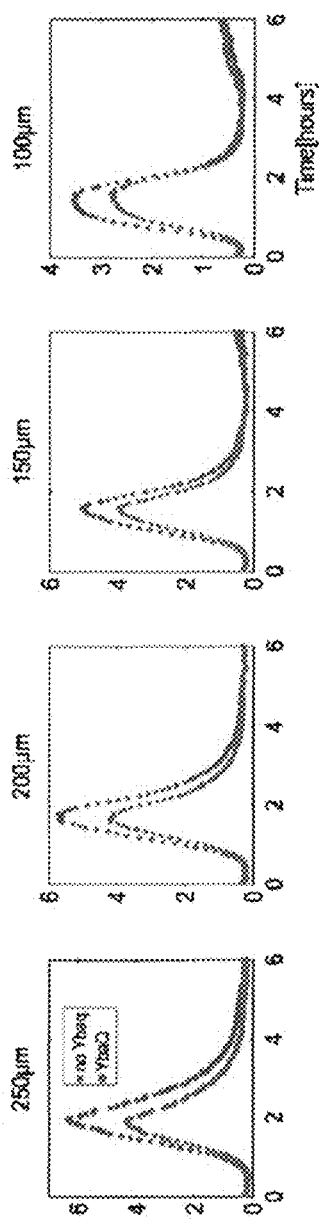
FIG. 17A
FIG. 17B
FIG. 17C
FIG. 17D

MICROFLUIDIC DEVICE FOR ANALYZING GENE EXPRESSION

RELATED APPLICATIONS

This application is a National Phase of PCT Patent Application No. PCT/IL2014/050889 having International filing date of Oct. 7, 2014, which claims the benefit of priority under 35 USC § 119(e) of U.S. Provisional Patent Application No. 61/887,457 filed on Oct. 7, 2013. The contents of the above applications are all incorporated by reference as if fully set forth herein in their entirety.

SEQUENCE LISTING STATEMENT

The ASCII file, entitled 65738SequenceListing.txt, created on Apr. 6, 2016, comprising 55,442 bytes, submitted concurrently with the filing of this application is incorporated herein by reference.

FIELD AND BACKGROUND OF THE INVENTION

The present invention, in some embodiments thereof, relates to a microfluidic device for analyzing cell-free gene expression.

Recently, there have been concerted efforts to develop and manufacture microfluidic systems to perform various chemical and biochemical analyses and syntheses, both for preparative and analytical applications. The goal to make such devices arises because of the significant benefits that can be realized from miniaturization with respect to analyses and syntheses conducted on a macro scale. Such benefits include a substantial reduction in time, cost and the space requirements for the devices utilized to conduct the analysis or synthesis.

Additionally, microfluidic devices have the potential to be adapted for use with automated systems, thereby providing the additional benefits of further cost reductions and decreased operator errors because of the reduction in human involvement.

One class of systems includes microfluidic "chips" that include very small fluid channels and small reaction/analysis chambers. These systems can be used for analyzing very small amounts of samples and reagents and can control liquid and gas samples on a small scale. Microfluidic chips have found use in both research and production, and are currently used for applications such as genetic analysis, chemical diagnostics, drug screening, and environmental monitoring. Although these systems may allow manipulation of small volumes of fluids, additional methods that allow further control and flexibility are needed.

Background art includes U.S. Pat. Nos. 8,592,221, 8,449,837 and International Patent Application WO2008/090557.

SUMMARY OF THE INVENTION

According to an aspect of some embodiments of the present invention there is provided a microfluidic device comprising:

(i) at least one reaction unit having a test chamber connected to at least one microchannel, wherein a surface of at least a portion of said reaction unit is attached to an isolated nucleic acid; and (ii) a flow-through channel having at least one inlet port and at least one outlet port, said flow-through channel and said microchannel being of dimensions to allow reactant diffusion to and from said reaction unit, wherein the diffusion time of said reactant along the microchannel is shorter than the flow time along the microchannel.

According to an aspect of some embodiments of the present invention there is provided a method of expressing a polypeptide comprising contacting the isolated nucleic acid of the microfluidic device described herein with a composition which comprises enzymes for performing expression of the polypeptide from said isolated nucleic acid, under conditions that allow expression of the polypeptide, thereby expressing the polypeptide.

According to some embodiments of the invention, the depth ratio of said reaction unit:flow-through channel is greater than 1:5.

According to some embodiments of the invention, the ratio of hydrodynamic resistance between the microchannel and the flow-channel is about $10^5$-$10^6$.

According to some embodiments of the invention, the width ratio of said microchannel:flow-through channel is greater than 1:5.

According to some embodiments of the invention, the fluid flow resistance is higher in the reaction unit than in the flow-through channel.

According to some embodiments of the invention, the depth of the reaction unit is about 1 micron to about 20 microns.

According to some embodiments of the invention, the depth of the flow-through channels is about 25 microns to about 150 microns.

According to some embodiments of the invention, the device further comprises at least one valve to control flow of fluid through said flow-through channel.

According to some embodiments of the invention, the device comprises at least two reaction units.

According to some embodiments of the invention, the length of the microchannel of the first reaction unit is identical to the length of the microchannel of the second reaction unit.

According to some embodiments of the invention, the length of the microchannel of the first reaction unit is non-identical to the length of the microchannel of the second reaction unit.

According to some embodiments of the invention, the test chamber is 10-200 microns in diameter.

According to some embodiments of the invention, the device further comprises at least one external reservoir being in fluid communication with said inlet port.

According to some embodiments of the invention, a sequence of said nucleic acid encodes a promoter operatively linked to a nucleic acid sequence encoding a polypeptide.

According to some embodiments of the invention, the polypeptide is a detectable polypeptide.

According to some embodiments of the invention, the promoter is a tissue-specific promoter.

According to some embodiments of the invention, the polypeptide is a transcription factor.

According to some embodiments of the invention, the device is of dimensions such that the polypeptide expressed from said nucleic acid forms a gradient in said reaction chamber.

According to some embodiments of the invention, a test chamber of a first of said two reaction units is connected to a test chamber of a second of said two reaction units via a microchannel.

According to some embodiments of the invention, the reaction unit has two test chambers connected to said microchannel.

According to some embodiments of the invention, the sequence of the isolated nucleic acid in a first of said two test chambers is different to the sequence of the isolated nucleic acid in a second of said two test chambers.

According to some embodiments of the invention, the promoter is a constitutive promoter.

According to some embodiments of the invention, the promoter is a non-constitutive promoter.

According to some embodiments of the invention, the nucleic acid is attached to said surface via a reactive group.

According to some embodiments of the invention, the reactive group is photoreactivatable.

According to some embodiments of the invention, the photoreactivatable reactive group is selected from the group consisting of amine, hydroxy, thiohydroxy, halo, alkoxy, thioalkoxy, aryloxy, thioaryloxy, carboxylate, phosphate, phosphonate, sulfate and sulfonate.

According to some embodiments of the invention, the nucleic acid sequence comprises a plurality of nucleic acid sequences.

According to some embodiments of the invention, the plurality of nucleic acid sequences encode a transcriptome.

According to some embodiments of the invention, the nucleic acid comprises bacterial sequences.

According to some embodiments of the invention, the nucleic acid comprises eukaryotic sequences.

According to some embodiments of the invention, the device is fabricated from a substrate having attached thereto a plurality of monolayers said monolayers being composed of a compound which comprises a general formula I:

$$X\text{-}L\text{-}Y \qquad \text{Formula I}$$

wherein:

X is a functionalized group capable of binding to said substrate;

L is a polymer capable of forming said monolayer onto said substrate; and

Y is a photoactivatable group capable of generating a reactive group upon exposure to said light.

According to some embodiments of the invention, the composition comprises a cell extract.

According to some embodiments of the invention, the cell extract is devoid of nucleic acids.

According to some embodiments of the invention, the protein forms a gradient in the reaction unit.

According to some embodiments of the invention, the expressing is effected for at least 6 hours.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

General Terminology

As used herein, the term "amine" describes both a —NR'R" group and a —NR'— group, wherein R' and R" are each independently hydrogen, alkyl, cycloalkyl, aryl, as these terms are defined herein.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, connecting another moiety at each end thereof.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The alkyl group can be an end group, as this term is defined hereinabove, wherein it is attached to a single adjacent atom, or a linking group, as this term is defined hereinabove, connecting two or more moieties at two or more positions thereof.

The term "halide" or "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, or an —O—S(=O)$_2$—O— linking group, as these phrases are defined hereinabove, where R' is as defined hereinabove. This term further encompasses thiosulfates.

The term "thiosulfate" describes a —O—S(=S)(=O)—OR' end group or a —O—S(=S)(=O)—O— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "sulfonamide" describes a —S(=O)$_2$—NR'R" end group or a —S(=O)$_2$—NR'— linking group, as these phrases are defined hereinabove, with R' and R" as defined herein. This term encompasses the terms N-sulfonamide and S-sulfonamide.

The term "N-sulfonamide" describes an R'S(=O)$_2$—NR"— end group or a —S(=O)$_2$—NR'— linking group, as these phrases are defined hereinabove, where R' and R" are as defined herein.

The term "S-sulfonamide" describes an —S(=O)$_2$—NR'R"— end group or a —S(=O)$_2$—NR'— linking group, as these phrases are defined hereinabove, where R' and R" are as defined herein.

The term "phosphonate" describes a —P(=O)(OR')(OR") end group or a —P(=O)(OR')(O)— linking group, as these phrases are defined hereinabove, with R' and R" as defined herein.

The term "phosphate" describes an —O—P(=O)$_2$(OR') end group or a —O—P(=O)$_2$(O)— linking group, as these phrases are defined hereinabove, with R' as defined herein. This term further encompasses the term thiophosphonate.

The term "thiophosphate" describes an —O—P(=O)(=S)(OR') end group or a —O—P(=O)(=S)(O)— linking group, as these phrases are defined hereinabove, with R' as defined herein.

The term "carbonyl" or "carbonylate" as used herein, describes a —C(=O)—R' end group or a —C(=O)— linking group, as these phrases are defined hereinabove, with R' as defined herein. Alternatively, R' can be halide, or any other reactive derivative. This term encompasses the term "thiocarbonyl".

The term "thiocarbonyl" as used herein, describes a —C(=S)—R' end group or a —C(=S)— linking group, as these phrases are defined hereinabove, with R' as defined herein.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "azo" describes an —N=NR' end group or an —N=N-linking group, as these phrases are defined hereinabove, with R' as defined hereinabove.

The term "carboxylate" describes a —C(=O)—OR' end group or a —C(=O)—O— linking group, as these phrases are defined hereinabove, where R' is as defined herein. This term encompasses the terms O-carboxylate, C-thiocarboxylate, and O-thiocarboxylate, as well as various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters.

The term "carbamate" describes an R"OC(=O)—NR'— end group or a —OC(=O)—NR'— linking group, as these phrases are defined hereinabove, with R' and R" as defined herein. This term encompasses the terms O-carbamate, thiocarbamate and include various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters.

The term "amide" describes a —C(=O)—NR'R" end group or a —C(=O)—NR'— linking group, as these phrases are defined hereinabove, where R' and R" are as defined herein. This term encompasses the term N-amide.

The term "N-amide" describes a R'C(=O)—NR"— end group or a R'C(=O)—N— linking group, as these phrases are defined hereinabove, where R' and R" are as defined herein.

The term "hydrazine" describes a —NR'—NR"R"' end group or a —NR'—NR"— linking group, as these phrases are defined hereinabove, with R', R", and R"' as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "ester" describes a moiety containing a carboxylate group, as defined herein.

An "alkenyl" group describes an alkyl group which consists of at least two carbon atoms and at least one carbon-carbon double bond.

An "alkynyl" group describes an alkyl group which consists of at least two carbon atoms and at least one carbon-carbon triple bond.

A "dienophile" group describes a group which comprises at least two conjugated double-double boned.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F. 2D DNA compartments and emergent gene network dynamics. (A) DNA brushes patterned (red squares) in circular compartments (h≈2 μm) carved in silicon and connected through a diffusive capillary to a channel flowing a cell-free protein expression reaction. (B) Overlay of expressed GFP in the compartment and end-labeled DNA brush images. (C) GFP intensity profile in arbitrary units (AU) of an unregulated construct along the capillary after 4 hours of expression. (D) Steady-state dynamics of an auto-regulatory construct reported by GFP. (E) Emergent oscillation of an activator-repressor network. (F) Repressor-GFP fusion binding its own promoter during expression of a self-repressed DNA construct. Scale bar is 100 μm. GFP intensity was taken from single reactors and averaged over the compartment area with error bars the size of data points.

FIGS. 2A-H. Gene network dynamics regulated by geometry. (A-E) Expression dynamics of GFP in the DNA compartment with varying capillary length L=50-300 μm as denoted, and for five different constructs: (A) unregulated, (B) positive feedback, (C) negative feedback, (D) activator-repressor network with activator $\sigma^{28}$ and repressor cI and (E) activator-repressor network with activator $\sigma^{38}$ and repressor cI. (F) Maximal GFP intensity as a function of the capillary length for the different constructs (A-C). Error bars represent standard variation over 3 repeats. (G) Fluorescence image of DNA brushes before expression, and (H) GFP expression of the unregulated construct after 3 hours. Scale bar 100 μm.

FIGS. 3A-B. Communication between DNA compartments. (A) Fluorescent image of DNA brush overlaid with the activator (denoted A)–repressor (denoted B) network scheme. The distance between compartments A and B varied d=50-300 μm. Scale bar: 100 μm. (B) GFP expression kinetics at compartment A for different distances between compartments, as denoted.

FIGS. 4A-F. Protein gradients in one-dimensional arrays. (A) DNA brush patterned in an array of seven connected compartments. (B) Image of GFP gradient after 3 hours of expression and (C) the resulting profile along the x-axis. Solid line is an exponential fit, $e^{-x/\lambda}$, with $\lambda=380\pm40$ μm averaged over 3 experiments. Scale bar: 100 μm. (D-F) A one-step gene expression cascade in the array: activator (denoted A) patterned in the first compartment and activated GFP (denoted B) patterned at the (D) second, or (E) fourth compartment. In green: GFP profile expressed from gene B. In grey: activator profile, as measured in a parallel array on the same chip. Error bars in (C-E) represent standard deviation of fluorescence data in a single gradient. (F) Kinetics of GFP expressed from gene A (circles) and gene B at the second (squares) and fourth (triangles) compartments.

Figure 5:
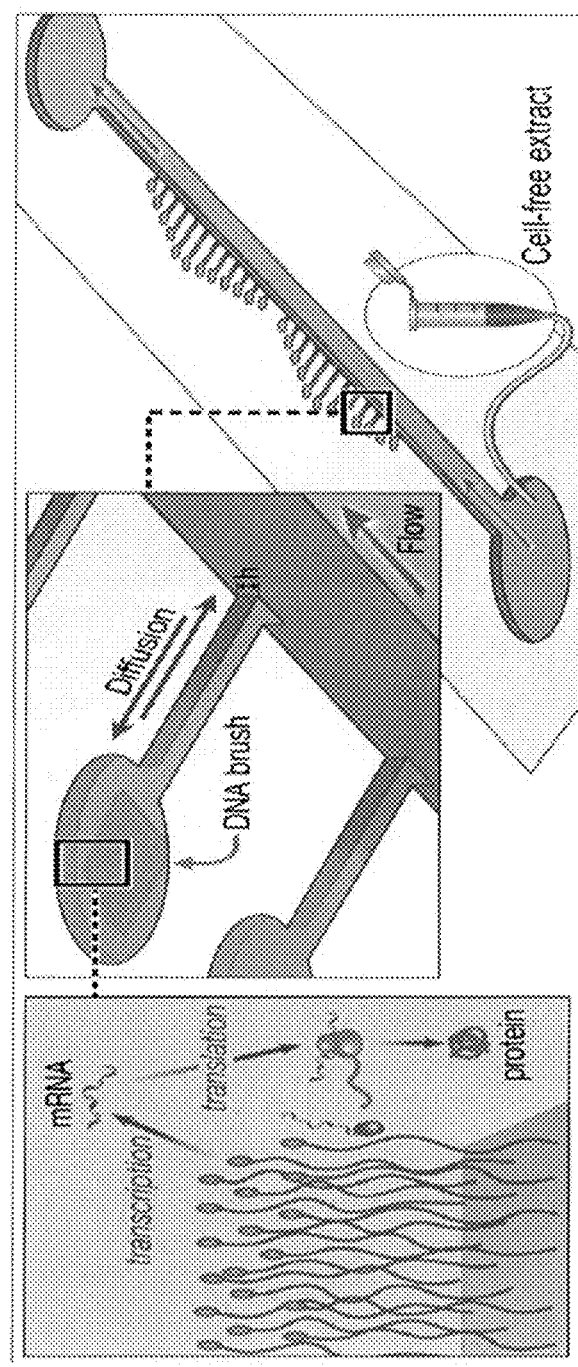

FIG. 5. Microfluidic device and the DNA compartment. DNA brushes patterned (red squares) in circular compartments carved in silicon and connected to a flow channel through a diffusive capillary. The transcription/translation cell extract enters into the thin capillaries (h=1-3 μm) from the main flow channel (h=30 μm) only by diffusion. Proteins expressed from the brush diffuse to the flow channel setting up a source-sink linear gradient.

Figure 6A:
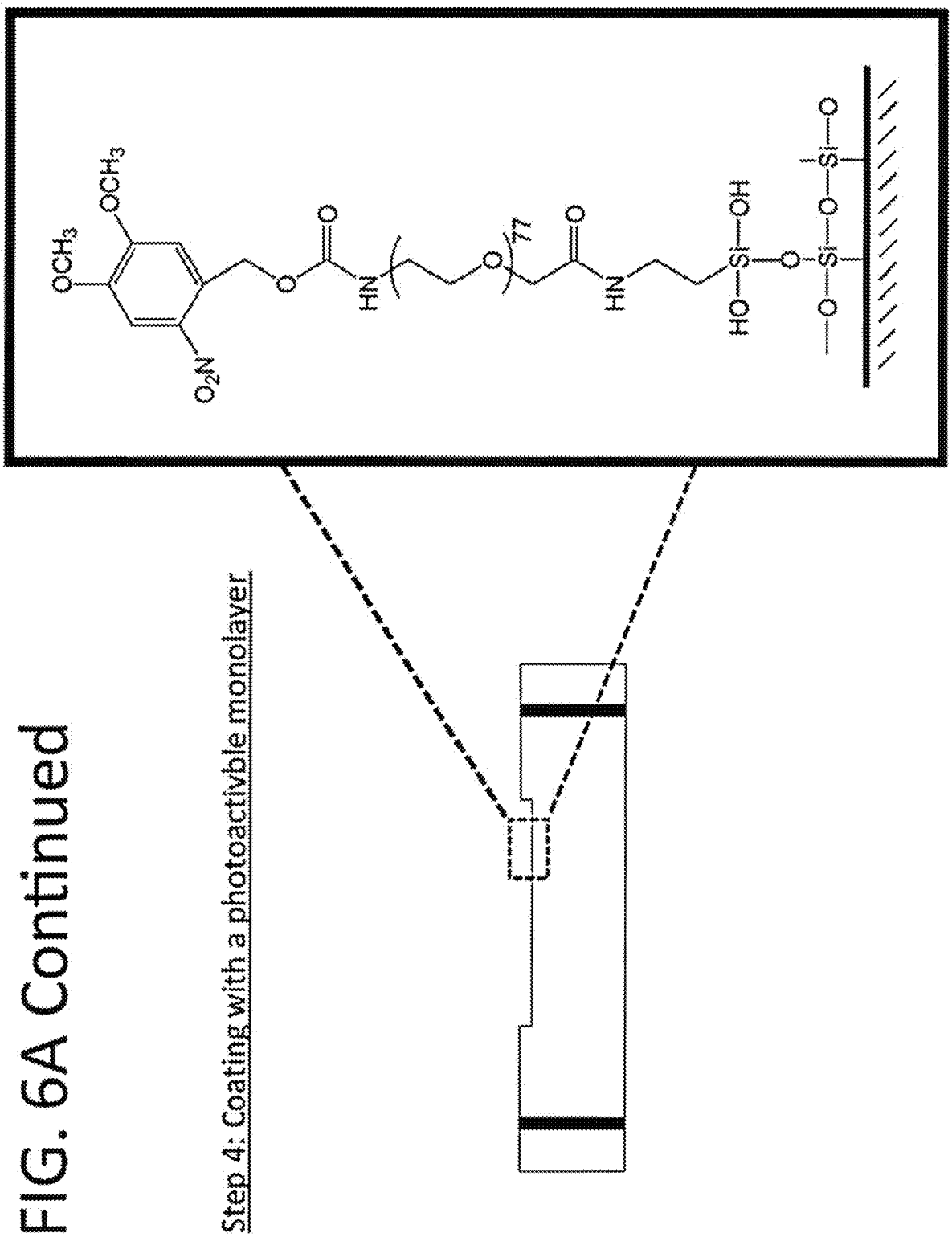
Figure 6A:
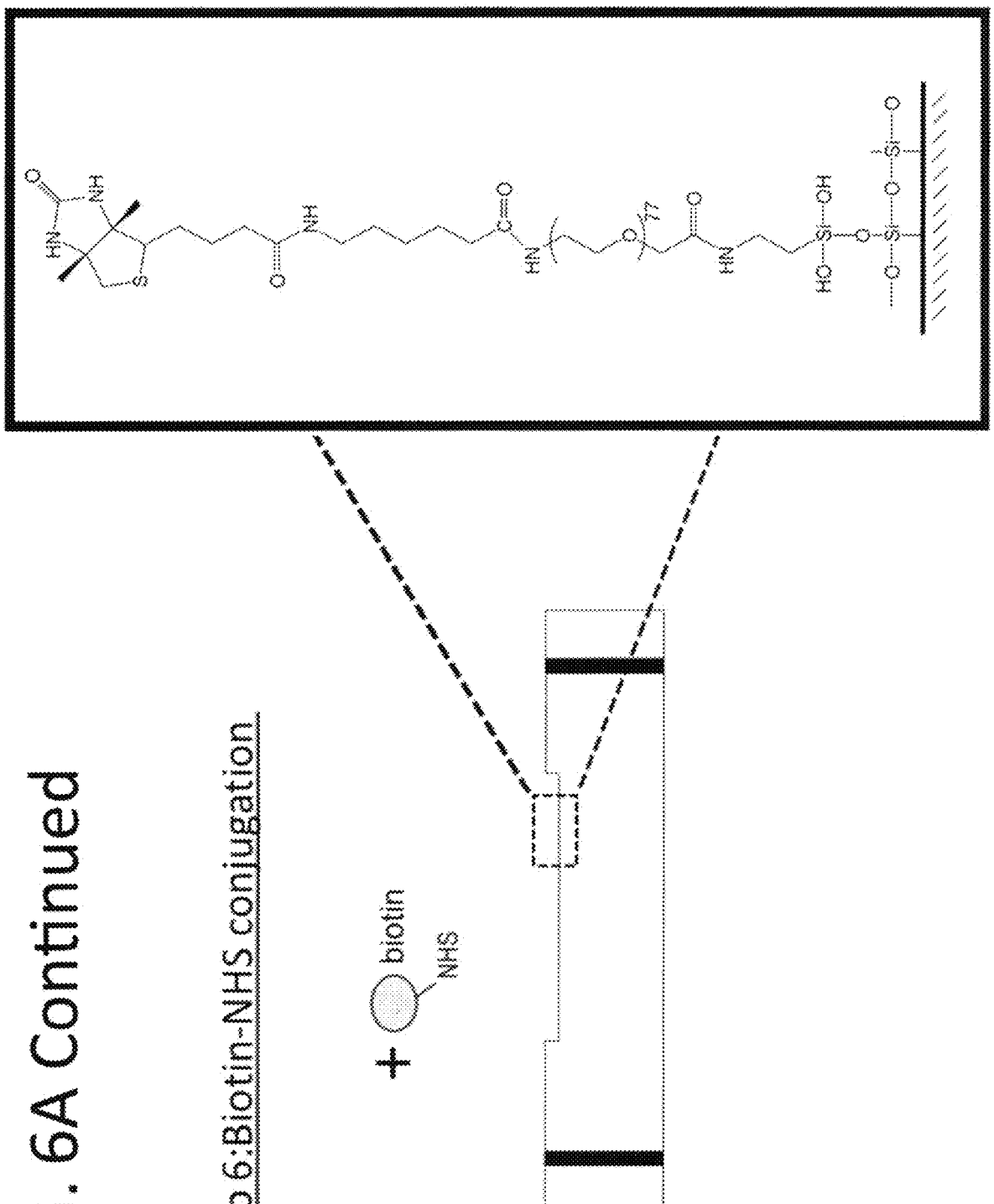
Figure 6B:
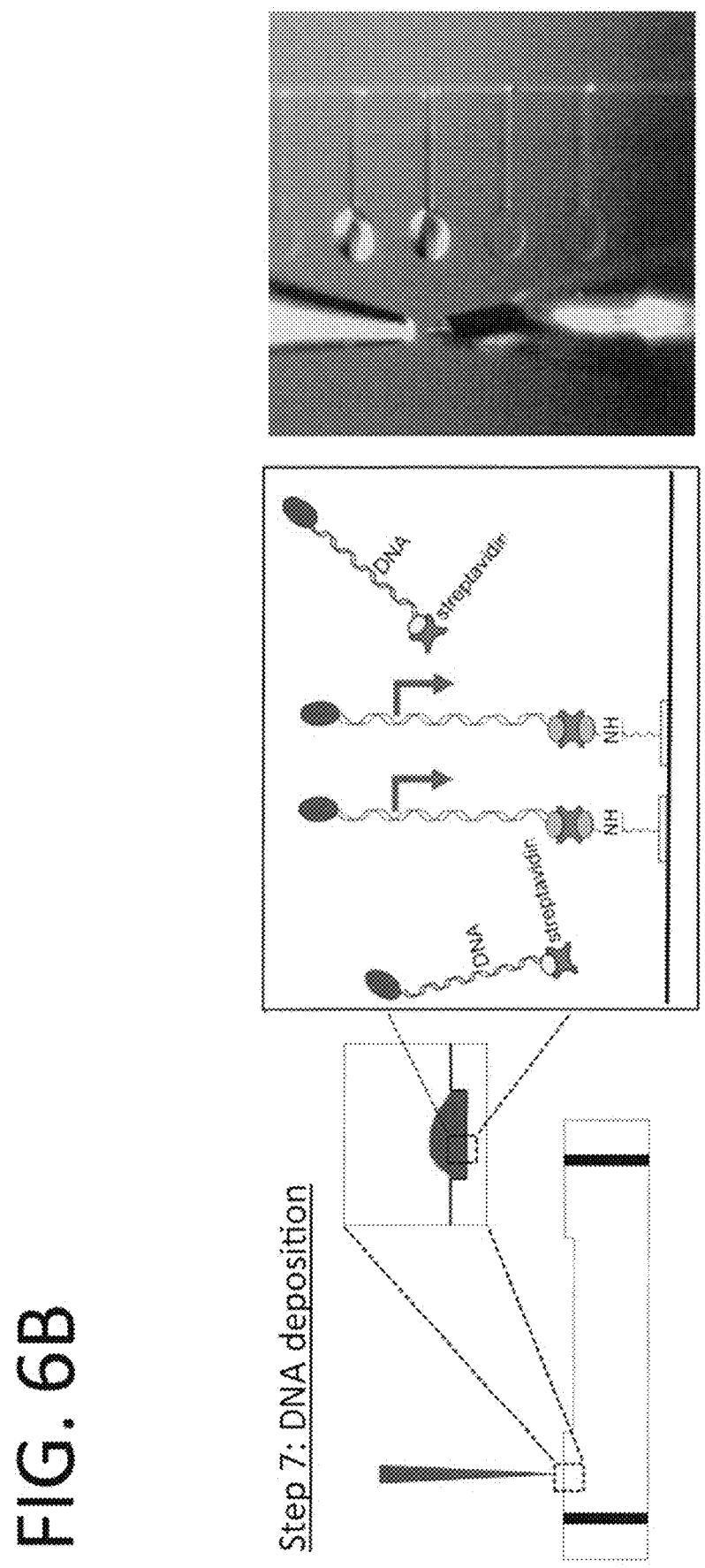
Figure 6B:
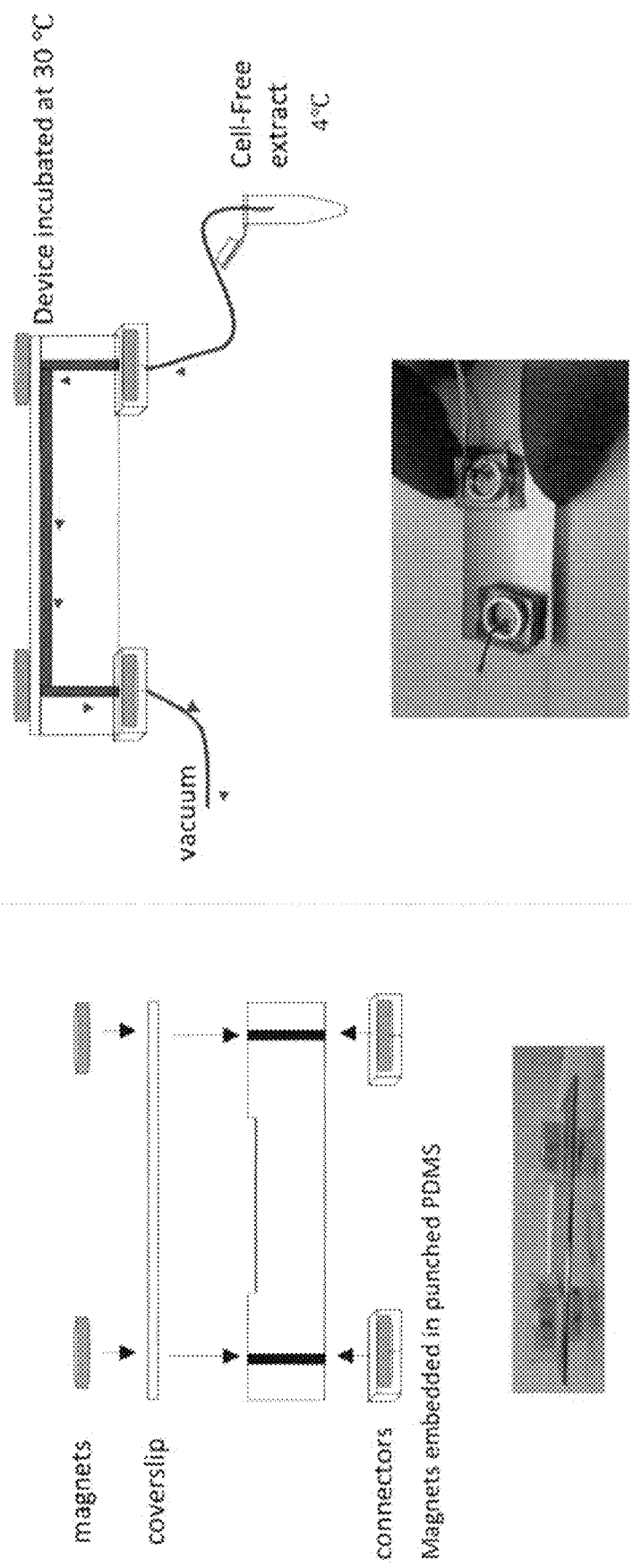
Figure 8A:
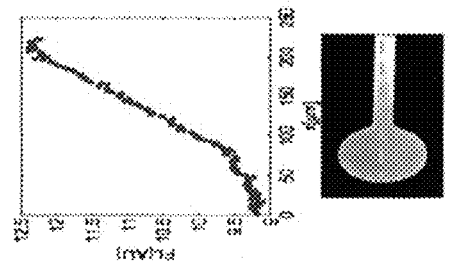
Figure 8B:
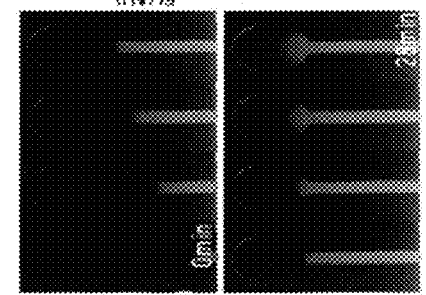
Figure 8C:
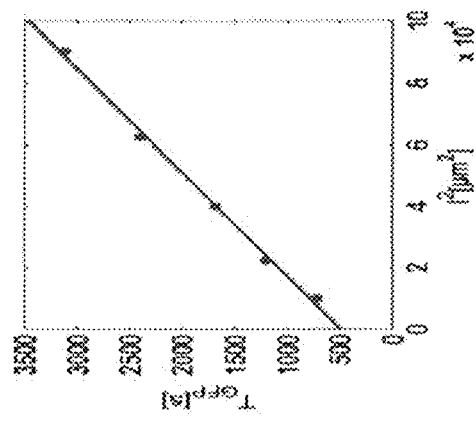
Figure 8D:
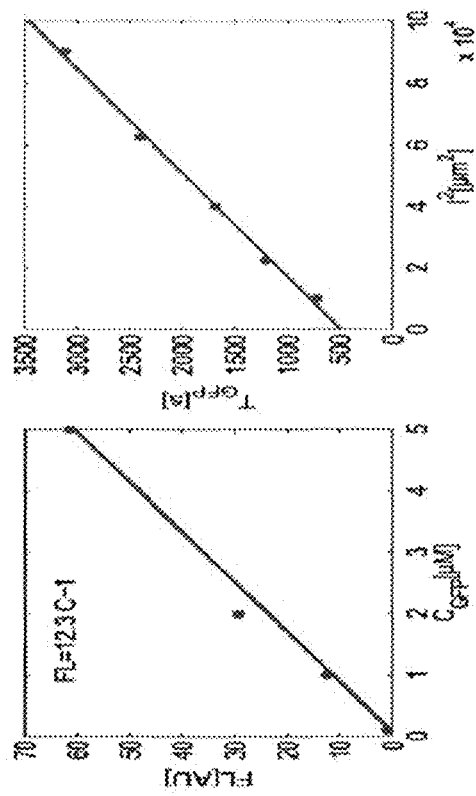

FIGS. 6A-B. Fabrication and assembly of the microfludic device.

FIGS. 7A-G. SEM measurement of the silicon device. (A) Reactor etched 3 μm deep connected to a 30 μm deep flow channel. (B) Magnification of two reactors. Scale bar 100 μm. (C) Magnification of the chamber wall. Scale bar 5 μm (D) Magnification of the interface between the capillary channel and the flow channel. Scale bar is 5 μm. (E) Magnification of the main channel wall. Scale bar 2 μm. (F) Height profile measurement of the compartment (along dashed yellow line). (G) Height profile measurement of the main channel (along dashed yellow line).

FIGS. 8A-D. GFP calibration and diffusion into the compartments. (A) Calibration of the concentration of GFP expressed in the microfluidic chamber. Fluorescent intensity measurements verses protein concentrations. (B) Measurement of GFP diffusion time along the capillary from the flow channel up to the chamber as a function of capillary channel length. (C) Fluorescence time-lapse images of GFP diffusing along the 200 μm capillary from the flow channel into the chamber. Scale bar 100 μm. (D) GFP profile between the main channel and the DNA-compartment. The main channel was first filled with PBS and then with GFP. GFP formed a linear concentration gradient from a maximal value in main channel down to the compartment.

FIGS. 9A-C. Kinetics and linear profile of GFP. (A) GFP intensity in arbitrary units (AU) in the DNA compartment as a function of time, for L=300 μm. (B) GFP profile along the capillary at different time points indicated by color code matching the colored time points in (A). (C) GFP expression rate at the first hour of expression (L=300 μm) as a function of the gene density given in ratio of GFP coding DNA to non-coding DNA.

FIGS. 10A-E. Activator and repressor network scheme. (A) Unregulated gene activated from $\sigma^{70}$ factor in the extract solution and expressing GFP. (B) A construct with positive feedback expressing araC activator and GFP. (C) A construct with negative feedback expressing GFP fused to a Cro repressor dimer. (D) An activator repressor network with activator $\sigma^{38}$ and repressor cI. (E) An activator repressor network with activator $\sigma^{28}$ with repressors cI and Cro.

Figure 11:
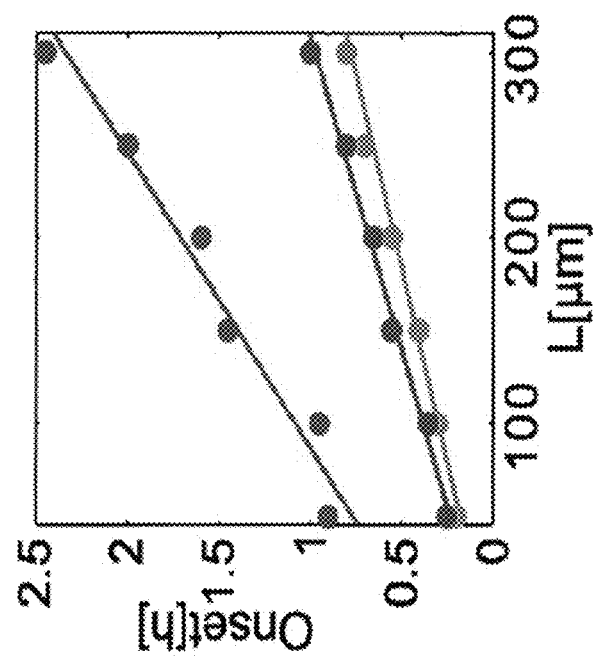

FIG. 11. GFP Expression Onset time. Onset time of GFP in the chamber as a function of the capillary length for the different constructs: unregulated (green dots), positive feedback (blue dots) and negative feedback (red dots).

Figures 12A, 12B, 12C:
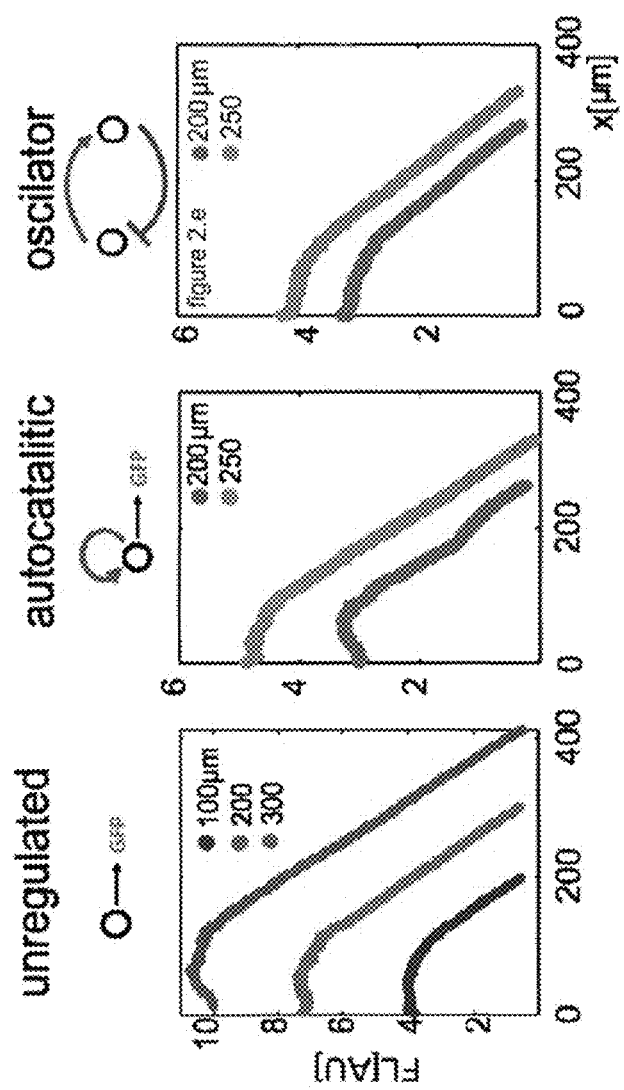
Figures 13A, 13B, 13C:
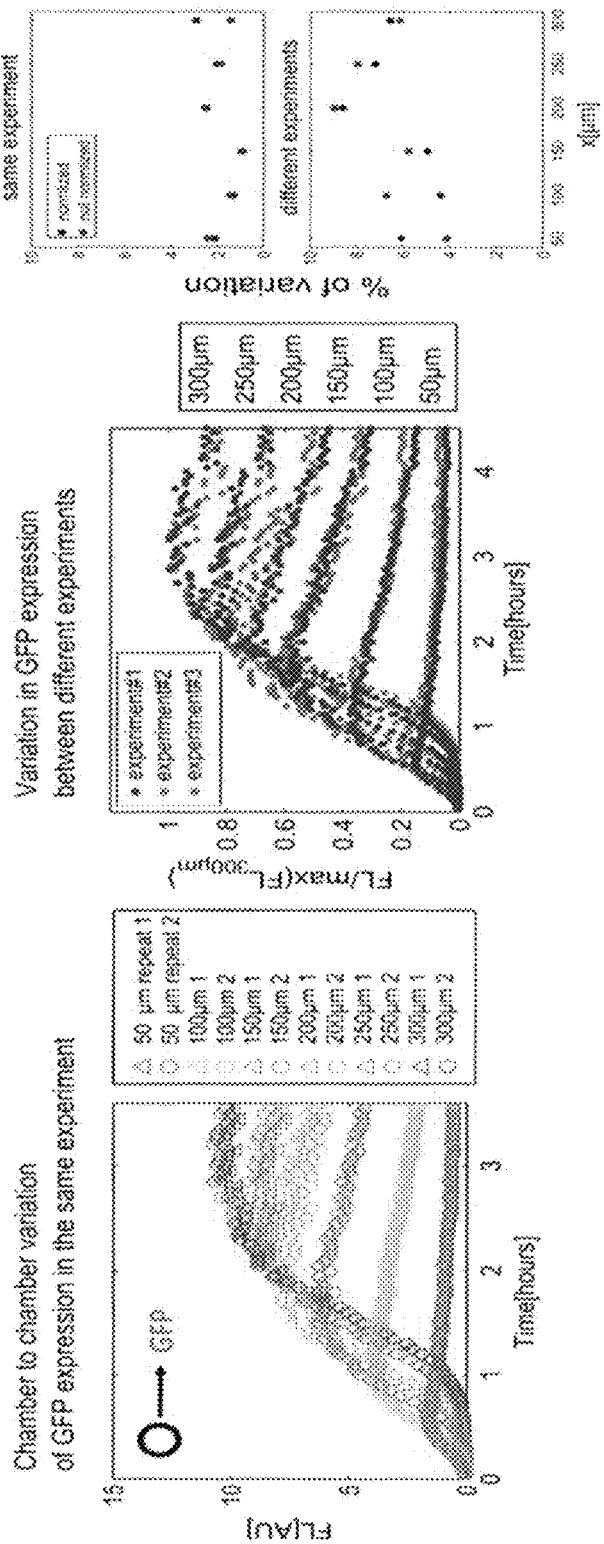
Figure 13D:
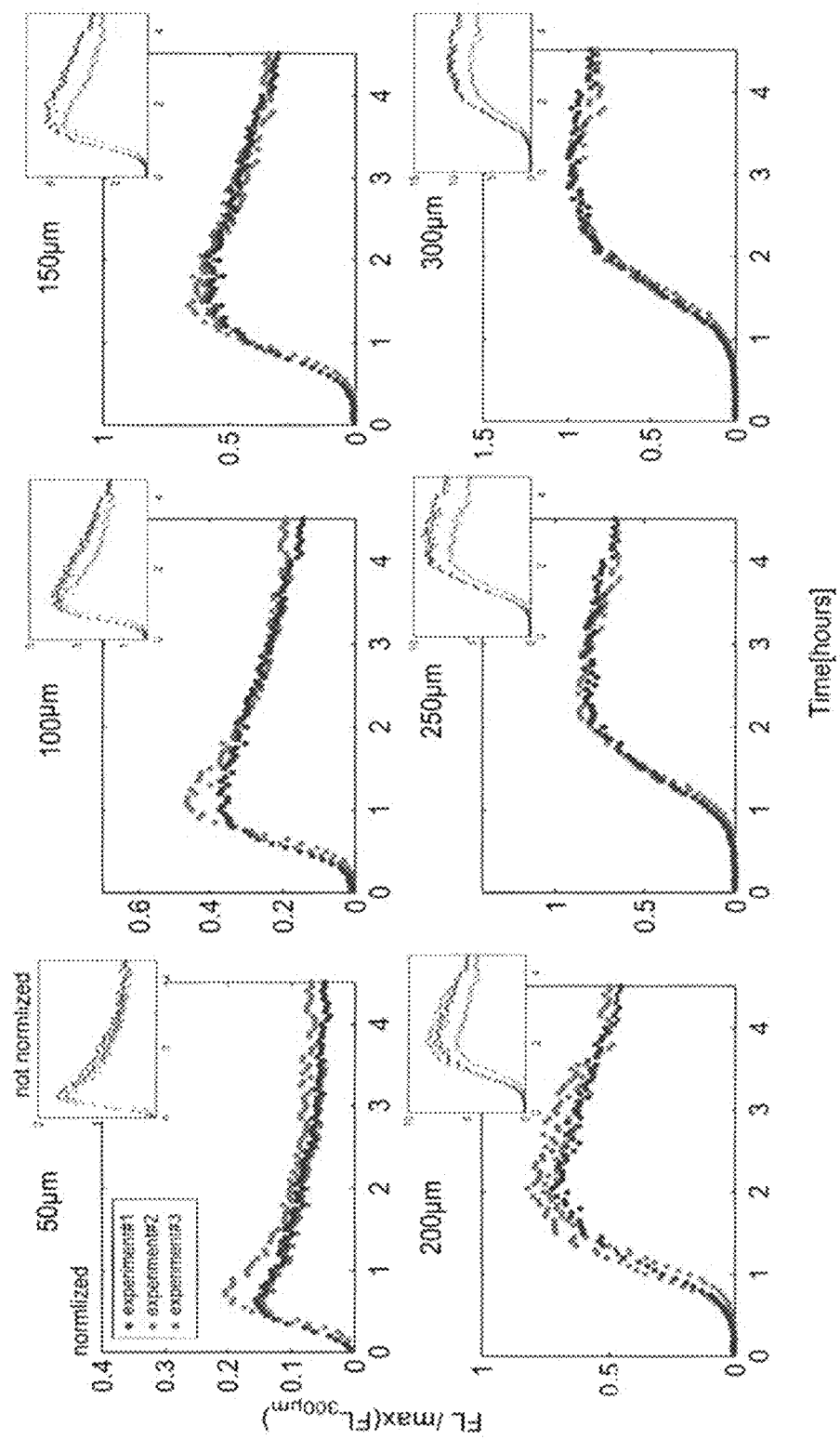

FIGS. 12A-C. GFP profile slope. GFP profile along the capillary in (A) unregulated construct for lengths 100 μm, 200 μm and 300 μm. (B) Autocatalytic construct for lengths 200 μm and 250 μm. (C) Oscillator construct for lengths 200 μm and 250 μm. Gradient slope is independent of capillary length.

FIGS. 13A-D. Gene expression variation for the unregulated construct. (A) Variation of GFP expression between compartments in the same experiment for the unregulated construct. Two repeats of expression kinetics in the DNA compartment for varying capillary length L=50-300 μm. (B) Variation of GFP expression between compartments in three different experiments for varying capillary length. GFP expression is normalized to the maximal intensity value of the capillary L=300 μm within a single experiment. (C) Percentage of chamber to chamber variation in the same experiment, and between different experiments as a function of capillary length for normalized and non-normalized kinetics. The variation is calculated as the standard deviation of the relative difference between two identical compartments. (D) Normalized GFP dynamics in the DNA chamber for three experiments, and (inset) non-normalized dynamics.

Figure 14:
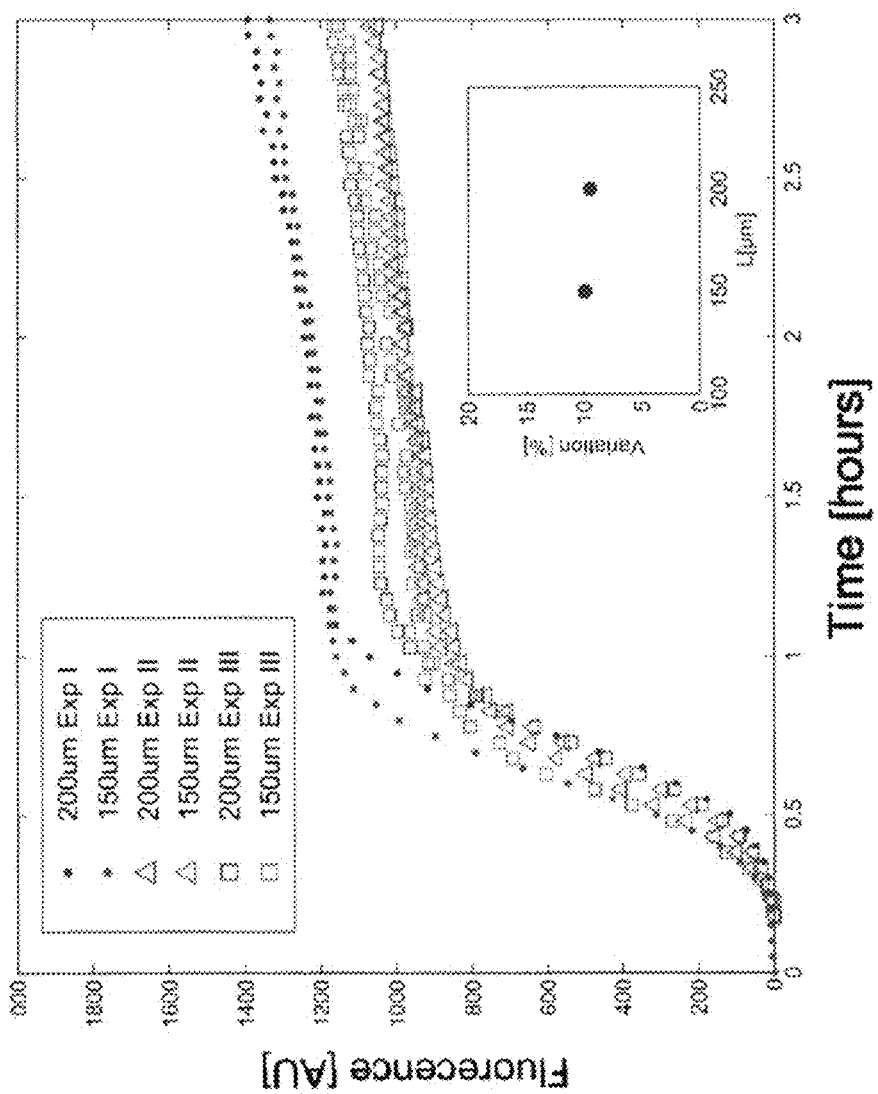

FIG. 14. Gene expression variation for the self-repressing construct. Variation of expression between compartments in different experiments for a construct with negative feedback expressing GFP fused to a Cro repressor dimer. Three repeats of expression kinetics in the DNA compartment for two capillary lengths L=150,200 μm. (inset) Percentage of chamber to chamber variation as a function of capillary length.

FIGS. 15A-F. Oscillatory networks.
(A) Network scheme. Activator is the sigma factor, $\sigma^{28}$, coded by gene A. Two repressor proteins were lambda phage CI (coded by gene B) and Cro (coded by gene C). The four networks are detailed in Table 3. (B) Oscillation period as a function of capillary length for the four networks (C-F). (C-F) GFP kinetics as a function of time. Networks numbers are: (C) 2, (D) 3, (E) 4, (F) 5 as detailed in Table 3.

FIGS. 16A-E. Activator and repressor pulse dynamics. (A-D) GFP dynamics of the $\sigma^{38}$–cI activator-repressor network at different Activator:Repressor:GFP reporter DNA ratios ($D_A$: $D_R$: $D_G$) and at varying capillary length L=100-250 μm. The GFP reporter is under the activator promoter. (E) GFP levels as a function of DNA stoichiometry $D_G/D_R$ after 5 hours of expression for L=200 μm. Network is detailed in Table 3.

FIGS. 17A-D. Protein degradation by ClpXp. (A-B) Dynamics of GFP expression with GFP fused to SsrA degradation tag in an unregulated construct for capillary lengths L=100-250 μm. (C-D) Dynamics of GFP expression with GFP fused to YbaQ degradation tag in an activator repressor network ($\sigma^{38}$-CI, Network 1) for capillary lengths L=100-250 μm.

Figure 18B:
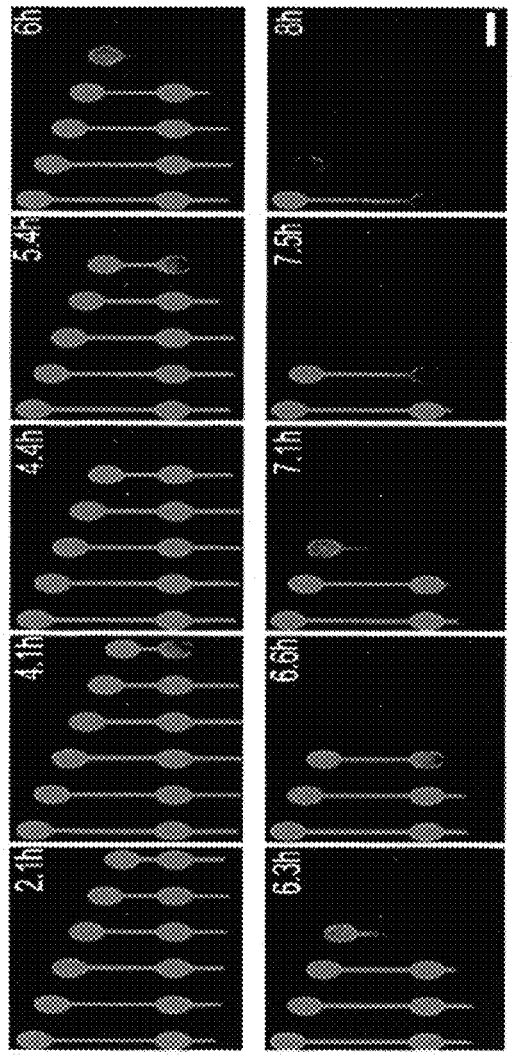
Figure 18A:
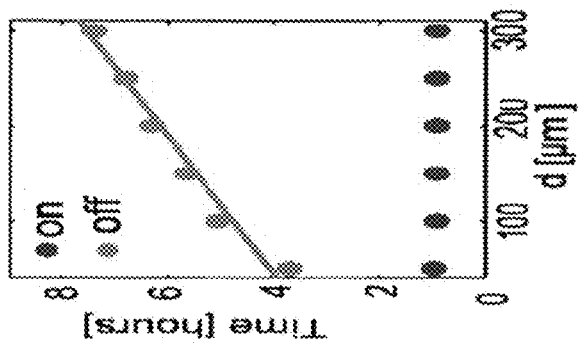

FIGS. 18A-B. Communication between connected DNA compartments. (A) Expression onset (blue) and offset (green) times as a function of distance between the two compartments, as determined by measuring the time of GFP levels above 100 [AU] and below $2.5 \cdot 10^3$ [AU], respectively. The solid line is a linear fit. (B) GFP time lapse images, showing hierarchal shut down with distance between the two compartments. To improve contrast the image maximal intensity was set at $5 \cdot 10^3$ [AU]. Scale bar 200 μm.

Figure 19:
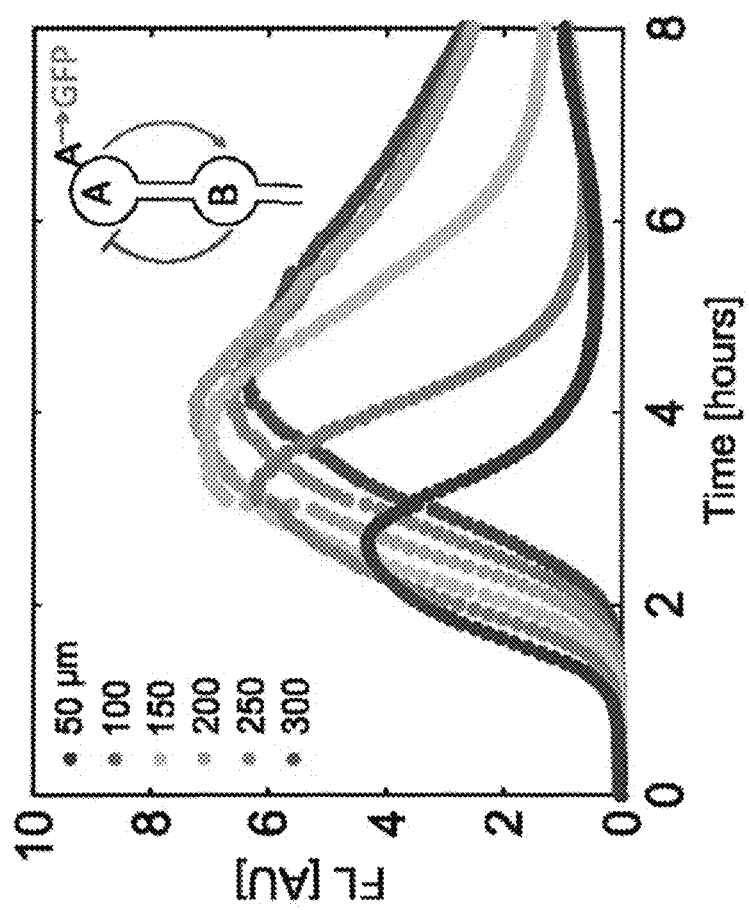
Figure 20C:
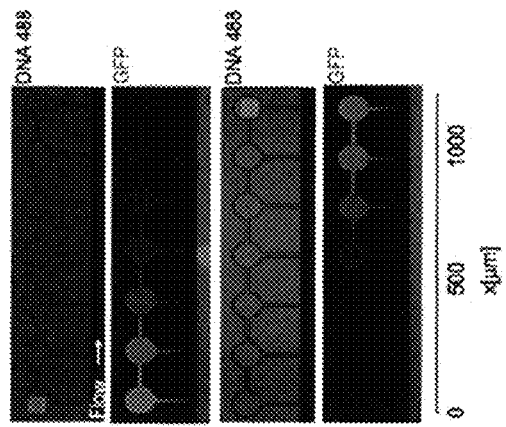
Figure 20D:
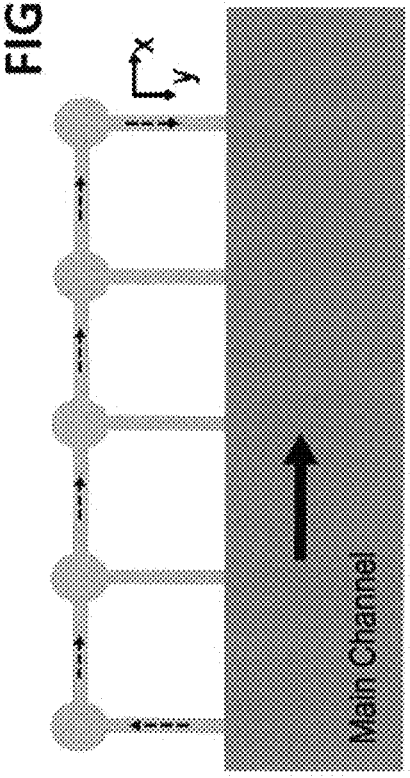
Figure 20A:
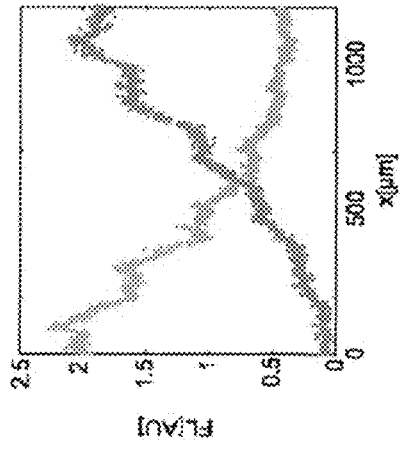
Figure 20B:
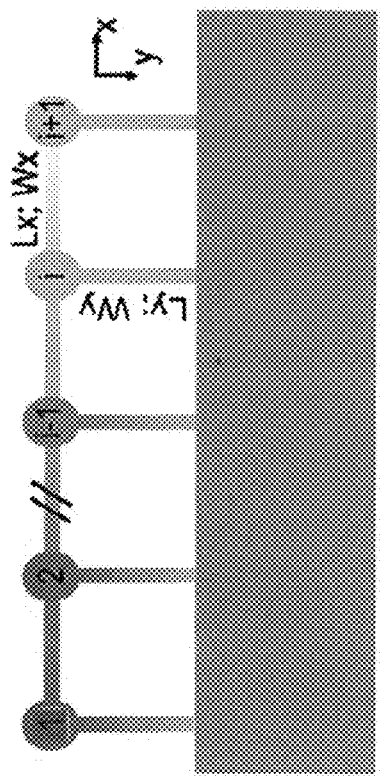

FIG. 19. Communication between connected DNA compartments for genes patterned in reverse order. GFP kinetics as a function of time for an activator-repressor network patterned in two connected compartments. Compartment B is 100 μm away from the flow channel and patterned with the CI repressor genes. Compartment A is located at a distance d=50-300 μm from compartment B, and contains $\sigma^{38}$ activator and GFP reporter genes (network 1).

FIGS. 20A-D. One-dimensional array of connected compartments. (A) Illustration of an array of connected compartments. DNA source is in chamber number 1 and the synthesized protein diffuses to the adjacent compartments along the x-axis. In addition, the protein diffuses along the y-axis to the main channel and evacuates from the chambers. (B) Flow profile along the capillaries and in the main channel. Our design minimized the flow between the compartments. (C) GFP expression profile along the x-axis generated from a source that is located along (yellow) and against (green) the direction of flow. The GFP intensity is homogenous within a compartment, decays linearly between two neighboring compartments. (D) Fluorescent images of DNA brushes (red label, 647 nm) before expression and the GFP images along and against the direction of flow.

Figure 21:
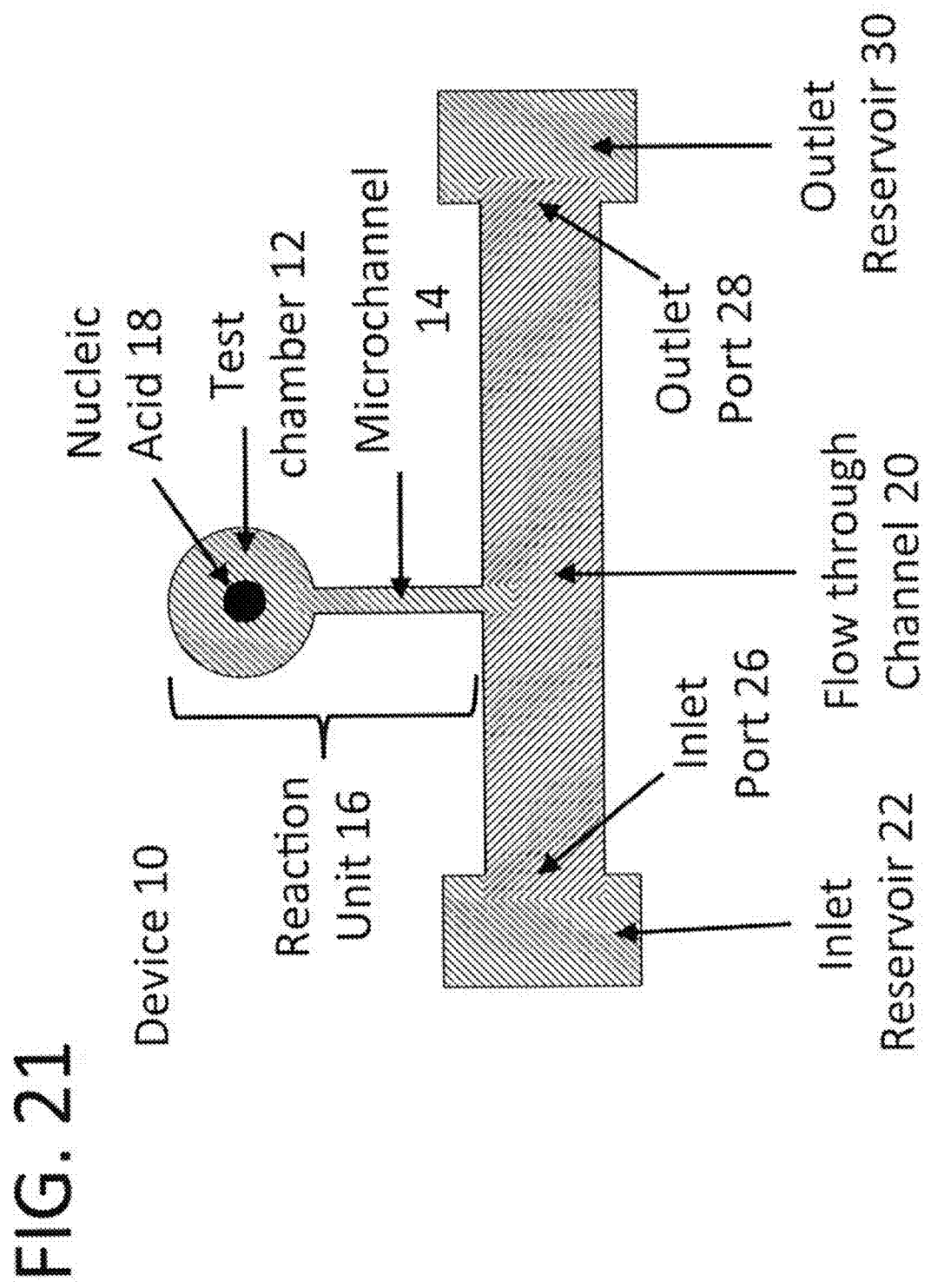

FIG. 21. is a diagram of an exemplary device according to embodiments of the invention.

Figure 22:
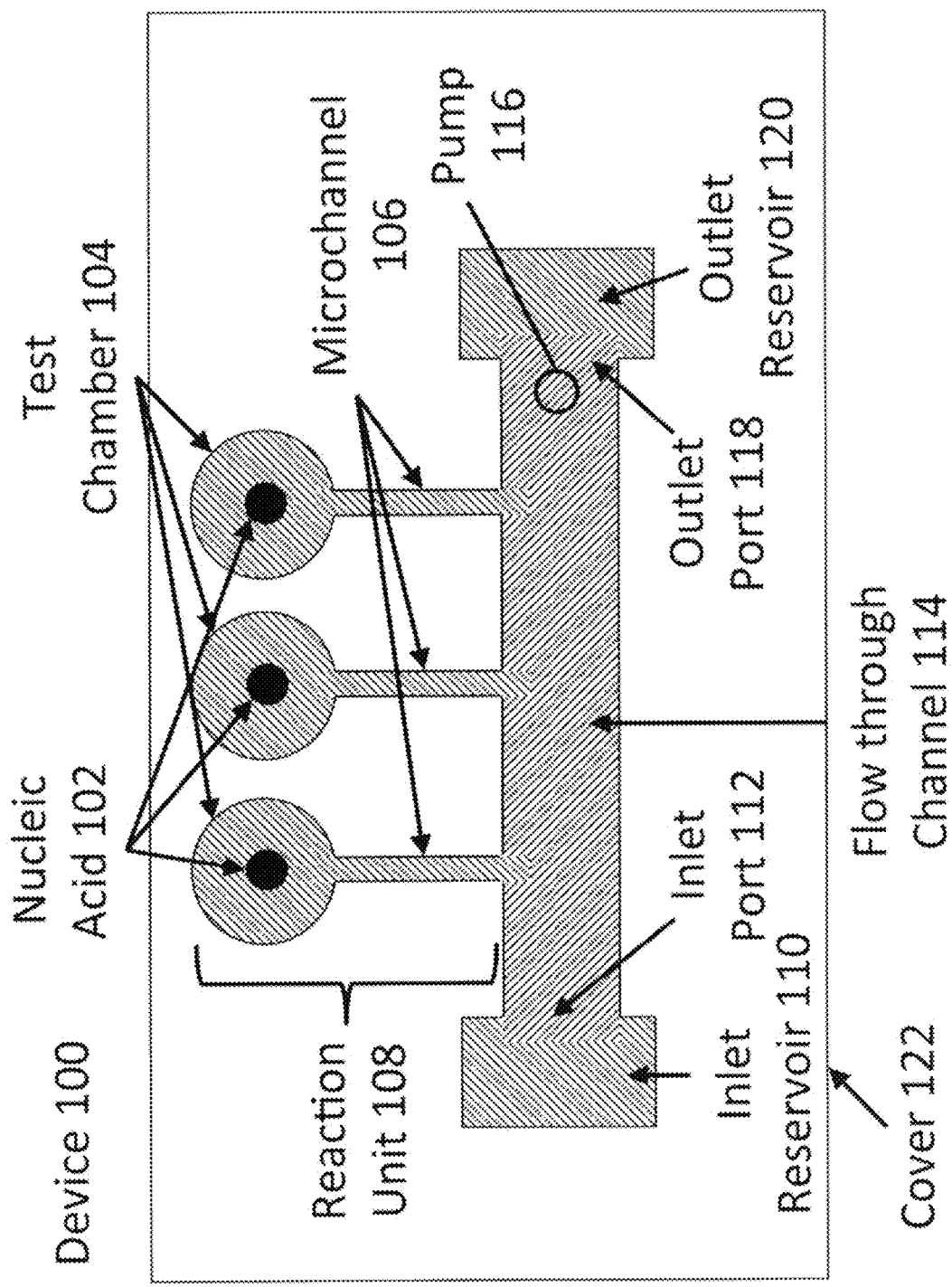

FIG. 22. is a diagram of an exemplary device according to embodiments of the invention.

DESCRIPTION OF SPECIFIC EMBODIMENTS OF THE INVENTION

The present invention, in some embodiments thereof, relates to a microfluidic device for analyzing cell-free gene expression.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The assembly of artificial cells capable of executing synthetic DNA programs has been an important goal for basic research and biotechnology. The present inventors assembled a microfluidic device comprising at least one two-dimensional DNA compartment fabricated in silicon which could serve as artificial cells capable of metabolism, programmable protein synthesis, and communication.

Expression at the DNA compartment was maintained by continuous diffusion of nutrients and enzymes through a thin capillary, connecting protein synthesis in the DNA compartment with the environment.

The dimensions of the device were such that proteins expressed in the DNA compartment generated gradient profiles with essentially no flow in the region. The gradients were created by diffusion of the expressed proteins from the DNA compartment and into the thin capillary. The thin capillary is connected to a flow through chamber, through which the nutrients and enzymes necessary for expression are continuously flowed. The device was designed in such a way that, in spite of the perfusion flow through the flow-through chamber, there was no flow in the regions where the gradient profiles were established.

Whilst reducing the present invention to practice, the present inventors programmed protein expression cycles, auto-regulated protein levels, and a signaling expression gradient, equivalent to a morphogen, in the device. Gene expression in the DNA compartment revealed a rich dynamical system that is controlled by geometry, offering a means for studying biological networks outside a living cell.

Microfluidic devices generated according to the teachings of the present invention can be employed in a myriad of microfluidic applications including various chemical and biochemical analyses and syntheses, both for preparative and analytical applications.

Thus, according to one aspect of the present invention there is provided a microfluidic device. The microfluidic device comprises:

(i) at least one reaction unit having a test chamber connected to at least one microchannel, wherein a surface of at least a portion of said reaction unit is attached to an isolated nucleic acid; and (ii) a flow-through channel having at least one inlet port and at least one outlet port, said flow-through channel and said at least one microchannel being of dimensions to allow reactant diffusion to and from said reaction unit, wherein the diffusion time of said reactant along the microchannel is shorter than the flow time along the microchannel.

As used herein the phrase "microfluidic device" refers to a synthetic device in which minute volumes of fluids are flowed. The flow channel is generally fabricated at the micron to sub-micron scale, e.g., the flow-through channel typically has at least one cross-sectional dimension in the range of less than about 1 mm. Microfluidic devices of the present invention can be incorporated in complicated systems such as those described herein below.

The term "flow-through channel" as used herein, refers to a low resistance flow channel, about 25 microns to about 150 microns deep, preferably about 25 microns to about 100 microns deep and more preferably about 30 microns to about 100 microns deep. Flow-through channels are sufficiently wide (perpendicular to the direction of flow) to not inhibit the flow of fluid through the channel, and not excessively wide to inhibit the function of valves. Such considerations are well understood by those of ordinary skill in the art. Exemplary widths of the flow-through channel are between 100 microns –1 mm wide. The flow-through channel has at least one inlet port and at least one outlet port, at least one of which being in fluid communication with a reservoir such as by tubing. Fluids may be passively or actively infused into the flow channels such as by capillary forces or pumps (e.g., external pumps, e.g., peristaltic pumps or electro-osmotically pumps).

Flow through the flow-through channel may be regulated using a valve.

A "valve" is a component of the device that regulates flow through a fluid channel of the device by substantially inhibiting flow through the fluid channel upon closure. Substantially inhibiting the flow means that flow is inhibited at least 80%, preferably at least 90%, more preferably at least 95%, even more preferably at least 99%, most preferably flow is completely (i.e., 100%) inhibited. The size of the valve is dependent on the size and shape of the fluid channel and the amount of pressure required to close the valve. In a preferred method, the fluid channel is about 250 microns wide and the valve is about 300 microns wide. The channel and control valve cross perpendicularly. Upon actuation of the valve, preferably by hydrostatic pressure, the channel closes and opens.

As used herein, the term "test chamber" refers to a compartment of the device which is connected to the flow through channel via a microchannel. The test chamber may be any shape—e.g. rectangular, square or circular. According to one embodiment, the test chamber is circular and has a diameter of about 50-200 microns.

The chambers typically have a volume of less than 100 pl, in other instances less than 50 pl; in other instances less than 40 pl, 30 pl, 20 pl or 10 pl.

The term "microchannel" as used herein, refers to a high resistance channel, about 1 micron to about 20 microns deep, more preferably about 1 micron to about 10 microns deep. The length of the microchannel can vary between 20 microns to about 1 mm or between 20 microns to about 500 microns. The width of the microchannel is typically between 2-50 microns. According to embodiments of the present invention the ratio of the width of microchannel:width of the flow-through channel is greater than 1:5. Exemplary ratios include 1:5, 1:6, 1:7, 1:8, 1:9, 1:10 and 1:20.

Figure 1D:
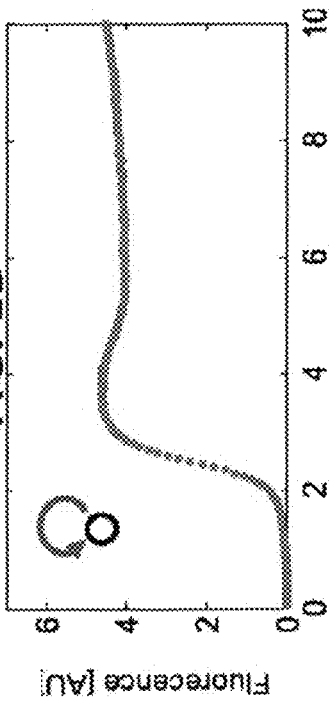

The length of the microchannel determines the dilution time of proteins in the reaction unit and therefore determines the steady state concentration of the expressed proteins or the oscillation period of activator-repressor network (see for example FIG. 1D).

According to a particular embodiment, the hydrodynamic resistance of the microchannel is at least 5 or 6 orders of magnitude higher than in the flow-through channel. This reduces the flow in the microchannel by 5 or 6 orders of magnitude compared with the flow in the flow chamber. Furthermore, in the case where the microchannel is connected to the flow channel in one point only, there is no pressure gradient along the micro-channel and therefore there is no flow.

For a channel with length L, height h, width W and with a fluid with viscosity $\eta$ the hydrosynamic resistance is given by $$R = \frac{1}{5} \frac{L \cdot \eta}{h^3 W \left(1 - 192 \frac{h}{\pi^5 W} \tanh\left(\frac{\pi W}{2h}\right)\right)}.$$

If we compare two channel with $L_1=L_2=100$ μm, $W_1=10$ μm, $W_2=900$ μm, $h_1=2$ μm, $h_2=50$ μm we find that the resistance ratio $$\frac{R_1}{R_2} = 1.55 \cdot 10^6.$$

Each test chamber is connected to the flow-through channel by at least one microchannel so as to allow diffusion of molecules to and from the reaction unit. The microchannel according to embodiments of this aspect of the present invention is essentially perpendicular to the flow-through channel. The combination of the test chamber and its connected microchannel is referred to herein as a reaction unit.

It will be appreciated that a reaction unit may comprise more than one test chamber. Thus, the present invention contemplates a reaction unit comprising two test chambers, one being directly connected to the flow chamber by the microchannel, and the second being connected to the flow chamber via the first reaction unit—see for example FIG. 3A.

The microchannel length between the two reaction units determines the delay time between the synthesis of a protein in one compartment and the time it reaches the $2^{nd}$ compartment. Thus, the capillary length controls a delay time that can be used for example to create a temporal gene expression pulse (FIGS. 3A,B).

Resistance of fluid flow through the reaction unit is higher than the resistance in the flow-through channel. This resistance is typically established by having reaction units that are substantially and sufficiently shallower and/or narrower than the adjacent flow-through channels to create resistance such that there is essentially no flow in the reaction unit. Such parameters can be readily determined by one of ordinary skill in the art using mathematical or empirical modeling. According to a particular embodiment, the depth ratio of the reaction unit:flow-through channel is greater than 1:5. Exemplary ratios include 1:5, 1:6, 1:7, 1:8, 1:9, 1:10 and 1:20.

In the case of a single reaction unit, with only one connection to the flow channel, there is no pressure gradient along the microchannel thus there is no flow. In the case of two compartments that are connected by a micro channel in parallel to the flow-channel, there are two points of connection between the main channel and the microchannels. In this case there is a pressure gradient along the microchannel, however diffusion time of a molecule along the microchannel is still shorter than the flow time along the microchannel.

By altering the dimensions of the microchannel and the flow channel, the $\tau_{flow}/\tau_{diffusion}$ can be controlled. Thus, according to one embodiment, the $\tau_{flow}/\tau_{diffusion}$ is about 1%. According to another embodiment, the $\tau_{flow}/\tau_{diffusion}$ can be about 0.1%.

In further embodiments, the rate of flow in the microchannel is less than about 10% than that in the direction of fluid flow in the flow-through channel. In a preferred embodiment, the rate of flow in the microchannel is less than about 5%, more preferably less than about 1%, most preferably less than about 0.1% of the flow rate in the flow-through channels in the device.

In further embodiments, the rate of flow in the test chamber is less than about 10% than that in the direction of fluid flow in the flow-through channel. In a preferred embodiment, the rate of flow in the test chamber is less than about 5%, more preferably less than about 1%, most preferably less than about 0.1% of the flow rate in the flow-through channels in the device.

The device of the present invention can comprise 1, 2, 3, 4, 5, 6, 7, 8, 9, 10 or more reaction units connected to a single flow-through channel.

Figure 1E:
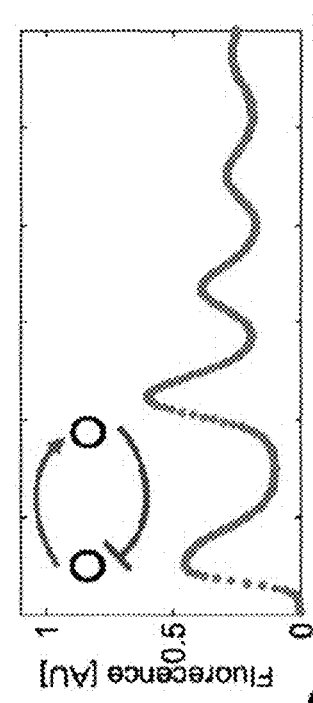
Figure 1F:
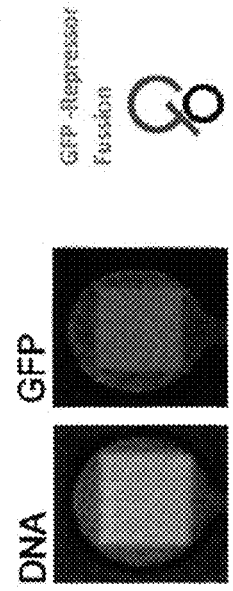
Figure 1A:
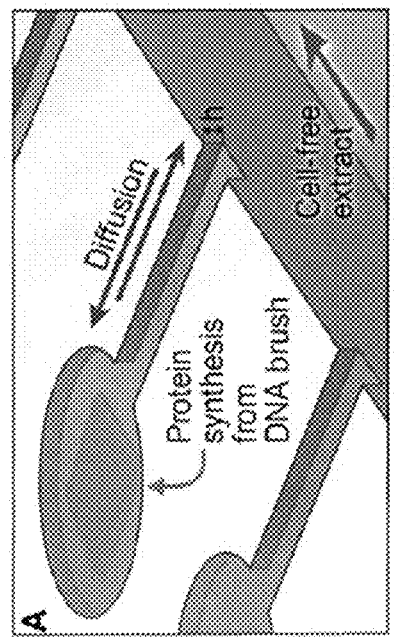
Figure 1B:
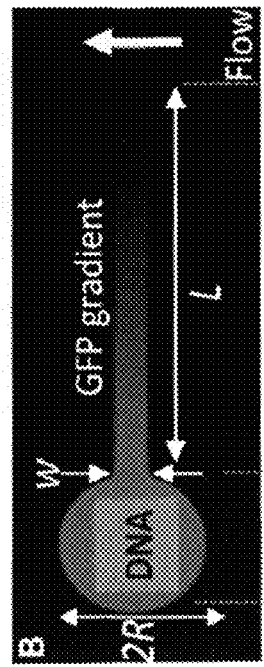

The dimensions of the device are such that the RNA and/or protein expressed in the reaction unit forms a gradient along the microchannel, wherein the concentration at where the nucleic acid is attached (for example at the test chamber) is the highest, gradually decreasing along the microchannel such that the concentration of the protein at the junction of the microchannel and flow-through channel is at its lowest—(see for example FIG. 1B). According to one embodiment, the RNA and/or protein expressed in the reaction unit may create a linear or exponential profile.

It will be appreciated that when the device comprises more than one reaction unit, the length of the microchannel in each of the reaction units may be identical or non-identical (see FIG. 2G).

It will further be appreciated that when the device comprises more than one reaction unit, at least one of the test chambers of the first reaction unit may be connected to at least one of the test chambers of the second reaction unit via a second microchannel (see for Example FIG. 4A). The second microchannel may be of similar dimensions to the first microchannel described herein above, such that the rate of flow in the second microchannel is similar to the rate of flow in the first microchannel. Alternatively, the second microchannel may be of different dimensions to the first microchannel described herein above, such that the rate of flow in the second microchannel is different to the rate of flow in the first microchannel.

The device further comprises a cover layer (e.g., glass or plastics) sealed thereto, such that the cover layer forms one wall of the microfluidic path. Alternatively, the device once removed from the mother mold is sealed to a thin elastomeric membrane such that the flow path is totally enclosed in elastomeric material. The resulting elastomeric device can then optionally be joined to a substrate support.

According to one embodiment, the device is sealed using PDMS. The sealing may be covalent or non-covalent. The device may also be sealed using a coated or non-coated coverslip. Exemplary coatings are further described herein below.

Devices of the present invention may be constructed utilizing single and multilayer soft lithography (MSL) techniques and/or sacrificial-layer encapsulation methods. The basic MSL approach involves casting a series of elastomeric layers on a micro-machined mold, removing the layers from the mold and then fusing the layers together. In the sacrificial-layer encapsulation approach, patterns of photoresist are deposited wherever a channel is desired. These techniques and their use in producing microfluidic devices is discussed in detail, for example, by Unger et al. (2000) Science 288:113-116, by Chou, et al. (2000) "Integrated Elastomer Fluidic Lab-on-a-chip-Surface Patterning and DNA Diagnostics, in Proceedings of the Solid State Actuator and Sensor Workshop, Hilton Head, S.C.; and in PCT Publication WO 01/01025.

According to another embodiment, the flow-through channel and reaction units are typically carved (e.g. by etching) directly into a silicon or glass substrate. The device may be recycled by basic piranha cleaning and recoated as further described in the Materials and method section herein below.

The device of the present invention is fabricated from a substrate (i.e. a single material or a combination of materials).

Preferably, the substrate material is substantially non-fluorescent or emits light of a wavelength range that does not interfere with the photoactivation. Examples of such materials include, but are not limited to, silica-based materials (exemplified hereinbelow) and elastomeric materials.

The term "elastomer" and "elastomeric" as used herein refers to the general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application. Examples of elastomeric materials which can be used to fabricate the devices of the present invention include, but are not limited to, GE RTV 615 (formulation), a vinyl-silane crosslinked (type) silicone elastomer (family e.g., PDMS).

The choice of materials typically depends upon the particular material properties (e.g., solvent resistance, stiffness, gas permeability, and/or temperature stability) required for the application being conducted. Additional details regarding the type of materials that can be used in the manufacture of the components of the microfluidic devices disclosed herein are set forth in Unger et al. (2000) Science 288:113-116, and PCT Publications WO 02/43615, and WO 01/01025. Exemplary low-background substrates include those disclosed by Cassin et al., U.S. Pat. No. 5,910,287 and Pham et al., U.S. Pat. No. 6,063,338.

Preferred elastomers of the instant invention are biocompatible, gas permeable, optically clear elastomers useful in soft lithography including silicone rubbers, most preferably PDMS. Other possible elastomers for use in the devices of the invention include, but are not limited to, polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(l-butene), poly (chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

In a preferred embodiment, the substrate material is substantially non-reactive with nucleic acids, thus preventing non-specific binding between the substrate and the nucleic acids. Methods of coating substrates with materials to prevent non-specific binding are generally known in the art. Exemplary coating agents include, but are not limited to cellulose, bovine serum albumin, and poly(ethyleneglycol). The proper coating agent for a particular application will be apparent to one of skill in the art.

As mentioned, the surface of at least a portion of the reaction unit is attached to an isolated nucleic acid.

As used herein, the phrase "isolated nucleic acid" refers to a nucleic acid which is not comprised in or on a cell.

According to another embodiment, when the isolated nucleic acid is attached to the reaction unit, it is devoid of cellular components (such as proteins, lipids etc.)

The nucleic acid may be single stranded or double stranded. The nucleic acid may be DNA (e.g. cDNA, genomic DNA, synthetic DNA), RNA, a combination of both. The nucleic acid may be isolated from a cell, or may by synthesized in vitro. Typically, the nucleic acids of this aspect of the present invention comprise at least one promoter and encode a polypeptide.

The nucleic acids may be of any length. According to a particular embodiment, the nucleic acids are between 200 bp-500 kbp, or between 200 bp-2000 kbp, or between 200 bp-100 kbp, or between 200 bp-40 kbp, or between 200-5000 bp.

According to a particular embodiment, the distance between the DNA top and the promoter is about 200 bp and a similar distance between the terminator and the DNA end attached to the surface.

Nucleic acids of this aspect of the present invention are further described herein below.

The nucleic acids of this aspect of the present invention are typically linear.

According to one embodiment, the surface of the test chamber (or portion thereof) is coated with nucleic acids.

According to another embodiment, the microchannel (or portion thereof) is coated with nucleic acids.

According to still another embodiment, the reaction unit and the microchannel are coated with nucleic acids.

Preferably, the density of the nucleic acid on the substrate is between $10^2$ DNA $\mu m^2$-$10^5$ DNA $\mu m^2$, for example in the order of $10^2$ DNA $\mu m^2$.

The nucleic acid of the present invention is typically orientated on the substrate such that the regulatory region of the nucleic acid (e.g. promoter) is closer to the substrate and the polypeptide coding region is further from the substrate.

The isolated nucleic acids may be attached to the reaction unit (or portion thereof) in a wide variety of ways, as will be appreciated by those in the art. The nucleic acids may either be synthesized first, with subsequent attachment to the substrate, or may be directly synthesized on the substrate. The substrate and the nucleic acid may be derivatized with chemical functional groups for subsequent attachment of the two. For example, the substrate may be derivatized with a chemical functional group including, but not limited to, amino groups, carboxyl groups, oxo groups or thiol groups. Using these functional groups, the nucleic acid may be attached using functional groups on the nucleic acid either directly or indirectly using linkers.

The isolated nucleic acid may also be attached to the substrate non-covalently. For example, a biotinylated nucleic acid can be prepared, which may bind to surfaces covalently coated with streptavidin, resulting in attachment. Alternatively, a nucleic acid may be synthesized on the surface using techniques such as photopolymerization and photolithography. Additional methods of attaching nucleic acids to solid surfaces and methods of synthesizing nucleic acids on substrates are well known in the art, i.e. VLSIPS technology from Affymetrix (e.g., see U.S. Pat. No. 6,566, 495, and Rockett and Dix, "DNA arrays: technology, options and toxicological applications," Xenobiotica 30(2):155-177, all of which are hereby incorporated by reference in their entirety).

According to a preferred embodiment of this aspect of the present invention, the substrate is coated with a coat composed of a compound which can be represented by the general formula I below:

$$X\text{-}L\text{-}Y \qquad \text{Formula I}$$

wherein X is the functionalized group capable of binding to a substrate; L is the polymer capable of forming a monolayer on a substrate; and Y is a photoactivatable group capable of generating a reactive group upon exposure to light.

The functionalized group is preferably selected such that it binds to the substrate by reacting with at least one functional group present on a surface of a substrate.

Preferred functionalized groups according to the present invention comprise one or more reactive silyl group(s).

As used herein, the phrase "reactive silyl group" describes a residue of a compound comprising at least one silicon atom and at least one reactive group, such as an alkoxy or halide, such that the silyl group is capable of reacting with a functional group, for example on a surface of a substrate, to form a covalent bond with the surface. For example, the reactive silyl group can react with the surface of a silica substrate comprising surface Si—OH groups to create siloxane bonds between the compound and the silica substrate.

Exemplary reactive silyl groups that are usable in the context of the present invention include, without limitation, trialkoxysilanes, alkyldialkoxysilanes, alkoxydialkylsilanes, trihalosilanes, alkyldihalosilanes and dialkylhalosilanes. Such reactive groups are easily reacted when contacted with free hydroxyl groups on a surface of solid surfaces and particularly with such hydroxyl groups on a silica surface.

Herein, the terms "silica" and "$SiO_2$" are used interchangeably.

In a preferred embodiment of the present invention the reactive silyl group is trialkoxysilane such as, for example trimethoxysilane, triethoxysilane, tripropyloxysilane or trihalosilane such as, for example, trichlorosilane.

The functionalized group according to the present invention may further include a chemical moiety that is terminated with the reactive silyl group. Such a chemical moiety can comprises, for example, alkyl, alkenyl, aryl, cycloalkyl and derivatives thereof, as these terms are defined herein.

Preferably, the functionalized group comprises an alkyl terminating with a trialkoxysilane.

As discussed hereinabove, the polymer is selected so as to form a monolayer on the substrate. Thus, the polymer group in the compounds of the present invention may be any hydrophobic, hydrophilic and amphyphilic polymer that has suitable characteristics for forming a monolayer. Such characteristics include, for example, long, relatively inert chains, which may interact therebetween via e.g., hydrogen or Van-der-Waals interactions.

A preferred polymer according to the present invention comprises polyethylene glycol (PEG). As described hereinabove, PEG is characterized by resistance to nonspecific absorptions of biomolecules and is therefore beneficial for use in some contexts of the present invention. In addition, when self-assembled on a substrate, PEG chains typically interact therebetween via hydrogen bonds, so as to produce a well-ordered monolayered film.

The polyethylene glycol residue in the compounds of the present invention can be derived from PEGs having a molecular weight that ranges from about 400 grams/mol and about 10000 grams/mol. Preferred PEGs are those having a molecular weight that ranges from about 2000 grams/mol and about 5000 grams/mol. Such PEGs allow the productions of a monolayered film when deposited on a solid surface in the presence of a functionalized group, as described hereinabove.

The polyethylene glycol residue may be substituted or unsubstituted and can be represented by the general Formula II below:

—(CR$^1$R$^2$CR$^3$R$^4$O)$_n$—            Formula II wherein n is an integer from 10 to 200; and R$^1$, R$^2$, R$^3$ and R$^4$ are each independently selected from the group consisting of hydrogen, alkyl, cycloalkyl, aryl, alkenyl alkynyl, alkoxy, thioalkoxy, aryloxy and thioaryloxy.

In a preferred embodiment, the PEG is unsubstituted such that R$^1$, R$^2$, R$^3$ and R$^4$ are each hydrogen.

In another preferred embodiment, the PEG residue is a medium-sized residue such that n is an integer from 60 to 100.

The polymer is preferably attached to the functionalized group described above via a linking moiety.

Exemplary linking moieties include, without limitation, oxygen, sulfur, amine, amide, carboxylate, carbamate, sulphonate, sulphonamide, phosphate, hydrazine, hydrazide, as these terms are defined herein and derivatives thereof.

In a representative example the linking moiety is an amide, formed between a carboxylic end group of the polymer and an amine end group of the functionalized moiety, as is detailed herein under.

The compounds of the present invention, by comprising the functionalized group and the polymer described hereinabove, readily form self-assembled monolayers when contacted with a substrate, in a one-step, simple to perform, reaction.

As the polymer residue in the compounds of the present invention further has a photoactivatable group attached thereto, each of the formed monolayers has a photoactivatable group attached thereto.

As used herein, the phrase "photoactivatable group" describes a group that is rendered active when exposed to photoactivation, namely when exposed to light. Photoactivatable groups typically comprise a protected reactive group, which upon exposure to light are de-protected, so as to generate a reactive group.

As used herein, the phrase "reactive group" describes a chemical moiety that is capable of interacting with another moiety. This interaction typically results in a bond formation between these moieties, whereby the bond can be, for example a covalent bond, a hydrogen bond, a coordinative bond, or an ionic bond.

Representative examples of reactive groups include, without limitation, amine, hydroxy, thiohydroxy, halo, alkoxy, thioalkoxy, aryloxy, thioaryloxy, carboxylate, phosphate, phosphonate, sulfate and sulfonate, as these terms are defined herein.

Depending on the intended use of the compound, the photoactivatable group is selected so as to generate a desired reactive group Thus, for example, a photoactivatable group that comprises a carbamate can generate upon exposure to light amine as the reactive group.

The photoactivatable groups according to the present invention are preferably derived from photoactivatable compounds and therefore preferably include a residue of, for example, photoactivatable compounds that has light-absorbing characteristics such as 6-nitrovertaryl chloroformate, 6-nitrovertaryl carbonyl, 2-nitrotoluene, 2-nitroaniline, phenacyl, phenoxy, azidoaryl, sulfonic ester, desyl, p-hydroxyphenacyl, 7-methoxy coumarin, o-ethylacetophenone, 3,5-dimethylphenacyl, dimethyl dimethoxybenzyloxy carbonyl, 5-bromo-7-nitroindolinyl, o-hydroxy-α-methyl cinnamoyl and 2-oxymethylene anthraquinone.

When exposed to light such as, for example, UV, IR, or visible light or a monochromatic light of a predetermined wavelength, reactive groups, which are capable of nucleic acids, as is detailed hereinunder, are generated.

The above-described compounds can be readily prepared using a simple two-steps synthesis. A process of preparing the compounds is described in details in PCT Application No. WO2006/064505 to the present inventor.

As discussed hereinabove, the substrate and the compound of the present invention are selected such that upon contacting the polymer with the substrate, a self-assembled monolayered film of the polymer forms on the substrate surface, in a one-step reaction.

The contacting procedure is preferably effected by incubating the compound of the present invention with the selected substrate, preferably in the presence of an organic solvent such as, for example, toluene.

Once a monolayered film of the polymer is deposited on the substrate surface, the reactive group for binding a screenable moiety can be generated by exposing a preselected area of the substrate to light.

Depending on the selected photoactivatable group and the active wavelength in which it is active, the light can be a UV, IR or visible light, or, optionally and preferably, the light can be a monochromatic light of a predetermined wavelength.

Exposure of a limited area of the substrate to light is preferably effected using a photo mask to illuminate selected regions the substrate and avoid coating the substrate at the periphery. However, other techniques may also be used. For example, the substrate may be translated under a modulated laser or diode light source. Such techniques are discussed in, for example, U.S. Pat. No. 4,719,615 (Feyrer et al.), which is incorporated herein by reference. In alternative embodiments a laser galvanometric scanner is utilized. In other embodiments, the synthesis may take place on or in contact with a conventional liquid crystal (referred to herein as a "light valve") or fiber optic light sources. By appropriately modulating liquid crystals, light may be selectively controlled so as to permit light to contact selected regions of the substrate. Alternatively, synthesis may take place on the end of a series of optical fibers to which light is selectively applied. Other means of controlling the location of light exposure will be apparent to those of skill in the art.

The substrate may be irradiated either in contact or not in contact with a solution and is, preferably, irradiated in contact with a solution. The solution may contain reagents to prevent the by-products formed by irradiation. Such by-products might include, for example, carbon dioxide, nitrosocarbonyl compounds, styrene derivatives, indole derivatives, and products of their photochemical reactions. Alternatively, the solution may contain reagents used to match the index of refraction of the substrate. Reagents added to the solution may further include, for example, acidic or basic buffers, thiols, substituted hydrazines and hydroxylamines, or reducing agents (e.g., NADH).

In an exemplary embodiment, exposing the substrate to light is effected so as to provide a patterned substrate in which reactive groups are generated according to a preselected pattern. The pattern can be printed directly onto the substrate or, alternatively, a "lift off" technique can be utilized. In the lift off technique, a patterned resist is laid onto the substrate or onto the light source. Resists are known to those of skill in the art. See, for example, Kleinfield et al., J. Neurosci. 8:4098-120 (1998). In some embodiments, following removal of the resist, a second pattern is printed onto the substrate on those areas initially covered by the resist; a process that can be repeated any selected number of times with different components to produce an array having a desired format.

Once the reactive group is generated the device is preferably sealed using methods which are well known in the art. Low fluorescence adhesives which provide sealing and cover constructions are preferably used. Such adhesives are dimensionally stable and do not flow into microfluidic channels. They adhere to the cover layer without creating voids or gaps that may allow migration of components from one path to adjacent path, and they exhibit good stability to moisture and temperature change. Adhesives used in accordance with the present invention can be either flexible or rigid, but should preferably be clear and colorless (such adhesives can be obtained from Adhesives Research Inc.). Other adhesives include, but are not limited to, pressure sensitive adhesives, such as ethylene-containing polymers, urethane polymers, butyl rubber, butadiene-acrylonitrile polymers, butadiene-acrylonitrile-isoprene polymers, and the like. See, for example, U.S. Pat. No. 5,908,695 and references cited therein.

Binding the nucleic acid can be effected by directly attaching the moiety to the reactive group.

Alternatively, binding the nucleic acid is effected via a mediating moiety. As used herein, the phrase "mediating moiety" describes a mediating agent or a plurality of mediating agents being linked therebetween that may bind to both the reactive group and the screenable moiety and thus mediate the binding of the nucleic acid to the reactive group.

The mediating moiety can thus be a bifunctional moiety, having two reactive groups, each independently capable of reacting with the reactive group attached to the substrate or the screenable moiety. Alternatively, the mediating moiety can comprise two or more moieties, whereby the first moiety can be attached to the reactive group and to a second mediating moiety, whereby the second mediating moiety can bind the nucleic acid.

Optionally and preferably, the mediating moiety comprises an affinity pair, such as, for example, the biotin-avidin affinity pair. The biotin-avidin affinity pair is highly useful for integrating nucleic acids on the substrate.

Alternatively, the mediating moiety can comprise biotin. When attached to the reactive group, biotin can bind a variety of chemical and biological substances that are capable of reacting with the free carboxylic group thereof.

According to aspects of the present invention, the sequence of at least one of the isolated nucleic acids which is attached to the reaction unit (or portion thereof) encodes a promoter which is operatively linked to a nucleic acid sequence encoding a polypeptide.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter.

A "constitutive" promoter is a promoter that is active under most environmental and developmental conditions. An example of a constitutive promoter is cytomegalovirus (CMV) or Rous sarcoma virus (RSV) promoter.

An "inducible" promoter is a promoter that is active under environmental or developmental regulation.

Examples of inducible promoters include the tetracycline-inducible promoter (Srour, M. A., et al., 2003. Thromb. Haemost. 90: 398-405), an IPTG inducible promoter, P70, P70$_b$, P$_{28}$, P$_{38}$ or Plac\arac (P$_{la}$).

In the isolated nucleic acid, the promoter is preferably positioned approximately the same distance from the heterologous transcription start site as it is from the transcription start site in its natural setting. As is known in the art, however, some variation in this distance can be accommodated without loss of promoter function.

A DNA segment such as an expression control sequence is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a pre-protein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters, linkers, or PCR fragments by means know in the art.

According to one embodiment, the promoter is a eukaryotic promoter.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

According to another embodiment, the promoter is a prokaryotic promoter.

According to yet another embodiment, the promoter is a plant-specific promoter.

According to still another embodiment, the promoter is a tissue specific promoter.

The nucleic acid of this aspect of the present invention may further comprise an enhancer element. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences may also be present in the nucleic acids in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

The nucleic acid of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

In the nucleic acid molecule of the invention, the coding sequence for the polypeptide is further preferably operably linked to a translational initiator sequence. In eukaryotes, the nucleotide consensus sequence (6-12 nucleotides) before the initiator ATG-codon is often called Kozak consensus sequence due to the initial work on this topic (Kozak, M. (1987): an analysis of 5'-noncoding sequences from 699 vertebrate messenger RNAs. Nucl. Acid Res. 15(20): 8125-47). The original Kozak consensus sequence CCCGCCGC-CrCC(ATG)G (SEQ ID NO: 1), including a +4 nucleotide derived by Kozak is associated with the initiation of translation in higher eukaryotes. For prokaryote host cells the corresponding Shine-Delgarno sequence (AGGAGG—SEQ ID NO: 2) is preferably present in the 5'-untranslated region of prokaryotic mRNAs to serve as a translational start site for ribosomes.

In the context of this invention, the term "translational initiator sequence" is defined as the ten nucleotides immediately upstream of the initiator or start codon of the open reading frame of a DNA sequence coding for a polypeptide. The initiator or start codon encodes for the amino acid methionine. The initiator codon is typically ATG, but may also be any functional start codon such as GTG, TTG or CTG.

According to a particular embodiment, the nucleic acid of the present invention encodes an operon.

It will be appreciated that the individual elements comprised in the nucleic acid can be arranged in a variety of configurations. For example, enhancer elements, promoters and the like, and even the polynucleotide sequence(s) encoding the polypeptide can be arranged in a "head-to-tail" configuration, may be present as an inverted complement, or in a complementary configuration, as an anti-parallel strand. While such variety of configuration is more likely to occur with non-coding elements of the nucleic acid, alternative configurations of the coding sequence within the nucleic acid are also envisioned.

In a particularly preferred embodiment of the invention, the nucleic acid molecule comprises a coding sequence coding for a predetermined amino acid sequence that is to be expressed.

Polypeptides encoded by the nucleic acids of the present invention can include, but are not limited to cytokines, chemokines, lymphokines, ligands, receptors, hormones, enzymes, antibodies and antibody fragments, and growth factors. Non-limiting examples of receptors include TNF type I receptor, IL-1 receptor type II, IL-1 receptor antagonist, IL-4 receptor and any chemically or genetically modified soluble receptors. Examples of enzymes include acetlycholinesterase, lactase, activated protein C, factor VII, collagenase (e.g., marketed by Advance Biofactures Corporation under the name Santyl); agalsidase-beta (e.g., marketed by Genzyme under the name Fabrazyme); dornase-alpha (e.g., marketed by Genentech under the name Pulmozyme); alteplase (e.g., marketed by Genentech under the name Activase); pegylated-asparaginase (e.g., marketed by Enzon under the name Oncaspar); asparaginase (e.g., marketed by Merck under the name Elspar); and imiglucerase (e.g., marketed by Genzyme under the name Ceredase). Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-beta), interferon gamma (IFNgamma), interferon gamma inducing factor I (IGIF), transforming growth factor beta (IGF-beta), RANTES (regulated upon activation, normal T-cell expressed and presumably secreted), macrophage inflammatory proteins (e.g., MIP-1-alpha and MIP-1-beta), Leishmnania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF alpha type II receptor, erythropoietin (EPO), insulin and soluble glycoproteins e.g., gp120 and gp160 glycoproteins. The gp120 glycoprotein is a human immunodeficiency virus (WIV) envelope protein, and the gp160 glycoprotein is a known precursor to the gp120 glycoprotein. Other examples include secretin, nesiritide (human B-type natriuretic peptide (hBNP)) and GYP-I.

Other heterologous products may include GPCRs, including, but not limited to Class A Rhodopsin like receptors such as Muscatinic (Muse.) acetylcholine Vertebrate type 1, Musc. acetylcholine Vertebrate type 2, Musc. acetylcholine Vertebrate type 3, Musc. acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykffin, C5a anaphylatoxin, Finet-leu-phe, APJ like, Interleukin-8 type A, Interleukin-8 type B, Interleukin-8 type others, C-C Chemokine type 1 through type 11 and other types, C—X—C Chemokine (types 2 through 6 and others), C—X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR10), Neuropeptide Y (type 1 through 7), Neuropeptide Y, Neuropeptide Y other, Neurotensin, Opioid (type D, K, M, X), Somatostatin (type 1 through 5), Tachykinin (Substance P(NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF, QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory 11 fam 1 through 13), Prostaglandin (prostaglandin E2 subtype EP 1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,11 GPR91, Purinoceptor P2RY5,8,9,10 GPR35,92,174, Purinoceptor P2RY12-14 GPR87 (JDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas proto-oncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRC5, Orphan GPCR6, Bride of sevenless proteins (BOSS), Taste receptors (TiR), Class D Fungal pheromone, Fungal pheromone A-Factor like (STE2,STE3), Fungal pheromone B like (BAR,BBR,RCB,PRA), Class E cAMP receptors, Ocular albinism proteins, Frizzled/Smoothened family, frizzled Group A (Fz 1&2&4&5&7-9), frizzled Group B (Fz 3 & 6), fizzled Group C (other), Vomeronasal receptors, Nematode chemoreceptors, Insect odorant receptors, and Class Z Archaeal/bacterial/fungal opsins.

Bioactive peptides may also be produced by the heterologous sequences of the present invention. Examples include: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleulin, denileukin diftitox, interferon alfa-n3 (injection), interferon alfa-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphnmate, octocog alfa, Factor VIII, palifermin, Indikinase, tenecteplase, alteplase, pamiteplase, reteplase, nateplase, monteplase, follitropin alfa, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alfa, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10(autoimmune iseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMA-TRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In certain embodiments, the polypeptide is an enzyme or biologically active fragments thereof. Suitable enzymes include but are not limited to: oxidoreductases, transferases, hydrolases, lyases, isomerases, and ligases. In certain embodiments, the heterologously produced protein is an enzyme of Enzyme Commission (EC) class 1, for example an enzyme from any of EC 1.1 through 1.21, or 1.97. The enzyme can also be an enzyme from EC class 2, 3, 4, 5, or 6. For example, the enzyme can be selected from any of EC 2.1 through 2.9, EC 3.1 to 3.13, EC 4.1 to 4.6, EC 4.99, EC 5.1 to 5.11, EC 5.99, or EC 6.1-6.6.

As used herein, the term "antibody" refers to a substantially intact antibody molecule.

As used herein, the phrase "antibody fragment" refers to a functional fragment of an antibody (such as Fab, F(ab')2, Fv or single domain molecules such as VH and VL) that is capable of binding to an epitope of an antigen.

According to one embodiment, at least one of the nucleic acids attached to the reaction unit encodes a transcription factor, an activator or a repressor. Particular examples of such are provided in Table 2 in the Examples section herein below.

According to another embodiment, at least one of the nucleic acids attached to the reaction unit encodes a polypeptide comprising a detectable moiety.

According to still another embodiment, the polypeptides are fluorescent polypeptides. Examples of such include, but are not limited to green fluorescent protein from *Aequorea victoria* ("GFP"), the yellow fluorescent protein and the red fluorescent protein and their variants (e.g., Evrogen).

According to still another embodiment, the polypeptides are phosphorescent polypeptides, chemiluminescent polypeptides or luminescent polypeptides.

Table 1 provides non-limiting examples of such detectable moieties contemplated by the present invention.

TABLE 1

| Identifiable Moiety | Amino Acid sequence (GenBank Accession No.)/ SEQ ID NO: | Nucleic Acid sequence (GenBank Accession No.)/SEQ ID NO: |
| --- | --- | --- |
| Green Fluorescent protein | AAL33912/3 | AF435427/12 |
| Alkaline phosphatase | AAK73766/4 | AY042185/13 |
| Peroxidase | CAA00083/5 | A00740/14 |
| Histidine tag | Amino acids 264-269 of GenBank Accession No. AAK09208/6 | Nucleotides 790-807 of GenBank Accession No. AF329457/15 |
| Myc tag | Amino acids 273-283 of GenBank Accession No. AAK09208/7 | Nucleotides 817-849 of GenBank Accession No. AF329457/16 |
| Biotin lygase tag | LHHILDAQKMVWNHR/8 | |
| orange fluorescent protein | AAL33917/9 | AF435432/17 |
| Beta galactosidase | ACH42114/10 | EU626139/18 |
| Streptavidin | AAM49066/11 | AF283893/19 |

It will be appreciated that a single reaction unit may be attached to isolated nucleic acids each having the same sequence. Alternatively, a single reaction unit may be attached to a plurality of isolated nucleic acids having different sequences. For example, a single reaction unit may be attached to a plurality of isolated nucleic acids encoding a transcriptome.

When the device comprises more than one test chamber, the present invention further contemplates attaching nucleic acids having a first sequence to the first test chamber and nucleic acids having a second sequence to the second test chamber—see for example FIGS. 3A-B.

Systems which comprise the device of the present invention may comprise a variety of different detection modalities at essentially any location on the microfluidic device. Detection can be achieved using detectors that are incorporated into the device or that are separate from the device but aligned with the region of the device to be detected.

A number of different detection strategies can be utilized with the microfluidic devices that are provided herein. Selection of the appropriate system is informed in part on the type of detectable moiety present in the expressed polypeptide. The detectors can be designed to detect a number of different signal types including, but not limited to, signals from fluorophores, chromophores, polypeptides that emit chemiluminescence, electrochemically active polypeptides, enzymes, cofactors, enzymes and enzyme substrates.

Illustrative detection methodologies suitable for use with the present microfluidic devices include, but are not limited to, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

Detection occurs at a "detection section," or "detection region", namely at the reaction unit where the polypeptide is being expressed. The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by an optical detector. The optical detector can include one or more photodiodes (e.g., avalanche photodiodes), a fiber-optic light guide leading, for example, to a photomultiplier tube, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. Alternatively, scanning systems can be used. For instance, certain automated systems scan the light source relative to the microfluidic device; other systems scan the emitted light over a detector, or include a multichannel detector. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

The detector can include a light source for stimulating a reporter that generates a detectable signal. The type of light source utilized depends in part on the nature of the reporter being activated. Suitable light sources include, but are not limited to, lasers, laser diodes and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions). A number of commercially-available external detectors can be utilized. Many of these are fluorescent detectors because of the ease in preparing fluorescently labeled reagents. Specific examples of detectors that are available include, but are not limited to, Applied Precision ArrayWoRx (Applied Precision, Issaquah, Wash.)).

The microfluidic device described herein can be used as a device for analyzing expression of proteins.

Thus, according to another aspect of the present invention there is provided a method of expressing a polypeptide comprising contacting the isolated nucleic acid of the microfluidic device described herein with a composition which comprises enzymes for performing expression of the polypeptide from said isolated nucleic acid, under conditions that allow expression of the polypeptide, thereby expressing the polypeptide.

Selection of the design of a particular microfluidic device for expressing a polypeptide is dependent upon the regulatory elements in the isolated nucleic acid attached to the substrate. The present inventors have shown that gene expression dynamics (e.g. time scale and protein levels) are controlled by the geometrical arrangement of compartments and channels in the biochip. For example the present inventors have shown that the oscillation period of a genetic network is controlled by the channel length.

The composition which comprises enzymes for performing expression is typically flowed through the flow chamber. The enzymes then diffuse through the microchannel and reach the nucleic acids which are attached to the test chamber.

Minimal enzymes required to achieve expression of proteins include RNA polymerase, ribosome and aminoacyl tRNA synthetase.

The present invention contemplates addition of these individual enzymes to the composition. Alternatively, the present invention considers use of cell extracts which naturally comprise enzymes for performing expression. An advantage of using a cell extract is that it typically comprises many other factors required to bring about expression of polypeptides. Typically, selection of the cell type from which the extract is prepared is dependent upon the source of the nucleic acids. Thus, for example, if a bacterial promoter sequence is included in the isolated nucleic acid, then a bacterial cell extract should be used.

Additional agents that may be added to the composition include for example dNTPs (ATP, GTP, CTP and UTP), tRNA, coenzyme A, NAD, cAMP, folinic acid, spermidine, agents for energy regeneration such as 3-phosphoglyceric acid or ATPase, DTT, amino acids, Mg-glutamate and K-glutamate.

For eukaryotic systems exemplary agents include RNA polymerase (I) and (II), aminoacyl tRNA synthetase, ribosomes, Initiation+elongation+release factors and energy regeneration enzymes.

In addition, agents may be added to the composition which inhibit the degradation of linear DNA such as the protein GamS.

Additional agents may be selected according to the nucleic acid sequence attached to the substrate. For example, in one embodiment arabinose is added in order to activate an AraC protein dimer.

An exemplary method of preparing a composition that may be used according to this aspect of the present invention is described herein below. The liquid part of the cell (cytoplasm) is extracted by breaking the cells. Membranes and insoluble debris are removed by centrifugation. During extract preparation, the endogenous DNA and mRNA may be removed. The extract may be filtered using a 10 kDa molecular weight cut-off filter. Final protein concentration is typically in the order of 1-100 mg/ml, more preferably 1-20 mg/ml, for example 10 mg/ml.

The device of the present invention enables gene expression from the DNA to continue indefinitely, without replacing the genetic material. Nutrients and enzymes are replenished through diffusion. Thus, the expressing may be effected for 2 hours, 4 hours, 6 hours 8 hours, 12 hours, 24 hours or longer.

Long-term expression of proteins allows proteins to reach steady state levels by continuous synthesis and continuous dilution (by diffusion of synthesized proteins through the microchannels and to the flow channel). The device allows visualization in real-time (during expression), binding of in-situ synthesized regulatory proteins to the DNA.

The present invention contemplates a myriad of application for the device described herein, some of which are detailed herein below.

1. A biochip platform for research and development in areas such as systems and synthetic biology, biomedical diagnostics, high-throughput screening, protein expression system;

2. Biological assays in the context of gene expression in spatially defined on-chip reactor systems;

3. A biochip reactor platform for large-scale biosynthesis of molecules (proteins, RNA, peptides, hormones, etc.) with medical applications (e.g. Insulin) based on enzymatic reactions which are currently carried out in bacteria/plants;

4. A platform for embedding schemes of molecular computation in spatially arranged reactors on the chip; and 5. High-throughput analysis of protein functionality resulting from genetic mutations/variations. For example, after mutations/variations in a human genome have been detected, our chip could analyze whether this mutations lead to functionality loss of the expressed protein.

The following describes a simple configuration of the microfluidic devices of the present invention, which can be utilized to analyze gene expression. It should be understood that this configuration is exemplary and that modifications thereof will be apparent to those skilled in the art.

Thus, FIG. 21 is a schematic illustration of a top view of a microfluidic, according to various exemplary embodiments of the present invention. In a simple configuration, microfluidic device 10 comprises a reaction unit 16, which comprises a test chamber 12 and a microchannel 14. Nucleic acids 18 are connected to the test chamber 12. The microchannel 14 is in communication with the flow-through channel 20.

Device 10 can also comprise an inlet port 26 which is in fluid communication with an external reagent inlet reservoir 22 such as by tubing (such as for infusing the screenable moiety) and an outlet port 28 which optionally may be in fluid communication with an outlet reservoir 30.

FIG. 22 is a schematic illustration of a top view of a microfluidic device 100, according to various exemplary embodiments of the present invention. In a simple configuration, microfluidic device 100 comprises 3 reaction units 108, each comprising a test chamber 104 and a microchannel 106. Nucleic acids 102 are connected to the test chamber 104.

It will be appreciated that the device may comprise additional reaction units as described herein above. Optionally, the reaction units of each test chamber are connected via a microchannel and further described herein above. Optionally, the reaction unit comprises more than one test chamber as described herein above. Optionally, each of the microchannels 106 are of different length, as further described herein above.

Microchannels 106 are in communication with the flow-through channel 114.

Device 100 can also comprise an inlet port 112 which is in fluid communication with an external reagent inlet reservoir 110 such as by tubing (such as for infusing the screenable moiety) and an outlet port which optionally may be in fluid communication with an outlet reservoir 120.

Fluids may be passively or actively infused into the flow channels such as by capillary forces or pump 116 (e.g., external pumps, e.g., peristaltic pumps or electro-osmotically pumps). The device may be covered by a solid cover layer 122.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

DNA Constructs

DNA parts used in this work are described in Table 1 herein below. Their assembly into single gene constructs and two gene networks are described in Tables 3 and 4, respectively as well as in FIGS. 8A-D. All the plasmids were constructed from the pBEST-Luc plasmid (Promega), with the UTR1 (untranslated region), except for the pBAD plasmid (araBAD promoter).

TABLE 2

| Promoter | Description | Reference |
|---|---|---|
| $P_{70}$ | Lambda phage promoter OR2-OR1-Pr specific to E. coli $\sigma^{70}$. Repressed by cI at high affinity and Cro with low affinity. | (18) |
| $P_{70b}$ | Promoter of the Lambda Cro repressor with the operator OR3 specific to E. coli $\sigma^{70}$. Repressed by Cro. | This work |
| $P_{28}$ | Promoter of the tar gene (E. coli) specific to $\sigma^{28}$ | (19) |
| $P_{38}$ | Promoter of the osmY gene (E. coli) specific to $\sigma^{38}$ | (19) |
| Plac\arac ($P_{la}$) | The hybrid promoter pLlacO-1 | (20) |
| Untranslated region | | |
| UTR1 | The untranslated region containing the T7 g10 leader sequence for highly efficient translation initiation | (19) |
| Transcription terminator | | |
| T500 | Transcription terminator for E. coli RNA polymerase | (19) |
| Gene | | |
| GFP | The enhanced green fluorescent protein truncated and modified in N- and C-termini. | (19) |
| $\sigma^{28}$ | rpoF (E. coli $\sigma^{28}$) | (19) |
| $\sigma^{38}$ | rpoS (E. coli $\sigma^{38}$) | (19) |
| CI | Lambda phage repressor protein CI | (19) |
| CRO | Lambda phage repressor protein Cro | (19) |
| diCro-GFP | Triple fusion protein Cro-Cro-GFP | This work |
| araC | AraC protein with ssra degradation tag | (20) |
| yemGFP | Monomeric yeast-enhanced green fluorescent protein with ssrA degradation tag | (20) |

TABLE 3

| Construct | Description | FIG. |
|---|---|---|
| unregulated | $P_{70}$-deGFP | FIG. 1C, FIG. 2A, FIG. 4A-C, FIG. 9A-C, FIG. 12A, FIGS. 13A-D, FIG. 17A FIGS. 20C-d |
| positive feedback | $P_{la}$-araC-$P_{la}$-yemGFP | FIG. 1D, FIG. 2B, FIG. 12B |
| negative feedback | $P_{la}$-Dicro-deGFP | FIG. 1F, FIG. 2C, FIG. 14 |

TABLE 4

Figures 16A, 16B, 16C, 16D, 16E:
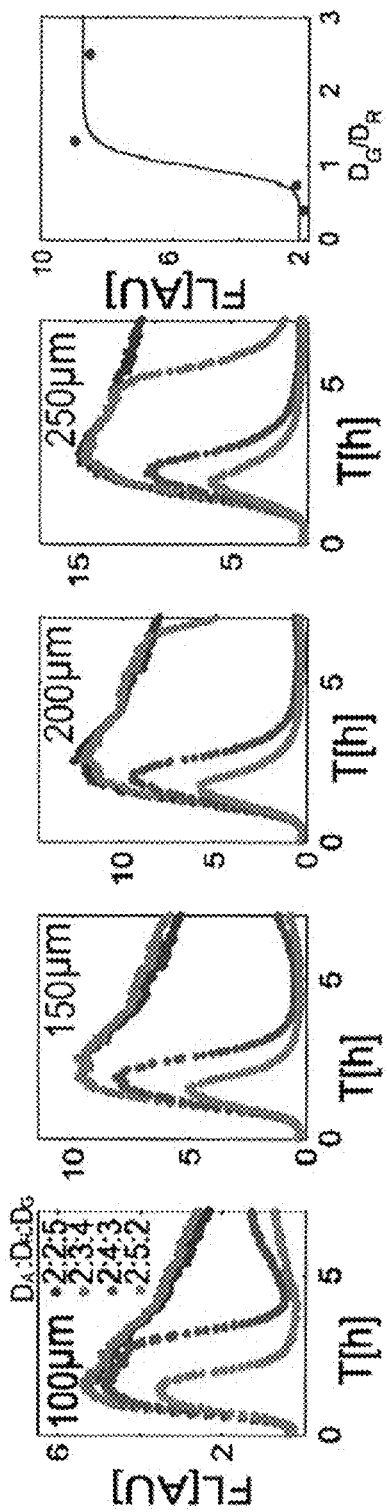

| | Description | | DNA Stoichiometry | |
|---|---|---|---|---|
| Network 1 | Appearing in | | FIG. 2E, FIGS. 16A-E | FIG. 10A-E |
| | Activator | $P_{70}$-$\sigma^{38}$ | 2 | Color coded in Figure |
| | Repressor | $P_{38}$-CI | 2 | |
| | Reporter | $P_{70}$-deGFP | 5 | |
| Network 2 | Appearing in | | FIG. 1E, FIG. 2D, FIG. 16B | |
| | Activator | $P_{70}$-$\sigma^{28}$ | 2 | |
| | Repressor | $P_{28}$-CI | 1 | |
| | Reporter | $P_{28}$-deGFP | 2 | |
| Network 3 | Appearing in | | FIG. 16C | |
| | Activator | $P_{70}$-$\sigma^{28}$ | 1 | |
| | Repressor | $P_{28}$-CI | 1 | |
| | Reporter | $P_{70}$-deGFP | 3 | |
| Network 4 | Appearing in | | FIG. 12C, FIG. 16D | |
| | Activator | $P_{70}$-$\sigma^{28}$ | 1 | |
| | Repressor 1 | $P_{28}$-CI | 1 | |
| | Repressor 2 | $P_{28}$-CRO | 1 | |
| | Reporter | $P_{28}$-deGFP | 1 | |
| Network 5 | Appearing in | | FIG. 15E | |
| | Activator | $P_{70}$-$\sigma^{28}$ | 1 | |
| | Repressor 1 | $P_{28}$-CI | 1 | |
| | Repressor 2 | $P_{28}$-CRO | 1 | |
| | Reporter | $P_{70}$-deGFP | 3 | |

Biochip Preparation

Each step of the fabrication is detailed herein below and illustrated in FIGS. 6A-B.

Design of the Device

The device consisted of 84 circular wells (compartments), etched 2-3 µm deep into a silicon wafer (FIG. 5). Silicon wafers (5", 0.525 mm thickness, test grade, <100>, p-type, University Wafers, Boston, Mass.) were used as the substrates. Each compartment had a diameter of 100 µm and was connected through a 20 µm wide and 50-300 µm long capillary channel to a perpendicular flow channel, 30-40 µm deep and 300 µm wide. At one end of the flow channel there was an inlet—a circular chamber, etched 30-40 µm deep and 2 mm in diameter. At the other end, the flow channel was connected to a 100 µm serpentine that ends at an outlet—a circular chamber, etched 30-40 µm deep and 2 mm in diameter.

Step 1: Etching

Resist Coating

S1818 or S1813 photoresist (MicroChem, Newton, Mass.) was applied by a spin-coater (model PWM32, Headway Research Inc., Garland, Tex.) onto each wafer in a single step process: 2000 rpm for 40 sec with a ramp of 1000 rpm/s. The resists were pre-baked for 1 minute at 115°.

Lithography

Using a mask aligner (6 mW/cm², Karl Suss MA6/BA6, Garching, Germany), the samples were exposed for 40 seconds, through a polyester based photomask (CAD/Art Services Inc. Bandon, Oreg.). Each mask contained six devices.

Post Exposure Bake

The samples were post-developed for 40 sec in MF319 and rinsed with water. The resulting resist thickness was 1.8 µm for S1813 and 2.8 µm for S1818.

Reactive Ion Etching (RIE)

An Advanced Silicon Etch ICP-RIE (Surface Technology Systems, New Port, England) was used for etching. The 2 µm height features were etched using the following parameters for 40 seconds: pressure of 30 mT, SF6 flow rate of 130 sccm, $O_2$ flow rate of 13 sccm, power of 500 W applied to the 13.56 MHz RF coil and 100 W to the platen. For the 40

μm deep features a protocol based on the Bosch protocol (23) was used with an alternating passivation/etching process. Etching parameters were: pressure of 30 mT, SF6 flow rate of 130 sccm, $O_2$ flow rate of 13 sccm, power of 500 W applied to the RF coil and 100 W to the platen. Passivation parameters were: pressure of 30 mT, C4F8 flow rate of 30 sccm and a power of 500 W applied to the coil. Each step was 10 sec in duration and total etching process was 20 cycles.

After etching, the samples were rinsed in acetone and isopropanol to remove any remaining photoresist. A SEM image of the device is presented in FIG. 7A. The fabricated silicon wafers were cut into six devices, 24×48 mm² each, using a diamond-head scriber and manually breaking of the wafer.

Step 2: Inlet and Outlet Drilling

Holes were drilled to form an inlet and an outlet in the device. A bench drill machine (Proxxon, TBM 220) and a Dremel 7103 diamond wheel point drill were used. The holes were drilled through the circular etched inlet and outlet at the ends of the flow channel. The device was cleaned following drilling: boiled in ethanol at 70° C. for 10 minutes followed by sonication and cleaning with basic piranha solution ($H_2O_2$: $NH_3$: $H_2O$; 1:1:4, heated to 70° C. for 10 minutes) and dried using Argon.

Step 3: $SiO_2$ Coating

The device was coated with a ~50 nm $SiO_2$ layer deposited by low-temperature atomic layer deposition (FIJI F200, Cambridge Nanotech).

Step 4: Biocompatible Photoactivable Monolayer Assembly

The $SiO_2$ coated device was incubated with a polymer solution. The polymer was composed of a polyethylene glycol backbone with a Nvoc-protected amine at one end, and a trialkoxysilane function at the other end (16). The polymer concentration was 0.2 mg/ml in Toluene and the incubation process was 10-20 min during which a monolayer was formed on the surface. The incubation was followed by washing in Toluene and drying.

Step 5: Lithography Patterning

The lithography process was performed by placing the fabricated chip on a translational stage coupled to an inverted microscope (Zeiss Axiovert 200). UV light from fluorescent light source (EXFO X-Cite 120Q), was passed through a rectangular pinhole and a 365 nm band pass filter (Chroma) and focused on the substrate with a X60 objective. The exposure time was set to yield a total 2.5 Joule/cm² (16). The areas on the surface that were exposed to UV light were de-protected and an amine group was exposed.

Step 6: Biotin Coating.

Biotin N-hydroxysuccinimidyl ester (biotin-NHS) dissolved in a borate buffered saline (0.5 mg/ml) was incubated on the chip for 15 minutes. The biotin-NHS covalently bound to the exposed amine groups on the UV exposed monolayer. Thus, a surface patterned with biotin was obtained.

Step 7: DNA Deposition and Brush Assembly.

Linear DNA fragments were produced by polymerase chain reaction (PCR) with KAPA HiFi HotStart ReadyMix (KK2601, KAPA BIOSYSTEMS), using one primer with biotin and another with Alexa Fluor 647, both attached at the 5'-end (IDT). The biotin primer was located downstream to the transcription terminator. PCR products were cleaned twice using Promega Wizard® SV-Gel and PCR Clean-Up. DNA was conjugated to streptavidin (SA) by mixing in solution in a molar ratio of 1:1.5 DNA:SA. The final DNA solution contained SA conjugated DNA at a concentration of 100-300 nM in a phosphate buffered saline.

Nano-liter DNA-SA droplets were individually deposited onto the reactor chambers using the GIX Microplotter II (Sonoplot Inc., Middleton, Wis.) and 60 μm diameter micropipettes. The DNA-SA solutions were incubated on the device for an hour in a PBS buffer. During incubation the DNA formed a dense brush on the surface. The brush density was of the order of $10^3$ DNA μm$^{-2}$. The promoter orientation of the DNA was toward the surface of the brush. Finally, DNA brushes were localized to the UV patterned areas inside the etched compartments (FIG. 1A).

The device was then bathed in PBS and then in water to remove excess adsorbed DNA. The device was carefully removed from the water bath. The hydrophobicity of the monolayer coating left a dry surface, except where DNA brushes formed.

Step 8: Sealing the Device

The device front side (the fabricated side) was sealed with a PDMS coated coverslip and magnets. Magnets embedded in a punched PDMS were attached to the backside of the device (the untreated side of the device), aligned to the drilled inlet and outlet. At this point the device was dry.

Step 9: Flowing the Cell-Free Extract.

The device inlet was connected using microfluidic tubing to a reservoir of PBS cooled to 4° C. with a cooling circulator (Huber ministat). The outlet was connected to a diaphragm vacuum pump (vacuubrand, ME 2C, 1.9/2.2 m³/h, 80 mbar). The device was placed on a microscope, in an incubating chamber (30° C.). Once the pump was turned on, PBS washed through the tubing into the main flow channel and entered by capillary into the compartments within a couple of minutes. Air was pushed outside through the PDMS. The experiment began by replacing the PBS with cell extract, which then washed through the main flow channel at a rate of ~1 μl/min and diffused through the capillaries into DNA compartments. Constant flow was maintained during the experiment.

Imaging

The experiment was carried on a translational stage coupled to an inverted microscope (Zeiss Axiovert 200) with ANDOR Neo sCMOS camera (Andor Technology plc., Belfast, UK) and X10 Zeiss objective.

DNA Brush

Using the present photolithography approach, DNA-SA conjugates assembled on a pre-patterned biotin surface. The DNA bound to the surface at high densities to form DNA brushes.

Brush Properties

The DNA brush is a dense phase of DNA molecules that are anchored to the surface at one end. The density of surface binding sites is estimated $10^4$ μm$^{-2}$ and the final DNA brush density is at the order of $10^3$ μm$^{-2}$ such that the distance between DNA molecules is ~20 nm. At such proximity the charged DNA polymers experience electrostatic and excluded volume interactions, that can stretch the brush perpendicular to the surface (24). In water, the brush is fully extended to its contour length, due to osmotic pressure of counter ions that are trapped within the brush to maintain neutrality. In a buffered solution with ionic strength of ~150 mM, electrostatic interactions are screened out and a 1 kbp DNA brush attains a minimal height of ~100 nm. Thus, the effective DNA concentration in the brush is ~10 μM which is 3 orders of magnitude higher than the concentration that is typically used in cell-free reactions (bulk or vesicle).

Promoter Orientation

In the linear DNA constructs used in this work, the promoter was oriented towards the surface of the compartment. The gene size varied 300-1000 bp. The distance between the DNA top and the promoter is about 200 bp and a similar distance between the terminator and the DNA end attached to the surface. The effect of promoter orientation and surface proximity on transcription activity has been previously shown (5). There, it was observed that transcription activity is enhanced when the promoter is pointing towards the surface and located close to the surface (25).

The Endogenous *E. Coli* Cell-Free Extract

Overview

In this study a cell-extract that is a crude cytoplasmic extract from *E. Coli* strain BL21 Rosetta2 (Novagen) was used according to a procedure described previously (18). The cell-free reactions were composed of 33% (volume) crude extract and the other 66% (volume) of water, DNA and buffer with the following final composition: 50 mM HEPES pH 8, 1.5 mM ATP, 1.5 mM GTP, 0.9 mM CTP, 0.9 mM UTP, 0.2 mg/mL tRNA, 0.26 mM coenzyme A, 0.33 mM NAD, 0.75 mM cAMP, 0.068 mM folinic acid, 1 mM spermidine, 30 mM 3-phosphoglyceric acid, 2 mM DTT, 1.5 mM amino acids, 6.5 mM Mg-glutamate, 100 mM K-glutamate, and 2% PEG 8000.

Enzymes in the Cell-Extract

The extract contained the soluble proteins of *E. coli* (above 10 kDa molecular weight cut-off), with concentrations of 10 mg/ml in the final reaction, which was the optimum concentration for expression (18). The liquid part of the cell (cytoplasm) was extracted by breaking the cells. Membranes and insoluble debris were removed by centrifugation. During extract preparation, the endogenous DNA and mRNA were removed. The cell extract provided the transcription and the translation machineries necessary for gene expression. The transcription was driven by the endogenous *E. coli* RNA polymerase and thus allowed for the use of the entire repertoire of the *E. Coli* regulation toolbox (19). This was the major difference with standard extracts, which use bacteriophage RNA polymerases.

Nuclease and Protease Activity

The cell extract contained active proteases and ribonucleases. Previously, stability of proteins and mRNA were studied in the cell-free system (21, 26). Proteins without a degradation tag were stable with no observed degradation. Proteins with degradation tags, such as SsrA and YbaQ, were targeted to the ClpXp degradation complex and were degraded with a fast initial degradation rate of 10 nM/min but the degradation activity was lost after a degradation of ~0.5 μM in the cell extract. In contrast, mRNA exhibited a lifetime of about 10 minutes and was degraded by non-specific ribonucleases. The protein GamS, was added to all of the reactions in concentration of 3 μM to inhibit the degradation of linear DNA by the 3' exonuclease activity of the RecBCD complex (27) which was present in the cell-free system.

Energy Regeneration System

The cell-extract was supplemented with 3-phosphoglyceric acid (3-PGA) for ATP regeneration (18). The 3-PGA is a natural substrate to *E. Coli* and therefore no enzyme was added to the extract.

Arabinose Supplement

In experiments including the positive feedback construct, with the AraC promoter, 1.5% (W/V) final concentration of arabinose (A3256-L-(+)-Arabinose, Sigma) was added.

Calibration of GFP Concentration and Diffusion

GFP Concentration

In order to assess the GFP concentration expressed in the microfluidic chamber, a calibration measurement was performed. Recombinant purified GFP at different concentrations was continuously flowed through the main channel and diffused into the capillaries and finally into the compartment. The fluorescence in the compartment was measured as a function of GFP concentration (FIGS. 8A-D).

GFP Diffusion Coefficient

The present inventors evaluated GFP diffusion coefficient by pumping 1 μM of GFP through the main flow channel. GFP diffused through the capillary channels and into the chambers (FIGS. 8A-D). The diffusion coefficient D was calculated, $$D = \frac{L^2}{T_{GFP}} = 33.5 \pm 1 \frac{\mu m^2}{s}.$$

Here $T_{GFP}$ was the diffusion time of GFP, L was the length of the capillary channel.

Expression Dynamics Variation

The present inventors studied variation of expression dynamics between compartments within a single experiment, and between different experiments using the unregulated construct expressing GFP under a $P_{70}$ promoter (FIGS. 13A-D) and for the self-repressing construct (FIG. 14). The present inventors estimated the variation as the standard deviation of the relative difference between two compartments.

$$\% \text{ variation} = 100 \cdot std\left(\frac{\sqrt{(P_1 - P_2)^2}}{P_1}\right)$$

Here $P_1$, $P_2$ is GFP expression level in compartments 1 and 2 with the same characteristic geometrical parameters, and the standard deviation was taken over all time points in the same experiment. The variation between different experiments is 5-10%. The variation between compartments in the same experiment is less than 3%.

Protease Activity in the DNA Compartment

In principle, adding protein degradation tags may further shorten the lifetime of proteins in the compartment, leading to shorter time scales in the dynamics. However, targeting degradation of GFP fused to SsrA or YbaQ tags by the ClpXP complex endogenously present in the cell-free extract (21) showed no detectable difference in kinetics (FIGS. 17A-D).

Single Compartment Theory: The Effective Lifetime

The dynamics of proteins in the device is decoupled into (i) synthesis inside the compartment with a diffusive leak into the capillary, and (ii) one-dimensional diffusion along the capillary, $$\dot{p} = D\nabla^2 p.$$

Here D is the protein diffusion coefficient. We will assume an adiabatic approximation such that the diffusion dynamics along the capillary is slower than the protein dynamics in the compartment and therefore can be assumed at steady state, $$p(x,t) = p_R(t)(1-x/L),$$

$$\partial_x p(x,t) = -p_R(t)/L.$$

Here $P_R$ is the protein concentration in the compartment, where it is homogenous. There is a linear concentration profile along the capillary of length L, which reaches zero at the main channel, x=L (FIG. 5). The time scale for reaching linear gradient is $\tau_D = L^2/D \approx 5$ min.

The diffusion of proteins from the compartment into the capillary can be computed by writing the diffusion equation inside the two-dimensional compartment.

$$\partial_t p_R(r,t) = D\nabla^2 p_R(r,t) + a_{syn}.$$

The first term is the diffusion within the compartment and the second term is the protein synthesis rate per unit volume. We integrate this equation up to the compartment boundary r=R using gauss's law, $\int dv \nabla^2 p = \int ds\, \hat{n} \cdot \nabla p$, $$\partial_t p_R(t) = a_{syn} + \frac{D}{V} \int ds\, \hat{n} \cdot \nabla p_R(R,t).$$

Here $V = \pi R^2 h$ is the compartment volume. The boundary condition along the compartment walls is $\nabla P_R(R,t) = 0$, except for the compartment opening. The opening has width W and height h, and the protein gradient is along the capillary, $\int ds\, \hat{n} \cdot \nabla p_R(R,t) = hW \partial_x p_R$. We thus obtain, $$\partial_t p(t) = a_{syn} + \frac{DhW}{V} \partial_x p_R.$$

The gradient at the compartment opening is $\partial_x p_R = -p_R/L$ and thus, $$\partial_t p(t) = a_{syn} - \frac{DW}{\pi R^2 L} p_R.$$

We define the effective protein lifetime, $$\tau_R = \frac{V_R}{V_c} \tau_D = \frac{\pi R^2}{DW} L$$

and the protein dynamics inside the compartment is, $$\partial_t P_R = a_{syn} - p_R/\tau_R.$$

For diffusion coefficient, $D = 33\,\mu m^2/s$, and for the 300 μm long capillary, the protein life time is $\tau_R = 60$ min.

The steady state solution in the compartment is, $$p_R = a_{syn} \tau_R = a_{syn} \frac{\pi R^2 L}{DW}.$$

The gradient slope is independent of the capillary length, $$\partial_x p = -\frac{a_{syn} \tau_R}{L} = a_{syn} \frac{\pi R^2}{DW}.$$

Single Compartment Theory: Gene Expression Onset Time

In this section we derive an equation for the onset time of expression in the DNA compartments. We find that the onset time scales linearly with the capillary length, $t_{onset} \sim L$, as observed experimentally (FIG. 11).

The expression initiates once a minimal concentration $c_{onset}$ of the reaction components reaches the compartment. The diffusion of reaction components can be divided in two steps: i) Fast diffusion, $\tau_D = L^2/D$, along the one-dimensional capillary. ii) A slower regime determined by a time scale, $\tau_R$, which is similar to the protein lifetime described in the previous section. In this regime, the reaction components reach the two-dimensional compartment, and a linear concentration gradient forms between the flow channel where the concentration is maximal $c_{max}$ to the compartment where the concentration c(t) is initially zero, c(0)=0, and increases with time to $c = C_{max}$. Using Fick's law the flux of reaction components into the DNA compartment is, $$J\left[\frac{mol}{m^2 s}\right] = -D \frac{\partial c}{\partial x}.$$

Assuming a linear gradient between the compartment and the flow channel we find the kinetics of reaction components inside the compartment, $$\dot{c} = -\frac{c_{max} - c}{\tau},$$
$$c = c_{max}\left(1 - e^{-\frac{t}{\tau}}\right),$$
$$\tau = \frac{\pi R^2 L}{DW}.$$

We further assume that the minimal concentration for expression onset $c_{min}$ is smaller than the final concentration $C_{onset} < c_{max}$. We derive the onset time, $$c_{onset} = c_{max}\left(1 - e^{-\frac{t_{onset}}{\tau}}\right),$$
$$t_{onset} \approx \frac{c_{min}}{c_{max}} \tau \sim L.$$

Indeed, we find that the expected onset time is linear in the capillary length.

One-Dimensional Array of Connected Compartments: Expression and Diffusion

We consider a one-dimensional array of connected compartments (FIGS. 4A-F). In this case, proteins are synthesized in a single compartment and diffuse between compartments (x-axis) along capillaries with width $W_x$ and length $L_x$ (FIGS. 20A-D). In addition, the proteins diffuse in the y-axis out to the main channel, along capillaries with width $W_y$ and length $L_y$, which is the turnover mechanism described in the previous section. At steady state we expect the concentration within the compartments to be homogenous, and to have linear profiles along the capillaries and between compartments. The linear profiles are the steady-state solution to the one-dimensional diffusion equation along the capillaries.

In this section we use the above considerations to show that the steady-state profile of proteins along the one-dimensional array of compartments is exponentially decaying away from the protein source. The decaying profile has an exponential envelope, which is composed of small linear decays between compartments. Thus, at the length scale of a single compartment, we observe a linear decay. At larger scales, the observed decay is exponential. We find that the exponential decay length, $\lambda = \sqrt{D_{eff} \tau}$, can be expressed in terms of an effective diffusion coefficient, $D_{eff}$, and the lifetime of proteins in the compartment, $\tau$.

Notably, the decay length scales with the compartment geometry but is independent of the protein diffusion coefficient. This is because both the effective diffusion coefficient as well as the protein lifetime, result from the protein diffusion.

The flux of proteins from the compartment into the capillaries is, $$J\left[\frac{mol}{m^2 s}\right] = -D\frac{\partial p}{\partial x}$$

Assuming linear profiles along the capillaries, the flux of proteins into the capillaries in units of concentration per unit time is, $$\dot{p} = -\frac{DW}{\pi R^2 L}\Delta p = -\frac{\Delta p}{\tau}$$

We define two time scales for the diffusion along the x-axis, $$\tau_x = \frac{\pi R^2 L_x}{DW_x}$$

and for the diffusion along the y-axis, $$\tau_y = \frac{\pi R^2 L_y}{DW_y}$$

We consider the protein kinetics in compartment i. The proteins can diffuse to compartment i-1, to compartment, i+1, or to be depleted into the main channel. The kinetic equation is, $$\dot{p}_i = 1/\tau_x(p_{i-1}-p_i) + 1/\tau_x(p_{i+1}-p_i) - p_i/\tau_y$$

We obtained a discrete one-dimensional diffusion equation with effective diffusion constant $D_{Eff}=d^2/\tau_x$ and protein lifetime $\tau_y$. The distance between compartments is $d=R+L_x$.

$$\dot{p}_i = D\frac{p_{i-1}+p_{i+1}-2p_i}{d^2} - \frac{p_i}{\tau_y}$$

The steady-state solution is an exponential decay, $$p_i = p_1 e^{-(i-1)\frac{d}{\lambda}}$$

The exponential decay length is, $$\lambda = \frac{d}{\cosh^{-1}\left(\frac{d^2}{2D\tau_y}+1\right)}$$

The decay length is simplified in the limit where it is larger than the distance between compartments $d < \sqrt{D\tau_y}$ (the continuum limit), $$\lambda \approx \sqrt{D\tau_y} = d\sqrt{\frac{L_y W_x}{L_x W_y}},$$

The decay length scales with the distance between compartments and the square root of the ratio between geometrical parameters of the capillaries. Interestingly, the decay length is independent of the diffusion coefficient of the protein. Thus the same decaying length is expected for different proteins. In the experiment (FIGS. 4A-F) we find that the GFP profile along the x axis has an envelope of an exponentially decaying profile, with a decay length of $\lambda=380\pm40$ µm, while the exponential profile expected for this one-dimensional expression diffusion system with $L_x=100$ µm; $W_x=20$ µm; $L_y=150$ µm; $W_y=20$ µm, is $\lambda=280$ µm. The difference between the estimated theoretical value and the measured value of the decay length is reasonable given the array is composed only of 7 reactors whereas the theory considers an infinite array.

One-Dimensional Array of Connected Compartments: Flow Considerations

The flow in the microfluidic device is laminar. The capillary connecting the compartments is parallel to the main channel, and there is a pressure gradient between the first and last compartments. Thus, we expect a residual flow between compartments (FIGS. 20A-D). Here we show that our design minimizes the flow between the compartments and that the dominant transport between compartments is by diffusion.

The flow rate through the device in the 1D experiments was $Q \approx 0.3$ µl/min. The feeding channel was 900 µm wide and 100 µm deep with a cross section area $A_{main} \approx 10^5$ µm². Thus the velocity in the feeding channel was $v_{main} = Q/A \approx 50$ µm/s. The hydraulic resistance determines the ratio of velocities between the main channel and the capillary, $$\frac{v_{capillary}}{v_{main}} = \frac{R_{main}A_{main}}{R_{capillary}A_{capillary}} = \left(\frac{h_{capillary}}{h_{main}}\right)^2 \approx 10^{-4}.$$

Here we used the Poiseuille equation for hydrodynamic resistance in a rectangular cross section, $$R = \frac{12\eta L}{h^3 W}.$$

The liquid viscosity is $\eta$. Thus, the velocity in the capillary connecting the compartments is $v_{capillary}=5\cdot10^{-3}$ µm/s.

We compare the transport distance by flow and diffusion during the lifetime of proteins in the compartments, $\tau$ 60 min which was derived in previous sections:

$$L_{flow}=V_{capillary}\tau \approx 15 \text{ µM},$$

$$L_{Diffusion}=\sqrt{D_{eff}\tau} \approx 350 \text{ µm}.$$

Indeed we see that during the lifetime of proteins in the compartments, their transport by diffusion is dominant over the transport by flow, $L_{Diffusion} \gg L_{flow}$.

REFERENCES FOR MATERIALS AND METHODS SECTION

1. D. S. Tawfik, A. D. Griffiths, Man-made cell-like compartments for molecular evolution., *Nat. Biotechnol.* 16, 652-6 (1998).

2. V. Noireaux, A. Libchaber, A vesicle bioreactor as a step toward an artificial cell assembly., *Proc. Natl. Acad. Sci. U.S.A* 101, 17669-74 (2004).
3. V. Noireaux, R. Bar-Ziv, A. Libchaber, Principles of cell-free genetic circuit assembly., *Proc Natl Acad Sci USA* 100, 12672-12677 (2003).
4. J. Kim, K. S. White, E. Winfree, Construction of an in vitro bistable circuit from synthetic transcriptional switches., *Mol. Syst. Biol.* 2, 68 (2006).
5. E. Franco et al., Timing molecular motion and production with a synthetic transcriptional clock., *Proc. Natl. Acad. Sci. U.S.A* 108, E784-93 (2011).
6. A. J. Hockenberry, M. C. Jewett, Synthetic in vitro circuits., *Curr. Opin. Chem. Biol.* 16, 253-9 (2012).
7. M. Isalan, C. Lemerle, L. Serrano, Engineering gene networks to emulate *Drosophila* embryonic pattern formation., *PLoS Biol.* 3, e64 (2005).
8. D. Matthies et al., Cell-free expression and assembly of ATP synthase., *J. Mol. Biol.* 413, 593-603 (2011).
9. Y. Heyman, A. Buxboim, S. G. Wolf, S. S. Daube, R. H. Bar-Ziv, Cell-free protein synthesis and assembly on a biochip, *Nat. Nanotechnol.* 7, 374-378 (2012).
10. J. Shin, P. Jardine, V. Noireaux, Genome replication, synthesis, and assembly of the bacteriophage T7 in a single cell-free reaction., *ACS Synth. Biol.* 1, 408-13 (2012).
11. A. Spirin, V. Baranov, L. Ryabova, S. Ovodov, Y. Alakhov, A continuous cell-free translation system capable of producing polypeptides in high yield, *Science* 242, 1162-1164 (1988).
12. T. Thorsen, S. J. Maerkl, S. R. Quake, Microfluidic large-scale integration., *Science* 298, 580-4 (2002).
13. D. Gerber, S. J. Maerkl, S. R. Quake, An in vitro microfluidic approach to generating protein-interaction networks., *Nat. Methods* 6, 71-4 (2009).
14. H. Niederholtmeyer, V. Stepanova, S. J. Maerkl, Implementation of cell-free biological networks at steady state., *Proc. Natl. Acad. Sci. U.S.A* 110, 15985-90 (2013).
15. P. Müller, K. W. Rogers, S. R. Yu, M. Brand, A. F. Schier, Morphogen transport., *Development* 140, 1621-38 (2013).
16. A. Buxboim et al., A single-step photolithographic interface for cell-free gene expression and active biochips, *Small* 3, 500-10 (2007).
17. D. Bracha, E. Karzbrun, S. S. Daube, R. H. Bar-Ziv, Emergent Properties of Dense DNA Phases toward Artificial Biosystems on a Surface., *Acc. Chem. Res.* 47, 1912-1921 (2014).
18. J. Shin, V. Noireaux, Efficient cell-free expression with the endogenous *E. Coli* RNA polymerase and sigma factor 70., *J. Biol. Eng.* 4, 8 (2010).
19. J. Shin, V. Noireaux, An *E. coli* cell-free expression toolbox: application to synthetic gene circuits and artificial cells., *ACS Synth. Biol.* 1, 29-41 (2012).
20. J. Stricker et al., A fast, robust and tunable synthetic gene oscillator., *Nature* 456, 516-9 (2008).
21. J. Shin, V. Noireaux, Study of messenger RNA inactivation and protein degradation in an *Escherichia coli* cell-free expression system., *J. Biol. Eng.* 4, 9 (2010).
22. L. H. Hartwell, J. J. Hopfield, S. Leibler, A. W. Murray, From molecular to modular cell biology, *Nature* 402, C47-C52 (1999).
23. X. Wang, W. Zeng, G. Lu, O. L. Russo, E. Eisenbraun, High aspect ratio Bosch etching of sub-0.25 µm trenches for hyperintegration applications, *J. Vac. Sci. Technol. B Microelectron. Nanom. Struct.* 25, 1376 (2007).
24. D. Bracha, E. Karzbrun, G. Shemer, P. a Pincus, R. H. Bar-Ziv, Entropy-driven collective interactions in DNA brushes on a biochip., *Proc. Natl. Acad. Sci. U.S.A.* 110, 4534-8 (2013).
25. S. S. Daube, D. Bracha, A. Buxboim, R. H. Bar-Ziv, Compartmentalization by directional gene expression, *Proc. Natl. Acad. Sci. U.S.A* 107, 2836-41 (2010).
26. E. Karzbrun, J. Shin, R. H. Bar-Ziv, V. Noireaux, Coarse-Grained Dynamics of Protein Synthesis in a Cell-Free System, *Phys. Rev. Lett.* 106, 048104 (2011).
27. A. E. Karu, Y. Sakaki, H. Echols, S. Linn, The gamma protein specified by bacteriophage gamma. Structure and inhibitory activity for the recBC enzyme of *Escherichia coli*., *J. Biol. Chem.* 250, 7377-87 (1975).

Results

In the past decade cell-free gene expression reactions have been used to design synthetic biological systems including droplets for molecular evolution (1), a vesicle bioreactor toward an artificial cell (2), regulatory (3-6) and morphogenetic-like genetic circuits (7), as well as assembly of protein complexes (8-10). However, so far the lack of efficient protein turnover has prevented the emergence of expression dynamic patterns, such as oscillations, in a continuous expression bioreactor or vesicle (2, 11). Microfluidic chips containing switching valves and addressable fluidic chambers (12, 13) have succeeded to implement steady-state and dynamic protein synthesis reactions (14). However, micron-scale positional information encoded in diffusive concentration gradients of proteins and messenger RNA (mRNA), as in a morphogenetic scenario (15), is washed away in flow driven expression compartments.

Here, a solid-state biochip approach is presented for the assembly of an 'artificial cell', which enables protein turnover, materials exchange with the environment, a capacity to encode and express genes at high surface density within a controlled geometry, and maintain micron-scale positional information in diffusive molecular gradients.

Figure 1C:
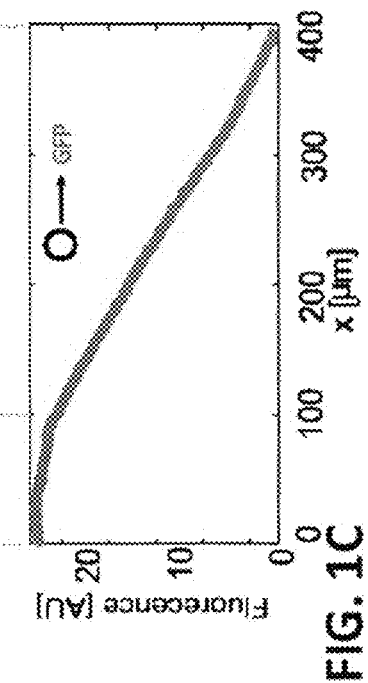

Dense phases of end-attached, linear double-stranded DNA templates (DNA brushes), were assembled by chemical photolithography (16, 17) on the surface of circular compartments carved in silicon with radius R=50 µm and depth h=1-3 µm (FIGS. 1A-B and FIGS. 5-7G). The DNA compartments were connected to a 30 µm deep flow channel through thin capillaries of width W=20 µm. The device was sealed, and *E. coli* cell extract (18, 19) was continuously flown in the main channel. Reaction components were transported by diffusion into the DNA compartment because of the high resistance to flow through the capillary (FIGS. 8A-D). Proteins were synthesized in the DNA compartment and diffused out to the flow channel through the capillary. A linear protein concentration gradient formed along the capillary, decaying from a maximal value in the DNA compartment where its distribution was homogenous, down to zero at the channel junction (FIG. 1C). The protein linear gradient persisted throughout the duration of expression, which reached a steady-state concentration (FIGS. 9A-C). The dilution through the capillary leads to an emergent effective protein lifetime, $$\tau = \frac{\pi R^2}{WD}L,$$

that is obtained by solving the diffusion equation in the compartment geometry, where D is the protein diffusion constant (see Materials and Methods section, herein above).

The effective protein lifetime enabled the present inventors to observe gene expression dynamics including steady-state (FIG. 1D) and oscillations (FIG. 1E). FIG. 1D shows expression of GFP through a positive feedback gene construct, which is self-activated by the AraC protein dimer in the presence of arabinose (20) (FIG. 10B). The kinetics was characterized by a sharp onset following a 2 hours delay, and reached a steady-state level for over 8 hours. To implement an oscillatory gene expression dynamics, an activator-repressor network with sigma factor $\sigma^{28}$ for activation and the lambda phage cI repressor (FIGS. 10D-E and Tables 1-3) was used. The network exhibited emergent oscillations for many hours with a period of ~2.5 hours (FIG. 1E). Furthermore, the high concentration of regulatory proteins near the DNA brush enabled direct imaging of transcription regulation. Repression of transcription was imaged using a negative-feedback construct that codes for a fusion of a Cro repressor dimer and GFP, expressed under a Cro-regulated promoter (FIG. 10C). The synthesized fusion protein binds the repressor site adjacent to the promoter, thereby localizing the GFP signal to the DNA brush (FIG. 1F), and leading to a reduced self-regulated expression levels in steady-state.

In order to investigate the effect of compartment geometry on the reaction-diffusion dynamics the present inventors fabricated a device with varying capillary length and integrated up to 80 compartments on the chip. First, they studied three single-gene constructs as a function of the capillary length: unregulated, self-activated, and a negative feedback construct, (FIGS. 2A-C and FIGS. 10A-E). GFP appeared in the compartments in hierarchical order lighting up first in the short capillary (50 µm), attaining low expression levels compared to longer capillaries (FIG. 2A). The onset time, $\tau_{on}(L)$, was indeed linear in the capillary length for the three constructs, as predicted (FIG. 11). In the positive feedback construct, there was a long delay, 1-2.5 hours, before expression onset. The steady-state protein levels of the unregulated and positive feedback constructs were proportional to r and increased linearly with the capillary length over an order of magnitude (FIG. 2F), in accord with the solution to the diffusion equation (See Materials and Methods). The negative feedback construct expression levels were low and independent of length for L>100 µm (FIG. 2F). For short capillaries, L<100 µm, steady-state was not maintained due to rapid diffusion through the channel. All constructs showed a linear GFP profile along the capillary (FIGS. 12A-C). Expression levels showed 10% variation between experiments (FIGS. 13A-D and FIG. 14).

The present inventors next explored the activator-repressor network, which exhibited oscillations and pulses of gene expression. In the first network (FIG. 2D) the sigma factor $\sigma^{28}$ was used for activation and cI was used as the repressor (as in FIG. 1E). The network exhibited oscillations with a period linear in the capillary length (FIGS. 15A-F). Oscillations were also obtained at a different activator:repressor DNA stoichiometry and with the addition of a Cro repressor protein (FIGS. 15A-F). By replacing the activator with a weaker sigma factor, $\sigma^{38}$, single pulse dynamics were obtained (FIG. 2F). Increasing the ratio of activator to repressor genes in the brush changed the dynamics from a pulse to a steady-state of high expression levels (FIGS. 16A-E). Targeting degradation of GFP fused to SsrA or YbaQ tags by the ClpXP complex endogenously present in the cell-free extract (21) showed no detectable difference in dynamics (FIGS. 17A-D).

The present inventors next showed diffusion-based communication with the activator-repressor network separated into two connected compartments (FIGS. 3A-B). Compartment A was positioned 200 µm away from the feeding channel, and the distance to compartment B varied, d=50-300 µm. Compartment A was patterned with activator genes coding for the transcription initiation factor $\sigma^{38}$ and a GFP reporter (FIG. 3A). Compartment B encoded for the lambda phage repressor cI regulated by a $\sigma^{38}$ promoter. GFP appeared after 1 hour in compartment A for all capillary lengths, and independently of the distance d (FIGS. 3B, 18A-B). Following expression in compartment A, the activator $\tau^{38}$ diffused into compartment B and activated the cI repressor expression. In turn, the repressor diffused back to compartment A and shut down $\sigma^{38}$ expression, thereby creating a spatiotemporal pulse (FIG. 3B). The typical time at which expression shuts off, varies 4-8 hours, and was linear with d (FIGS. 18A-B). In a related experiment the positions of A and B were exchanged, resulting in a pulse with onset time and pulse width proportional to d (FIG. 19).

A one-dimensional array of seven compartments was assembled parallel to the flow channel (FIG. 4A The compartments, distance d=200 µm apart, were interconnected by capillaries of length $L_x$=100 µm, and connected to dilution capillaries of length $L_y$=100 µm. A DNA brush coding for GFP was patterned in the first compartment of the array. A gradient of GFP appeared along the array with a maximum intensity at the DNA compartment, dropping in a series of linear steps between neighboring compartments, and with a constant intensity within the compartments (FIGS. 4B,C). The overall profile had an exponentially decaying envelope, $e^{-x/\lambda}$, with a decay length $\lambda$=380±40 µm averaged over 3 experiments. By considering the diffusion equation in the array we theoretically derived a similar value, $$\lambda = d\sqrt{\frac{L_y}{L_x}}, \approx 280 \ \mu m,$$

that is determined only by geometry and is independent of protein diffusion constant.

To examine the response to a signaling molecule in the one-dimensional array, a gene expression cascade was used. The activator gene, coding for $\sigma^{28}$, was patterned in the first compartment of the array, and a GFP under a $\sigma^{28}$ promoter in the second or fourth compartment (FIGS. 4D,E). The activator gene generated a protein concentration gradient along the array, and the reporter gene generated a profile that was maximal at the reporter compartment, and decayed along the array in a piecewise linear profile. The reporter gene was activated with a delay that was dependent on its location along the array and distance from the source (FIG. 4F). The asymmetry in the GFP profile along the array (FIG. 4E) originated from residual flow between compartments (FIGS. 20A-D).

The present approach for an artificial cell offers a means to program a variety of gene expression reactions and biological networks with a high degree of control that is amenable to prediction and theoretical modeling. The diffusion based information transfer between adjacent compartments allows one to envisage a network of connected compartments with emergent spatial-temporal patterns as in morphogenesis.

ADDITIONAL REFERENCES

1. D. S. Tawfik, A. D. Griffiths, Man-made cell-like compartments for molecular evolution., *Nat. Biotechnol.* 16, 652-6 (1998).

2. V. Noireaux, A. Libchaber, A vesicle bioreactor as a step toward an artificial cell assembly., *Proc Natl Acad Sci USA* 101, 17669-74 (2004).
3. V. Noireaux, R. Bar-Ziv, A. Libchaber, Principles of cell-free genetic circuit assembly., *Proc Natl Acad Sci USA* 100, 12672-12677 (2003).
4. J. Kim, K. S. White, E. Winfree, Construction of an in vitro bistable circuit from synthetic transcriptional switches., *Mol. Syst. Biol.* 2, 68 (2006).
5. E. Franco et al., Timing molecular motion and production with a synthetic transcriptional clock., *Proc. Natl. Acad. Sci. U.S.A* 108, E784-93 (2011).
6. A. J. Hockenberry, M. C. Jewett, Synthetic in vitro circuits., *Curr. Opin. Chem. Biol.* 16, 253-9 (2012).
7. M. Isalan, C. Lemerle, L. Serrano, Engineering gene networks to emulate *Drosophila* embryonic pattern formation., *PLoS Biol.* 3, e64 (2005).
8. D. Matthies et al., Cell-free expression and assembly of ATP synthase., *J. Mol. Biol.* 413, 593-603 (2011).
9. Y. Heyman, A. Buxboim, S. G. Wolf, S. S. Daube, R. H. Bar-Ziv, Cell-free protein synthesis and assembly on a biochip, *Nat. Nanotechnol.* 7, 374-378 (2012).
10. J. Shin, P. Jardine, V. Noireaux, Genome replication, synthesis, and assembly of the bacteriophage T7 in a single cell-free reaction., *ACS Synth. Biol.* 1, 408-13 (2012).
11. A. Spirin, V. Baranov, L. Ryabova, S. Ovodov, Y. Alakhov, A continuous cell-free translation system capable of producing polypeptides in high yield, *Science (80-.).* 242, 1162-1164 (1988).
12. T. Thorsen, S. J. Maerkl, S. R. Quake, Microfluidic large-scale integration., *Science* 298, 580-4 (2002).
13. D. Gerber, S. J. Maerkl, S. R. Quake, An in vitro microfluidic approach to generating protein-interaction networks., *Nat. Methods* 6, 71-4 (2009).
14. H. Niederholtmeyer, V. Stepanova, S. J. Maerkl, Implementation of cell-free biological networks at steady state., *Proc. Natl. Acad. Sci. U.S.A* 110, 15985-90 (2013).
15. P. Müller, K. W. Rogers, S. R. Yu, M. Brand, A. F. Schier, Morphogen transport., *Development* 140, 1621-38 (2013).
16. A. Buxboim et al., A single-step photolithographic interface for cell-free gene expression and active biochips, *Small* 3, 500-10 (2007).
17. D. Bracha, E. Karzbrun, S. S. Daube, R. H. Bar-Ziv, Emergent Properties of Dense DNA Phases toward Artificial Biosystems on a Surface., *Acc. Chem. Res.* 47, 1912-1921 (2014).
18. J. Shin, V. Noireaux, Efficient cell-free expression with the endogenous *E. Coli* RNA polymerase and sigma factor 70., *J. Biol. Eng.* 4, 8 (2010).
19. J. Shin, V. Noireaux, An *E. coli* cell-free expression toolbox: application to synthetic gene circuits and artificial cells., *ACS Synth. Biol.* 1, 29-41 (2012).
20. J. Stricker et al., A fast, robust and tunable synthetic gene oscillator., *Nature* 456, 516-9 (2008).
21. J. Shin, V. Noireaux, Study of messenger RNA inactivation and protein degradation in an *Escherichia coli* cell-free expression system, 1-9 (2010).
22. L. H. Hartwell, J. J. Hopfield, S. Leibler, A. W. Murray, From molecular to modular cell biology, *Nature* 402, C47-C52 (1999).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A microfluidic device comprising:
   (i) at least one reaction unit comprising (a) a test chamber and (b) a microchannel, the test chamber connected to said microchannel, wherein a surface of at least a portion of said test chamber of the first of the at least one reaction unit is attached to an isolated, transcribable nucleic acid sequence; and
   (ii) a flow-through channel having at least one inlet port and at least one outlet port, said flow-through channel being connected to said test chamber via said microchannel of said at least one reaction unit, wherein the hydrodynamic resistance of the microchannel is at least $10^5$ times greater than that of the flow-through channel, wherein the hydrodynamic resistance (R) is calculated according to the formula $$R = \frac{1}{5} \frac{L \cdot \eta}{h^3 W \left(1 - 192 \frac{h}{n^5 W} \tanh\left(\frac{\pi W}{2h}\right)\right)}$$

for a channel with length L, height h, width W and with a fluid with viscosity $\eta$;
   wherein said microfluidic device is gas permeable, and wherein said isolated, transcribable nucleic acid sequence is not comprised in or on a cell in said test chamber.

2. The microfluidic device of claim 1 wherein said test chamber is 10-200 microns in diameter.

3. The microfluidic device of claim 1, further comprising at least one of:
   (a) at least one valve to control flow of fluid through said flow-through channel, and
   (b) at least one external reservoir being in fluid communication with said at least one inlet port.

4. The microfluidic device of claim 1, wherein at least a portion of a of said nucleic acid sequence encodes a promoter operatively linked to a nucleic acid encoding a polypeptide.

5. The microfluidic device of claim 4, wherein said polypeptide is a detectable polypeptide and, optionally, a transcription factor.

6. The microfluidic device of claim 1, wherein said at least one reaction unit has two test chambers connected to said microchannel and, optionally, wherein a sequence of the isolated nucleic acid in the first of the two test chambers is different than a sequence of the isolated nucleic acid in the second of the two test chambers.

7. The microfluidic device of claim 1, wherein said nucleic acid is attached to said surface via a reactive group.

8. The microfluidic device of claim 7, wherein said reactive group is photoreactivatable.

9. The microfluidic device of claim 1, wherein said nucleic acid comprises a plurality of nucleic acid sequences.

10. The microfluidic device of claim 9, wherein said plurality of nucleic acid sequences encode a transcriptome.

11. The microfluidic device of claim 1, wherein said nucleic acid comprises at least one of bacterial sequences and eukaryotic sequences.

12. The microfluidic device of claim 1 being fabricated from a substrate having attached thereto a plurality of monolayers said monolayers being composed of a compound which comprises a general formula I:

X-L-Y            Formula I wherein:
   X is a functionalized group capable of binding to said substrate;
   L is a polymer capable of forming said monolayer onto said substrate; and
   Y is a photoactivatable group capable of generating a reactive group upon exposure to said light.

13. The microfluidic device of claim 1, wherein the height h of the at least one microchannel is no more than 20 microns.

14. The microfluidic device of claim 1, wherein the length L of the at least one microchannel is no more than 1 mm.

15. The microfluidic device of claim 1, wherein said device is sealed using a polydimethylsiloxane (PDMS)-coated coverslip.

16. The microfluidic device of claim 1, wherein said isolated nucleic acid is covalently attached to said at least a portion of said test chamber.

17. The microfluidic device of claim 1, wherein the surface of said test chamber is coated with said isolated nucleic acid.

18. The microfluidic device of claim 1, comprising at least two of the at least one reaction units wherein the second of the at least two reaction units is attached to an isolated, transcribable nucleic acid sequence.

19. The microfluidic device of claim 18, wherein the length of the microchannel of the first reaction unit is identical to the length of the microchannel of the second reaction unit.

20. The microfluidic device of claim 18, wherein the length of the microchannel of the first reaction unit is non-identical to the length of the microchannel of the second reaction unit.

21. The microfluidic device of claim 18, wherein the test chamber of the first reaction unit is connected to the test chamber of the second reaction unit via a microchannel.

22. The microfluidic device of claim 18, wherein the microchannel of each of said at least two of the reaction units is connected to the flow channel at one point only.

23. The microfluidic device of claim 18, wherein said device is sealed using a polydimethylsiloxane (PDMS)-coated coverslip.

24. The microfluidic device of claim 18, wherein said isolated nucleic acid is covalently attached to said at least a portion of said test chamber.

25. The microfluidic device of claim 18, wherein the surface of said test chambers of said at least two reaction units is coated with said isolated nucleic acid.

* * * * *

SEQUENCE LISTING

<160> NUMBER OF SEQ ID NOS: 19

<210> SEQ ID NO 1
<211> LENGTH: 16
<212> TYPE: DNA
<213> ORGANISM: Artificial Sequence
<220> FEATURE:
<223> OTHER INFORMATION: Kozak consensus sequence

<400> SEQUENCE: 1
cccgccgccr ccatgg                                                    16

<210> SEQ ID NO 2
<211> LENGTH: 6
<212> TYPE: DNA
<213> ORGANISM: Artificial Sequence
<220> FEATURE:
<223> OTHER INFORMATION: Shine-Delgarno sequence

<400> SEQUENCE: 2 aggagg                                                                6

<210> SEQ ID NO 3

<211> LENGTH: 238
<212> TYPE: PRT
<213> ORGANISM: Aequorea victoria

<400> SEQUENCE: 3

```
Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
50                  55                  60

Gly Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Leu Gln Thr Ala Ile Ser
        195                 200                 205

Lys Asp Arg Asn Glu Thr Arg Asp His Met Val Phe Leu Glu Phe Phe
210                 215                 220

Ser Ala Cys Gly His Thr His Gly Met Asp Glu Leu Tyr Lys
225                 230                 235
```

<210> SEQ ID NO 4
<211> LENGTH: 489
<212> TYPE: PRT
<213> ORGANISM: Artificial Sequence
<220> FEATURE:
<223> OTHER INFORMATION: Cloning vector pSB3616

<400> SEQUENCE: 4

```
Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Leu Gln Gly Thr Ala
            20                  25                  30

Val Asp Gly Gly Gly Ser Met His Ala Ser Leu Glu Val Leu Glu
        35                  40                  45

Asn Arg Ala Ala Gln Gly Asp Ile Thr Ala Pro Gly Gly Ala Arg Arg
    50                  55                  60

Leu Thr Gly Asp Gln Thr Ala Ala Leu Arg Asp Ser Leu Ser Asp Lys
65                  70                  75                  80

Pro Ala Lys Asn Ile Ile Leu Leu Ile Gly Asp Gly Met Gly Asp Ser
                85                  90                  95
```

```
Glu Ile Thr Ala Ala Arg Asn Tyr Ala Gly Ala Gly Gly Phe Phe
                100                 105                 110

Lys Gly Ile Asp Ala Leu Pro Leu Thr Gly Gln Tyr Thr His Tyr Ala
        115                 120                 125

Leu Asn Lys Lys Thr Gly Lys Pro Asp Tyr Val Thr Asp Ser Ala Ala
        130                 135                 140

Ser Ala Thr Ala Trp Ser Thr Gly Val Lys Thr Tyr Asn Gly Ala Leu
145                 150                 155                 160

Gly Val Asp Ile His Glu Lys Asp His Pro Thr Ile Leu Glu Met Ala
                165                 170                 175

Lys Ala Ala Gly Leu Ala Thr Gly Asn Val Ser Thr Ala Glu Leu Gln
            180                 185                 190

Asp Ala Thr Pro Ala Ala Leu Val Ala His Val Thr Ser Arg Lys Cys
        195                 200                 205

Tyr Gly Pro Ser Ala Thr Ser Glu Lys Cys Pro Gly Asn Ala Leu Glu
        210                 215                 220

Lys Gly Gly Lys Gly Ser Ile Thr Glu Gln Leu Leu Asn Ala Arg Ala
225                 230                 235                 240

Asp Val Thr Leu Gly Gly Ala Lys Thr Phe Ala Glu Thr Ala Thr
                245                 250                 255

Ala Gly Glu Trp Gln Gly Lys Thr Leu Arg Glu Gln Ala Gln Ala Arg
            260                 265                 270

Gly Tyr Gln Leu Val Ser Asp Ala Ser Leu Asn Ser Val Thr Glu
        275                 280                 285

Ala Asn Gln Gln Lys Pro Leu Leu Gly Leu Phe Ala Asp Gly Asn Met
        290                 295                 300

Pro Val Arg Trp Leu Gly Pro Lys Ala Thr Tyr His Gly Asn Ile Asp
305                 310                 315                 320

Lys Pro Ala Val Thr Cys Thr Pro Asn Pro Gln Arg Asn Asp Ser Val
                325                 330                 335

Pro Thr Leu Ala Gln Met Thr Asp Lys Ala Ile Glu Leu Leu Ser Lys
            340                 345                 350

Asn Glu Lys Gly Phe Phe Leu Gln Val Glu Gly Ala Ser Ile Asp Lys
        355                 360                 365

Gln Asp His Ala Ala Asn Pro Cys Gly Gln Ile Gly Glu Thr Val Asp
    370                 375                 380

Leu Asp Glu Ala Val Gln Arg Ala Leu Glu Phe Ala Lys Lys Glu Gly
385                 390                 395                 400

Asn Thr Leu Val Ile Val Thr Ala Asp His Ala His Ala Ser Gln Ile
                405                 410                 415

Val Ala Pro Asp Thr Lys Ala Pro Gly Leu Thr Gln Ala Leu Asn Thr
            420                 425                 430

Lys Asp Gly Ala Val Met Val Met Ser Tyr Gly Asn Ser Glu Glu Asp
        435                 440                 445

Ser Gln Glu His Thr Gly Ser Gln Leu Arg Ile Ala Ala Tyr Gly Pro
        450                 455                 460

His Ala Ala Asn Val Val Gly Leu Thr Asp Gln Thr Asp Leu Phe Tyr
465                 470                 475                 480

Thr Met Lys Ala Ala Leu Gly Leu Lys
                485

<210> SEQ ID NO 5
<211> LENGTH: 309
<212> TYPE: PRT
```

<213> ORGANISM: Armoracia rusticana

<400> SEQUENCE: 5

```
Met Gln Leu Thr Pro Thr Phe Tyr Asp Asn Ser Cys Pro Asn Val Ser
1               5                   10                  15

Asn Ile Val Arg Asp Thr Ile Val Asn Glu Leu Arg Ser Asp Pro Arg
            20                  25                  30

Ile Ala Ala Ser Ile Leu Arg Leu His Phe His Asp Cys Phe Val Asn
        35                  40                  45

Gly Cys Asp Ala Ser Ile Leu Leu Asp Asn Thr Thr Ser Phe Arg Thr
    50                  55                  60

Glu Lys Asp Ala Phe Gly Asn Ala Asn Ser Ala Arg Gly Phe Pro Val
65                  70                  75                  80

Ile Asp Arg Met Lys Ala Ala Val Glu Ser Ala Cys Pro Arg Thr Val
                85                  90                  95

Ser Cys Ala Asp Leu Leu Thr Ile Ala Ala Gln Gln Ser Val Thr Leu
            100                 105                 110

Ala Gly Gly Pro Ser Trp Arg Val Pro Leu Gly Arg Arg Asp Ser Leu
        115                 120                 125

Gln Ala Phe Leu Asp Leu Ala Asn Ala Asn Leu Pro Ala Pro Phe Phe
    130                 135                 140

Thr Leu Pro Gln Leu Lys Asp Ser Phe Arg Asn Val Gly Leu Asn Arg
145                 150                 155                 160

Ser Ser Asp Leu Val Ala Leu Ser Gly Gly His Thr Phe Gly Lys Asn
                165                 170                 175

Gln Cys Arg Phe Ile Met Asp Arg Leu Tyr Asn Phe Ser Asn Thr Gly
            180                 185                 190

Leu Pro Asp Pro Thr Leu Asn Thr Thr Tyr Leu Gln Thr Leu Arg Gly
        195                 200                 205

Leu Cys Pro Leu Asn Gly Asn Leu Ser Ala Leu Val Asp Phe Asp Leu
    210                 215                 220

Arg Thr Pro Thr Ile Phe Asp Asn Lys Tyr Tyr Val Asn Leu Glu Glu
225                 230                 235                 240

Gln Lys Gly Leu Ile Gln Ser Asp Gln Glu Leu Phe Ser Ser Pro Asn
                245                 250                 255

Ala Thr Asp Thr Ile Pro Leu Val Arg Ser Phe Ala Asn Ser Thr Gln
            260                 265                 270

Thr Phe Phe Asn Ala Phe Val Glu Ala Met Asp Arg Met Gly Asn Ile
        275                 280                 285

Thr Pro Leu Thr Gly Thr Gln Gly Gln Ile Arg Leu Asn Cys Arg Val
    290                 295                 300

Val Asn Ser Asn Ser
305
```

<210> SEQ ID NO 6
<211> LENGTH: 286
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (264)..(269)
<223> OTHER INFORMATION: Histidine tag

<400> SEQUENCE: 6

```
Gln Ser Val Leu Thr Gln Pro Pro Ser Val Ser Gly Ser Pro Gly Gln
```

```
                1               5                  10                 15
      Ser Ile Thr Ile Ser Cys Thr Gly Thr Ser Ser Asp Ile Gly Thr Tyr
                        20                  25                 30

Lys Ile Val Ser Trp Tyr Gln Gln His Pro Gly Lys Ala Pro Lys Leu
                        35                  40                 45

Met Ile Tyr Asp Val Asn Gln Arg Pro Ser Gly Val Ser Asp Arg Phe
                  50                  55                 60

Ser Gly Ser Lys Ser Gly Asn Thr Ala Ser Leu Thr Ile Ser Gly Leu
      65                  70                  75                 80

Gln Ala Glu Asp Glu Ala Asp Tyr Tyr Cys Ser Ser Tyr Thr Ser Gly
                        85                  90                 95

Ser Thr Leu Val Phe Gly Gly Gly Thr Lys Leu Thr Val Leu Gly Ser
                        100                 105                110

Ser Gly Gly Gly Gly Ser Gly Gly Gly Ser Gly Gly Ser Ala Leu
                        115                 120                125

Gln Val Gln Leu Gln Gln Ser Gly Ala Glu Val Lys Lys Pro Gly Glu
                        130                 135                140

Ser Leu Lys Ile Ser Cys Lys Gly Ser Gly Tyr Ser Phe Thr Ser Tyr
      145                 150                 155                160

Trp Ile Gly Trp Val Arg Gln Met Pro Gly Lys Gly Leu Glu Trp Met
                        165                 170                175

Gly Ile Ile Tyr Pro Gly Asp Ser Asp Thr Arg Tyr Ser Pro Ser Phe
                        180                 185                190

Gln Gly Gln Val Thr Ile Ser Ala Asp Lys Ser Ile Ser Thr Ala Tyr
                        195                 200                205

Leu Gln Trp Ser Ser Leu Lys Ala Ser Asp Thr Ala Met Tyr Tyr Cys
                  210                 215                 220

Ala Arg His Arg Ala Ala Ser Gly Ser Pro Asp Ala Cys Asp Tyr Trp
      225                 230                 235                240

Gly Gln Gly Thr Leu Val Thr Val Ser Ser Gly Ser Ala Ser Ala Pro
                        245                 250                255

Thr Leu Phe Pro Ala Ala Ala His His His His His His Gly Ala Ala
                        260                 265                270

Glu Gln Lys Leu Ile Ser Glu Glu Asp Leu Asn Gly Ala Ala
                        275                 280                285

<210> SEQ ID NO 7
<211> LENGTH: 286
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (273)..(283)
<223> OTHER INFORMATION: Myc tag

<400> SEQUENCE: 7

Gln Ser Val Leu Thr Gln Pro Pro Ser Val Ser Gly Ser Pro Gly Gln
      1               5                   10                 15

Ser Ile Thr Ile Ser Cys Thr Gly Thr Ser Ser Asp Ile Gly Thr Tyr
                        20                  25                 30

Lys Ile Val Ser Trp Tyr Gln Gln His Pro Gly Lys Ala Pro Lys Leu
                        35                  40                 45

Met Ile Tyr Asp Val Asn Gln Arg Pro Ser Gly Val Ser Asp Arg Phe
                  50                  55                 60
```

-continued

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Gly
                 85                  90                  95

Ser Thr Leu Val Phe Gly Gly Gly Thr Lys Leu Thr Val Leu Gly Ser
            100                 105                 110

Ser Gly Gly Gly Ser Gly Gly Gly Ser Gly Gly Ser Ala Leu
        115                 120                 125

Gln Val Gln Leu Gln Gln Ser Gly Ala Glu Val Lys Lys Pro Gly Glu
    130                 135                 140

Ser Leu Lys Ile Ser Cys Lys Gly Ser Gly Tyr Ser Phe Thr Ser Tyr
145                 150                 155                 160

Trp Ile Gly Trp Val Arg Gln Met Pro Gly Lys Gly Leu Glu Trp Met
                165                 170                 175

Gly Ile Ile Tyr Pro Gly Asp Ser Asp Thr Arg Tyr Ser Pro Ser Phe
            180                 185                 190

Gln Gly Gln Val Thr Ile Ser Ala Asp Lys Ser Ile Ser Thr Ala Tyr
        195                 200                 205

Leu Gln Trp Ser Ser Leu Lys Ala Ser Asp Thr Ala Met Tyr Tyr Cys
    210                 215                 220

Ala Arg His Arg Ala Ala Ser Gly Ser Pro Asp Ala Cys Asp Tyr Trp
225                 230                 235                 240

Gly Gln Gly Thr Leu Val Thr Val Ser Ser Gly Ser Ala Ser Ala Pro
                245                 250                 255

Thr Leu Phe Pro Ala Ala His His His His His His Gly Ala Ala
            260                 265                 270

Glu Gln Lys Leu Ile Ser Glu Glu Asp Leu Asn Gly Ala Ala
        275                 280                 285

<210> SEQ ID NO 8
<211> LENGTH: 15
<212> TYPE: PRT
<213> ORGANISM: Artificial Sequence
<220> FEATURE:
<223> OTHER INFORMATION: Biotin lygase tag

<400> SEQUENCE: 8

Leu His His Ile Leu Asp Ala Gln Lys Met Val Trp Asn His Arg
1               5                   10                  15

<210> SEQ ID NO 9
<211> LENGTH: 238
<212> TYPE: PRT
<213> ORGANISM: Aequorea macrodactyla

<400> SEQUENCE: 9

Met Ser Lys Gly Glu Glu Leu Phe Thr Gly Val Val Pro Ile Leu Val
1               5                   10                  15

Glu Leu Asp Gly Asp Val His Gly His Lys Phe Ser Val Arg Gly Glu
                20                  25                  30

Gly Glu Gly Asp Ala Asp Tyr Gly Lys Leu Glu Ile Lys Phe Ile Cys
            35                  40                  45

Thr Thr Gly Lys Leu Pro Val Pro Trp Pro Thr Leu Val Thr Thr Leu
        50                  55                  60

Gly Tyr Gly Ile Leu Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
```

Thr Ile Phe Phe Gln Asp Asp Gly Lys Tyr Lys Thr Arg Gly Glu Val
            85                  90                  95

Lys Phe Glu Gly Asp Thr Leu Val Asn Arg Ile Glu Leu Lys Gly Met
        100                 105                 110

Asp Phe Lys Glu Asp Gly Asn Ile Leu Gly His Lys Leu Glu Tyr Asn
    115                 120                 125

Phe Asn Ser His Asn Val Tyr Ile Met Pro Asp Lys Ala Asn Asn Gly
130                 135                 140

Leu Lys Val Asn Phe Lys Ile Arg His Asn Ile Glu Gly Gly Gly Val
145                 150                 155                 160

Gln Leu Ala Asp His Tyr Gln Thr Asn Val Pro Leu Gly Asp Gly Pro
        165                 170                 175

Val Leu Ile Pro Ile Asn His Tyr Leu Ser Tyr Gln Thr Ala Ile Ser
    180                 185                 190

Lys Asp Arg Asn Glu Thr Arg Asp His Met Val Phe Leu Glu Phe Phe
195                 200                 205

Ser Ala Cys Gly His Thr His Gly Met Asp Glu Leu Tyr Lys
210                 215                 220

225                 230                 235

<210> SEQ ID NO 10
<211> LENGTH: 1019
<212> TYPE: PRT
<213> ORGANISM: Artificial Sequence
<220> FEATURE:
<223> OTHER INFORMATION: Vector pFRT1-lacZ-Tel

<400> SEQUENCE: 10

Met Ala Asp Pro Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg Pro Ser Gln Gln Leu Arg
        35                  40                  45

Ser Leu Asn Gly Glu Trp Arg Phe Ala Trp Phe Pro Ala Pro Glu Ala
    50                  55                  60

Val Pro Glu Ser Trp Leu Glu Cys Asp Leu Pro Glu Ala Asp Thr Val
65                  70                  75                  80

Val Val Pro Ser Asn Trp Gln Met His Gly Tyr Asp Ala Pro Ile Tyr
            85                  90                  95

Thr Asn Val Thr Tyr Pro Ile Thr Val Asn Pro Pro Phe Val Pro Thr
        100                 105                 110

Glu Asn Pro Thr Gly Cys Tyr Ser Leu Thr Phe Asn Val Asp Glu Ser
    115                 120                 125

Trp Leu Gln Glu Gly Gln Thr Arg Ile Ile Phe Asp Gly Val Asn Ser
130                 135                 140

Ala Phe His Leu Trp Cys Asn Gly Arg Trp Val Gly Tyr Gly Gln Asp
145                 150                 155                 160

Ser Arg Leu Pro Ser Glu Phe Asp Leu Ser Ala Phe Leu Arg Ala Gly
        165                 170                 175

Glu Asn Arg Leu Ala Val Met Val Leu Arg Trp Ser Asp Gly Ser Tyr
    180                 185                 190

Leu Glu Asp Gln Asp Met Trp Arg Met Ser Gly Ile Phe Arg Asp Val
195                 200                 205

Ser Leu Leu His Lys Pro Thr Thr Gln Ile Ser Asp Phe His Val Ala

```
                210                 215                 220
Thr Arg Phe Asn Asp Asp Phe Ser Arg Ala Val Leu Glu Ala Glu Val
225                 230                 235                 240

Gln Met Cys Gly Glu Leu Arg Asp Tyr Leu Arg Val Thr Val Ser Leu
                245                 250                 255

Trp Gln Gly Glu Thr Gln Val Ala Ser Gly Thr Ala Pro Phe Gly Gly
                260                 265                 270

Glu Ile Ile Asp Glu Arg Gly Gly Tyr Ala Asp Arg Val Thr Leu Arg
                275                 280                 285

Leu Asn Val Glu Asn Pro Lys Leu Trp Ser Ala Glu Ile Pro Asn Leu
                290                 295                 300

Tyr Arg Ala Val Val Glu Leu His Thr Ala Asp Gly Thr Leu Ile Glu
305                 310                 315                 320

Ala Glu Ala Cys Asp Val Gly Phe Arg Glu Val Arg Ile Glu Asn Gly
                325                 330                 335

Leu Leu Leu Leu Asn Gly Lys Pro Leu Leu Ile Arg Gly Val Asn Arg
                340                 345                 350

His Glu His His Pro Leu His Gly Gln Val Met Asp Glu Gln Thr Met
                355                 360                 365

Val Gln Asp Ile Leu Leu Met Lys Gln Asn Asn Phe Asn Ala Val Arg
370                 375                 380

Cys Ser His Tyr Pro Asn His Pro Leu Trp Tyr Thr Leu Cys Asp Arg
385                 390                 395                 400

Tyr Gly Leu Tyr Val Val Asp Glu Ala Asn Ile Glu Thr His Gly Met
                405                 410                 415

Val Pro Met Asn Arg Leu Thr Asp Asp Pro Arg Trp Leu Pro Ala Met
                420                 425                 430

Ser Glu Arg Val Thr Arg Met Val Gln Arg Asp Arg Asn His Pro Ser
                435                 440                 445

Val Ile Ile Trp Ser Leu Gly Asn Glu Ser Gly His Gly Ala Asn His
                450                 455                 460

Asp Ala Leu Tyr Arg Trp Ile Lys Ser Val Asp Pro Ser Arg Pro Val
465                 470                 475                 480

Gln Tyr Glu Gly Gly Gly Ala Asp Thr Thr Ala Thr Asp Ile Ile Cys
                485                 490                 495

Pro Met Tyr Ala Arg Val Asp Glu Asp Gln Pro Phe Pro Ala Val Pro
                500                 505                 510

Lys Trp Ser Ile Lys Lys Trp Leu Ser Leu Pro Gly Glu Thr Arg Pro
                515                 520                 525

Leu Ile Leu Cys Glu Tyr Ala His Ala Met Gly Asn Ser Leu Gly Gly
                530                 535                 540

Phe Ala Lys Tyr Trp Gln Ala Phe Arg Gln Tyr Pro Arg Leu Gln Gly
545                 550                 555                 560

Gly Phe Val Trp Asp Trp Val Asp Gln Ser Leu Ile Lys Tyr Asp Glu
                565                 570                 575

Asn Gly Asn Pro Trp Ser Ala Tyr Gly Gly Asp Phe Gly Asp Thr Pro
                580                 585                 590

Asn Asp Arg Gln Phe Cys Met Asn Gly Leu Val Phe Ala Asp Arg Thr
                595                 600                 605

Pro His Pro Ala Leu Thr Glu Ala Lys His Gln Gln Gln Phe Phe Gln
                610                 615                 620

Phe Arg Leu Ser Gly Gln Thr Ile Glu Val Thr Ser Glu Tyr Leu Phe
625                 630                 635                 640
```

Arg His Ser Asp Asn Glu Leu Leu His Trp Met Val Ala Leu Asp Gly
            645                 650                 655

Lys Pro Leu Ala Ser Gly Glu Val Pro Leu Asp Val Ala Pro Gln Gly
            660                 665                 670

Lys Gln Leu Ile Glu Leu Pro Glu Leu Pro Gln Pro Glu Ser Ala Gly
            675                 680                 685

Gln Leu Trp Leu Thr Val Arg Val Gln Pro Asn Ala Thr Ala Trp
            690                 695                 700

Ser Glu Ala Gly His Ile Ser Ala Trp Gln Gln Trp Arg Leu Ala Glu
705                 710                 715                 720

Asn Leu Ser Val Thr Leu Pro Ala Ala Ser His Ala Ile Pro His Leu
            725                 730                 735

Thr Thr Ser Glu Met Asp Phe Cys Ile Glu Leu Gly Asn Lys Arg Trp
            740                 745                 750

Gln Phe Asn Arg Gln Ser Gly Phe Leu Ser Gln Met Trp Ile Gly Asp
            755                 760                 765

Lys Lys Gln Leu Leu Thr Pro Leu Arg Asp Gln Phe Thr Arg Ala Pro
770                 775                 780

Leu Asp Asn Asp Ile Gly Val Ser Glu Ala Thr Arg Ile Asp Pro Asn
785                 790                 795                 800

Ala Trp Val Glu Arg Trp Lys Ala Ala Gly His Tyr Gln Ala Glu Ala
                    805                 810                 815

Ala Leu Leu Gln Cys Thr Ala Asp Thr Leu Ala Asp Ala Val Leu Ile
                    820                 825                 830

Thr Thr Ala His Ala Trp Gln His Gln Gly Lys Thr Leu Phe Ile Ser
                    835                 840                 845

Arg Lys Thr Tyr Arg Ile Asp Gly Ser Gly Gln Met Ala Ile Thr Val
850                 855                 860

Asp Val Glu Val Ala Ser Asp Thr Pro His Pro Ala Arg Ile Gly Leu
865                 870                 875                 880

Asn Cys Gln Leu Ala Gln Val Ala Glu Arg Val Asn Trp Leu Gly Leu
                    885                 890                 895

Gly Pro Gln Glu Asn Tyr Pro Asp Arg Leu Thr Ala Ala Cys Phe Asp
                    900                 905                 910

Arg Trp Asp Leu Pro Leu Ser Asp Met Tyr Thr Pro Tyr Val Phe Pro
                    915                 920                 925

Ser Glu Asn Gly Leu Arg Cys Gly Thr Arg Glu Leu Asn Tyr Gly Pro
930                 935                 940

His Gln Trp Arg Gly Asp Phe Gln Phe Asn Ile Ser Arg Tyr Ser Gln
945                 950                 955                 960

Gln Gln Leu Met Glu Thr Ser His Arg His Leu Leu His Ala Glu Glu
                    965                 970                 975

Gly Thr Trp Leu Asn Ile Asp Gly Phe His Met Gly Ile Gly Gly Asp
                    980                 985                 990

Asp Ser Trp Ser Pro Ser Val Ser Ala Asp Phe Gln Leu Ser Ala Gly
                    995                 1000                1005

Arg Tyr His Tyr Gln Leu Val Trp Cys Gln Lys
        1010                1015

<210> SEQ ID NO 11
<211> LENGTH: 159
<212> TYPE: PRT
<213> ORGANISM: Artificial Sequence
<220> FEATURE:

<223> OTHER INFORMATION: synthetic construct, streptavidin

<400> SEQUENCE: 11

Asp Pro Ser Lys Asp Ser Lys Ala Gln Val Ser Ala Ala Glu Ala Gly
1               5                   10                  15
Ile Thr Gly Thr Trp Tyr Asn Gln Leu Gly Ser Thr Phe Ile Val Thr
            20                  25                  30
Ala Gly Ala Asp Gly Ala Leu Thr Gly Thr Tyr Glu Ser Ala Val Gly
        35                  40                  45
Asn Ala Glu Ser Arg Tyr Val Leu Thr Gly Arg Tyr Asp Ser Ala Pro
    50                  55                  60
Ala Thr Asp Gly Ser Gly Thr Ala Leu Gly Trp Thr Val Ala Trp Lys
65                  70                  75                  80
Asn Asn Tyr Arg Asn Ala His Ser Ala Thr Thr Trp Ser Gly Gln Tyr
                85                  90                  95
Val Gly Gly Ala Glu Ala Arg Ile Asn Thr Gln Trp Leu Leu Thr Ser
            100                 105                 110
Gly Thr Thr Glu Ala Asn Ala Trp Lys Ser Thr Leu Val Gly His Asp
        115                 120                 125
Thr Phe Thr Lys Val Lys Pro Ser Ala Ala Ser Ile Asp Ala Ala Lys
    130                 135                 140
Lys Ala Gly Val Asn Asn Gly Asn Pro Leu Asp Ala Val Gln Gln
145                 150                 155

<210> SEQ ID NO 12
<211> LENGTH: 717
<212> TYPE: DNA
<213> ORGANISM: Aequorea macrodactyla

<400> SEQUENCE: 12
atgagtaaag gagaagaact tttcactggg attgtcccag ttctcattga gttagacggt    60
gatgtccatg gacataaatt ctctgtcaga ggagaagggg aaggcgatgc agattatgga   120
aaacttgaaa tcaaattcat ttgcactact ggaaagctac cagttccatg ccaacacttt   180
gttactacac tgggctacgg catccaatgt ttcgcaagat acccagaaca catgaaaatg   240
aatgacttct tcaagagtgc catgcctgag ggttacattc aagaaagaac catctttttc   300
caagatgatg gaaaatacaa gacacgtggt gaagtcaagt ttgaaggtga tactcttgtt   360
aacagaattg agctcaaagg tatggacttt aagaagatgg caatatcct tggacacaag   420
ttggagtaca atttta attc acataatgta tacattatgc cggacaaagc caataatgga   480
ctcaaagtca atttcaaaat tagacacaat atcgaaggtg gtggtgtcca acttgctgat   540
cattaccaaa caaatgttcc ccttggagac ggtcctgtcc ttataccaat caatcactac   600
ctatccttgc aaacagccat ttcaaaagat cgaaatgaga cgagagatca tatggtgttt   660
ctggaatttt tctcagcttg tggacataca catggcatgg atgaactata caaataa     717

<210> SEQ ID NO 13
<211> LENGTH: 7151
<212> TYPE: DNA
<213> ORGANISM: Artificial Sequence
<220> FEATURE:
<223> OTHER INFORMATION: Cloning vector pSB3616 alkaline phosphatase
      (phoA), lac repressor (lacI), and chloramphenicol
      acetyltransferase (cat) genes, complete cds.

<400> SEQUENCE: 13
gaattccgga tgagcattca tcaggcgggc aagaatgtga ataaaggccg gataaaactt    60

```
gtgcttattt ttctttacgg tctttaaaaa ggccgtaata tccagctgaa cggtctggtt      120
ataggtacat tgagcaactg actgaaatgc ctcaaaatgt tctttacgat gccattggga      180
tatatcaacg gtggtatatc cagtgatttt tttctccatt ttagcttcct tagctcctga      240
aaatctcgat aactcaaaaa atacgcccgg tagtgatctt atttcattat ggtgaaagtt      300
ggaacctctt acgtgccgat caacgtctca ttttcgccaa aagttggccc agggcttccc      360
ggtatcaaca gggacaccag gatttattta ttctgcgaag tgatcttccg tcacaggtat      420
ttattcggcg caaagtgcgt cgggtgatgc tgccaactta ctgatttagt gtatgatggt      480 gttttgagg tgctccagtg gcttctgttt ctatcagctg tccctcctgt tcagctactg      540
acggggtggt gcgtaacggc aaaagcaccg ccggacatca gcgctagcgg agtgtatact      600
ggcttactat gttggcactg atgagggtgt cagtgaagtg cttcatgtgg caggagaaaa      660
aaggctgcac cggtgcgtca gcagaatatg tgatacagga tatattccgc ttcctcgctc      720
actgactcgc tacgctcggt cgttcgactg cggcgagcgg aaatggctta cgaacggggc      780
ggagatttcc tggaagatgc caggaagata cttaacaggg aagtgagagg gccgcggcaa      840
agccgttttt ccataggctc cgccccctg acaagcatca cgaaatctga cgctcaaatc      900
agtggtggcg aaacccgaca ggactataaa gataccaggc gtttccccct ggcggctccc      960
tcgtgcgctc tcctgttcct gcctttcggt ttaccggtgt cattccgctg ttatggccgc     1020
gtttgtctca ttccacgcct gacactcagt tccgggtagg cagttcgctc caagctggac     1080
tgtatgcacg aaccccccgt tcagtccgac cgctgcgcct tatccggtaa ctatcgtctt     1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaacctt     1320
cgaaaaaccg ccctgcaagg cggttttttc gttttcagag caagagatta cgcgcagacc     1380
aaaacgatct caagaagatc atcttattaa tcagataaaa tatttctaga tttcagtgca     1440
atttatctct tcaaatgtag cacctgaagt cagccccata cgatataagt tgtaattctc     1500
atgtttgaca gcttatcatc gataagcttt tttcgccagg cgcagacttg ctgttcttca     1560
ggcaatcact catgtaggtc ttacgagcat cccctttcaa cgcctgcgcc gtcgcctgct     1620
gattacagga ggtcatacgc tgttgttgtg gggttaaagt tctctcggca gcgccgacgg     1680
tggttaaaaa aaccagaccg aaaagcaagg taaccagtaa tgttattttc atagcaccat     1740
ccctcttcat gttttaacca tgagcgtatg cgcccgtgat ctgccattaa gtctggttgc     1800
taacagcaaa aaaaccaccc ggcagcgaaa attcactgcc gggcgcggtt ttatttcagc     1860
cccagagcgc ctttcatggt gtagaagaga tcggtctggt cggtcagtcc aacaacattg     1920
gcggcatgcg ggccatacgc cgcaatacgc aactgactgc cggtatgttc ttgtgaatcc     1980
tcttcggagt tcccgtaact catcaccatc actgcgccat ctttggtatt tagcgcctgg     2040
gtgaggcccg gagctttggt atccggcgca acaatctggc tggcgtgggc gtgatcagcg     2100
gtgactatga ccagcgtgtt accctccttt ttagcgaatt ccagcgcccg ttgtacggct     2160
tcatcgagat cgaccgtctc gccaatttgc ccacaaggat tcgcagcatg atcctgttta     2220
tcgattgacg caccttcaac ttgcaggaaa aagcctttct catttttact caacaattca     2280
atggctttgt cggtcatctg cgccagggtt ggtacactgt cattacgttg cggatttggc     2340
gtacaggtga ctgcgggctt atcgatattg ccatggtacg ttgctttcgg tcctagccag     2400
```

-continued

| | |
|---|---|
| cgcactggca tattgccgtc agcaaacagg ccaagcaggg gttttgctg attcgcttcc | 2460 |
| gtcaccgaat tcagtgaggc agcatcgctc accaactgat aaccacgcgc ctgtgcctgt | 2520 |
| tcacgcagcg ttttcccctg ccattcacca gcggttgccg tttcagcaaa ggttttgcg | 2580 |
| ccgccgccaa gcgtaacgtc ggcacgagcg ttaagcagct gttcggtaat cgatccttt | 2640 |
| ccgccttttt ccagagcgtt acccggacat tttcactgg tcgcgctcgg accgtagcat | 2700 |
| ttgcgcgagg tcacatgtgc caccagcgca gcgggcgtgg catcctgcaa ctctgcggta | 2760 |
| gaaacgttac cggtcgccag acctgcggct tttgccattt ccagaatcgt tgggtgatct | 2820 |
| ttttcgtgaa tatcgacgcc cagcgcgccg ttataggttt tgacaccggt tgaccaggcg | 2880 |
| gttgctgatg cagccgagtc ggtgacgtag tccggtttgc cggtttttt attcagcgca | 2940 |
| tagtgagtgt attgcccggt aagcggtaag gcatctatac cttaaaaaa gccgcccgca | 3000 |
| ccttcggcat aattacgtgc ggcagtaatt tccgagtccc ccatcccatc gccaatcagc | 3060 |
| aaaataatat ttttgcagg tttatcgcta agaatcac gcagagcggc agtctgatca | 3120 |
| cccgttaaac ggcgagcacc gccgggtgca gtaatatcgc cctgagcagc ccggtttcc | 3180 |
| agaacctcga ggctagcatg catagaaccg ccaccaccgt cgacagcggt accctgcaga | 3240 |
| ggcatttctg gtgtccgggc ttttgtcaca ggggtaaaca gtaacggtaa gagtgccagt | 3300 |
| gcaatagtgc tttgtttcac tttattttct ccatgtcgcg tcttatcagg gggaattctg | 3360 |
| tttcctgtgt gaaattgtta tccgctcaca attccacaca ttatacgagc cgatgattaa | 3420 |
| ttgtcaacag ctcattcag aatatttgcc agaaccgtta tgatgtcggc gcaaaaaaca | 3480 |
| ttatctagag gggaattgtt atccgctcac aattcccta tagtgagtcg tattaatttc | 3540 |
| gcgggatcga gatctcgatc ctctacgccg gacgcatcgt ggccggcatc accggcgcca | 3600 |
| caggtgcggt tgctggcgcc tatatcgccg acatcaccga tggggaagat cgggctcgcc | 3660 |
| acttcgggct catgagcgct tgtttcggcg tgggtatggt ggcaggcccc gtggccgggg | 3720 |
| gactgttggg cgccatctcc ttgcatgcac cattccttgc ggcggcggtg ctcaacggcc | 3780 |
| tcaacctact actgggctgc ttcctaatgc aggagtcgca taagggagag cgtcgagatc | 3840 |
| ccggacacca tcgaatggcg caaaaccttt cgcggtatgg catgatagcg cccggaagag | 3900 |
| agtcaattca gggtggtgaa tgtgaaacca gtaacgttat acgatgtcgc agagtatgcc | 3960 |
| ggtgtctctt atcagaccgt ttcccgcgtg gtgaaccagg ccagccacgt ttctgcgaaa | 4020 |
| acgcgggaaa aagtggaagc ggcgatggcg gagctgaatt acattcccaa ccgcgtggca | 4080 |
| caacaactgg cgggcaaaca gtcgttgctg attggcgttg ccacctccag tctggccctg | 4140 |
| cacgcgccgt cgcaaattgt cgcggcgatt aaatctcgcg ccgatcaact gggtgccagc | 4200 |
| gtggtggtgt cgatggtaga acgaagcggc gtcgaagcct gtaaagcggc ggtgcacaat | 4260 |
| cttctcgcgc aacgcgtcag tgggctgatc attaactatc cgctggatga ccaggatgcc | 4320 |
| attgctgtgg aagctgcctg cactaatgtt ccggcgttat ttcttgatgt ctctgaccag | 4380 |
| acacccatca acagtattat tttctcccat gaagacggta cgcgactggg cgtggagcat | 4440 |
| ctggtcgcat tgggtcacca gcaaatcgcg ctgttagcgg gcccattaag ttctgtctcg | 4500 |
| gcgcgtctgc gtctggctgg ctggcataaa tatctcactc gcaatcaaat tcagccgata | 4560 |
| gcggaacggg aaggcgactg gagtgccatg tccggttttc aacaaaccat gcaaatgctg | 4620 |
| aatgagggca tcgttcccac tgcgatgctg gttgccaacg atcagatggc gctgggcgca | 4680 |
| atgcgcgcca ttaccgagtc cgggctgcgc gttggtgcgg atatctcggt agtgggatac | 4740 |
| gacgataccg aagacagctc atgttatatc ccgccgttaa ccaccatcaa acaggatttt | 4800 |

```
cgcctgctgg ggcaaaccag cgtggaccgc ttgctgcaac tctctcaggg ccaggcggtg    4860
aagggcaatc agctgttgcc cgtctcactg gtgaaaagaa aaaccaccct ggcgcccaat    4920
acgcaaaccg cctctccccg cgcgttggcc gattcattaa tgcagctggc acgacaggtt    4980
tcccgactgg aaagcgggca gtgagcgcaa cgcaattaat gtaagttagc tcactcatta    5040
ggcaccggga tctcgaccga tgcccttgag agccttcaac ccagtcagct ccttccggtg    5100
ggcgcggggc atgactatcg tcgccgcact tatgactgtc ttctttatca tgcaactcgt    5160
aggacaggtg ccggcagcgc tctgggtcat tttcggcgag gaccgctttc gctggagcgc    5220
gacgatgatc ggcctgtcgc ttgcggtatt cggaatcttg cacgccctcg ctcaagcctt    5280
cgtcactggt cccgccacca aacgtttcgg cgagaagcag gccattatcg ccggcatggc    5340
ggccgacgcg ctgggctacg tcttgctggc gttcgcgacg cgaggctgga tggccttccc    5400
cattatgatt cttctcgctt ccggcggcat cgggatgccc gcgttgcagg ccatgctgtc    5460
caggcaggta gatgacgacc atcagggaca gcttcaagga tcgctcgcgg ctcttaccag    5520
cctaacttcg atcactggac cgctgatcgt cacggcgatt tatgccgcct cggcgagcac    5580
atggaacggg ttggcatgga ttgtaggcgc cgccctatac cttgtctgcc tccccgcgtt    5640
gcgtcgcggt gcatggagcc gggccacctc gacctgaatg gaagccggcg gcacctcgct    5700
aacggattca ccactccaag aattggagcc aatcaattct tgcggagaac tgtgaatgcg    5760
caaaccaacc cttggcagaa catatccatc gcgtccgcca tctccagcag ccgcacgcgg    5820
cgcatctcgg gcagcgttgg gtcctggcca cgggtgcgca tgatcgtgct cctgtcgttg    5880
aggacccggc taggctggcg gggttgcctt actggttagc agaatgaatc accgatacgc    5940
gagcgaacgt gaagcgactg ctgctgcaaa acgtctgcga cctgagcaac aacatgaatg    6000
gtcttcggtt tccgtgtttc gtaaagtctg gaaacgcgga agtccctac gtgctgctga    6060 agttgcccgc aacagagagt ggaaccaacc ggtgatacca cgatactatg actgagagtc    6120
aacgccatga gcggcctcat ttcttattct gagttacaac agtccgcacc gctgtccggt    6180
agctccttcc ggtgggcgcg gggcatgact atcgtcgccg cacttatgac tgtcttcttt    6240
atcatgcaac tcgtaggaca ggtgccggca gcgcccaaca gtcccccggc cacggggcct    6300
gccaccatac ccacgccgaa acaagcgccc tgcaccatta tgttccggat ctgcatcgca    6360
ggatgctgct ggctaccctg tggaacacct acatctgtat taacgaagcg ctaaccgttt    6420
ttatcaggct ctgggaggca gaataaatga tcatatcgtc aattattacc tccacgggga    6480
gagcctgagc aaactggcct caggcatttg agaagcacac ggtcacactg cttccggtag    6540
tcaataaacc ggtaaaccag caatagacat aagcggctat ttaacgaccc tgccctgaac    6600
cgacgaccgt gtcgaatttg ctttcgaatt tctgccattc atccgcttat tatcacttat    6660
tcaggcgtag caccaggcgt ttaagggcac caataactgc cttaaaaaaa ttacgccccg    6720
ccctgccact catcgcagta ctgttgtaat tcattaagca ttctgccgac atggaagcca    6780
tcacagacgg catgatgaac ctgaatcgcc agcggcatca gcaccttgtc gccttgcgta    6840
taatatttgc ccatggtgaa acgggggcg aagaagttgt ccatattggc cacgtttaaa    6900
tcaaaactgg tgaaactcac ccagggattg gctgagacga aaaacatatt ctcaataaac    6960
cctttaggga ataggccag gttttcaccg taacacgcca catcttgcga atatatgtgt    7020
agaaactgcc ggaaatcgtc gtggtattca ctccagagcg atgaaaacgt ttcagtttgc    7080
tcatggaaaa cggtgtaaca agggtgaaca ctatcccata tcaccagctc accgtctttc    7140
```

```
attgccatac g                                                    7151
```

<210> SEQ ID NO 14
<211> LENGTH: 955
<212> TYPE: DNA
<213> ORGANISM: Armoracia rusticana
<220> FEATURE:
<221> NAME/KEY: misc_feature
<223> OTHER INFORMATION: A.rusticana synthetic gene for peroxidase

<400> SEQUENCE: 14

```
aagcttaacc atgcagttaa cccctacatt ctacgacaat agctgtccca acgtgtccaa    60
catcgttcgc gacacaatcg tcaacgagct cagatccgat cccaggatcg ctgcttcaat   120
attacgtctg cacttccatg actgcttcgt gaatggttgc gacgctagca tattactgga   180
caacaccacc agtttccgca ctgaaaagga tgcattcggg aacgctaaca gcgccagggg   240
cttttccagtg atcgatcgca tgaaggctgc cgttgagtca gcatgcccac gaacagtcag   300
ttgtgcagac ctgctgacta tagctgcgca acagagcgtg actcttgcag gcggaccgtc   360
ctggagagtg ccgctcggtc gacgtgactc cctacaggca ttcctagatc tggccaacgc   420
caacttgcct gctccattct caccctgccc cagctgaag gatagcttta gaaacgtggg   480
tctgaatcgc tcgagtgacc ttgtggctct gtccggagga cacacatttg gaaagaacca   540
gtgtaggttc atcatggata ggctctacaa tttcagcaac actgggttac ctgaccccac   600
gctgaacact acgtatctcc agacactgag aggcttgtgc ccactgaatg caacctcag   660
tgcactagtg gactttgatc tgcggacccc aaccatcttc gataacaagt actatgtgaa   720
tctagaggag cagaaaggcc tgatacagag tgatcaagaa ctgtttagca gtccaaacgc   780
cactgacacc atcccactgg tgagaagttt tgctaactct actcaaacct tctttaacgc   840
cttcgtggaa gccatggacc gtatgggtaa cattacccct ctgacgggta cccaaggcca   900
gattcgtctg aactgcagag tggtcaacag caactcttaa taaggatccg aattc        955
```

<210> SEQ ID NO 15
<211> LENGTH: 861
<212> TYPE: DNA
<213> ORGANISM: Artificial Sequence
<220> FEATURE:
<223> OTHER INFORMATION: Synthetic construct SP-1A2 recombinant single
      chain Fv antibody mRNA, partial cds.
<220> FEATURE:
<221> NAME/KEY: misc_feature
<222> LOCATION: (790)..(807)
<223> OTHER INFORMATION: Histidine tag

<400> SEQUENCE: 15

```
cagtctgtgt tgacgcagcc gccctcagtg tctgggtctc ctggacagtc gatcaccatc    60
tcctgcactg gaaccagcag tgatattggg acttataaaa ttgtctcctg gtaccaacag   120
caccctggca agccccccaa actcatgatt tatgacgtca atcagcggcc ctcaggggtt   180
tctgatcgct tctctggctc caagtctggc aacacggcct ccctgacaat ctctgggctc   240
caggctgagg acgaggctga ttattactgc agctcatata caagcggcag cactctggta   300
ttcggcgggg ggaccaagct gaccgtccta ggctcgagtg gtgaggcgg ttcaggcgga   360
ggtggctctg gcggtagtgc acttcaggta cagctgcagc agtcaggagc agaggtgaaa   420
aagcccgggg agtctctgaa gatcctgtgt aagggttctg gatacagctt taccagctac   480
tggatcggct gggtgcgcca gatgcccggg aaagcctgg agtggatggg gatcatctat   540
cctggtgact ctgataccag atacagcccg tccttccaag gccaggtcac catctcagcc   600
```

```
gacaagtcca tcagcaccgc ctacctgcag tggagcagcc tgaaggcctc ggacaccgcc    660
atgtattact gtgcgagaca tcgggccgct agtgggagcc cggacgcgtg tgactactgg    720
ggccagggaa ccctggtcac cgtctcctca gggagtgcat ccgccccaac ccttttcccc    780
gcggccgcac atcatcatca ccatcacggg gccgcagaac aaaaactcat ctcagaagag    840
gatctgaatg gggccgcata g                                              861
```

<210> SEQ ID NO 16
<211> LENGTH: 861
<212> TYPE: DNA
<213> ORGANISM: Artificial Sequence
<220> FEATURE:
<223> OTHER INFORMATION: Synthetic construct SP-1A2 recombinant single
      chain Fv antibody mRNA, partial cds.
<220> FEATURE:
<221> NAME/KEY: misc_feature
<222> LOCATION: (817)..(849)
<223> OTHER INFORMATION: Myc tag

<400> SEQUENCE: 16

```
cagtctgtgt tgacgcagcc gccctcagtg tctgggtctc ctggacagtc gatcaccatc     60
tcctgcactg gaaccagcag tgatattggg acttataaaa ttgtctcctg gtaccaacag    120
caccctggca agcccccaa actcatgatt tatgacgtca atcagcggcc ctcaggggtt     180
tctgatcgct tctctggctc caagtctggc aacacggcct ccctgacaat ctctgggctc    240
caggctgagg acgaggctga ttattactgc agctcatata caagcggcag cactctggta    300
ttcggcgggg gaccaagctg accgtcctag gctcgagtg gtgaggcgg ttcaggcgga     360 ggtggctctg gcggtagtgc acttcaggta cagctgcagc agtcaggagc agaggtgaaa    420
aagcccgggg agtctctgaa gatctcctgt aagggttctg gatacagctt taccagctac    480
tggatcggct gggtgcgcca gatgcccggg aaaggcctgg agtggatggg gatcatctat    540
cctggtgact ctgataccag atacagcccg tccttccaag gccaggtcac catctcagcc    600
gacaagtcca tcagcaccgc ctacctgcag tggagcagcc tgaaggcctc ggacaccgcc    660
atgtattact gtgcgagaca tcgggccgct agtgggagcc cggacgcgtg tgactactgg    720
ggccagggaa ccctggtcac cgtctcctca gggagtgcat ccgccccaac ccttttcccc    780
gcggccgcac atcatcatca ccatcacggg gccgcagaac aaaaactcat ctcagaagag    840
gatctgaatg gggccgcata g                                              861
```

<210> SEQ ID NO 17
<211> LENGTH: 717
<212> TYPE: DNA
<213> ORGANISM: Aequorea macrodactyla

<400> SEQUENCE: 17

```
atgagtaaag gagaagaact tttcactgga gttgtcccaa ttcttgttga attagatggt     60
gatgtccatg gacataaatt ctctgtcaga ggagaagggg aaggcgatgc agattatgga    120
aaacttgaaa tcaaattcat ttgcactact ggaaagctac cagttccatg ccaacacttt    180
gttactacac tgggctatgg catcctatgt ttcgcaagat acccagaaca catgaaaatg    240
aatgacttct tcaagagtgc catgcctgag ggttacattc aagaagaac catctttttc    300 caagatgatg gaaaatacaa gacacgtggt gaagtcaagt ttgaaggtga tactcttgtt    360
aacagaattg agctcaaagg tatggacttt aagaagatg gcaatatcct ggacacaag    420 ttggagtaca attttaactc acataatgta tacattatgc cggacaaagc caataatgga    480
```

```
ctcaaagtca atttcaaaat tagacacaat atcgaaggtg gtggtgtcca actcgctgat    540
cattaccaaa caaatgttcc ccttggagac ggtcctgtcc ttataccaat caatcactac    600
ctatcctatc aaacagccat ttcaaaagat cgaaatgaga cgagagatca tatggtgttt    660
ctggaatttt tctcagcttg tggacataca catggcatgg atgaactata caaataa      717
```

<210> SEQ ID NO 18
<211> LENGTH: 8388
<212> TYPE: DNA
<213> ORGANISM: Artificial Sequence
<220> FEATURE:
<223> OTHER INFORMATION: Vector pFRT1-lacZ-Tel
<400> SEQUENCE: 18

```
acgttaaggg attttggtca tggacggcca gcaggtaggc cgacaggctc atgccggccg     60
ccgccgcctt ttcctcaatc gctcttcgtt cgtctggaag gcagtacacc ttgataggtg    120
ggctgccctt cctggttggc ttggtttcat cagccatccg cttgccctca tctgttacgc    180
cggcggtagc cggccagcct cgcagagcag gattcccgtt gagcaccgcc aggtgcgaat    240
aagggacagt gaagaaggaa cacccgctcg cgggtgggcc tacttcacct atcctgcccg    300
gctgacgccg ttggatacac caaggaaagt ctacacgaac cctttggcaa aatcctgtat    360
atcgtgcgaa aaaggatgga tataccgaaa aaatcgctat aatgacccg aagcagggtt     420 atgcagcgga aaagcgctgc ttccctgctg ttttgtggaa tatctaccga ctggaaacag    480
gcaaatgcag gaaattactg aactgagggg acaggcgaga gacgatgcca agagctaca    540 ccgacgagct ggccgagtgg gttgaatccc gcgcggccaa gaagcgccgg cgtgatgagg    600
ctgcggttgc gttcctggcg gtgagggcgg atgtcgatat gcgtaaggag aaaataccgc    660
atcaggcgca tatttgaatg tatttagaaa aataaacaaa aagagtttgt agaaacgcaa    720
aaaggccatc cgtcaggatg gccttctgct taatttgatg cctggcagtt tatggcgggc    780
gtcctgcccg ccaccctccg gccgttgct tcgcaacgtt caaatccgct cccggcggat     840
ttgtcctact caggagagcg ttcaccgaca acaacagat aaaacgaaag gcccagtctt     900
tcgactgagc ctttcgtttt atttgatgcc tggcagttcc ctactctcgc atggggagac    960
cccacactac catcggcgct acggcgtttc acttctgagt tcggcatggg gtcaggtggg   1020
accaccgcgc tactgccgcc aggcaaattc tgttttatca gaccgcttct gcgttctgat   1080
ttaatctgta tcaggctgaa aattaaggaa tcccccagga cccaacgctg cccgagtttg   1140
tcagaaagca gaccaaacag cggttggaat aatagcgaga acagagaaat gcggcaaaa    1200 ataatacccg tatcactttt gctgatatgg ttgatgtcat gtagccaaat cgggaaaaac   1260
gggaagtagg ctcccatgat aaaaaagtaa aagaaaaaga ataaaccgaa catccaaaag   1320
tttgtgtttt ttaaatagta cataatggat ttccttacgc gaaatacggg cagacatggc   1380
ctgcccggtt attattattt ttgacaccag accaactggt aatggtagcg accggcgctc   1440
agctggaaat ccgccgatac tgacgggctc caggagtcgt cgccaccaat ccccatatgg   1500
aaaccgtcga tattcagcca tgtgccttct tccgcgtgca gcagatggcg atggctggtt   1560
tccatcagtt gctgttgact gtagcggctg atgttgaact ggaagtcgcc gcgccactgg   1620
tgtgggccat aattcaattc gcgcgtcccg cagcgcagac cgttttcgct cgggaagacg   1680 tacgggtat acatgtctga caatggcaga tcccagcggt caaaacaggc ggcagtaagg   1740
cggtcgggat agttttcttg cggccctaat ccgagccagt ttacccgctc tgctacctgc   1800
```

```
gccagctggc agttcaggcc aatccgcgcc ggatgcggtg tatcgctcgc cacttcaaca    1860
tcaacggtaa tcgccatttg accactacca tcaatccggt aggttttccg gctgataaat    1920
aaggttttcc cctgatgctg ccacgcgtga gcggtcgtaa tcagcaccgc atcagcaagt    1980
gtatctgccg tgcactgcaa caacgctgct tcggcctggt aatggcccgc cgccttccag    2040
cgttcgaccc aggcgttagg gtcaatgcgg gtcgcttcac ttacgccaat gtcgttatcc    2100
agcggtgcac gggtgaactg atcgcgcagc ggcgtcagca gttgtttttt atcgccaatc    2160
cacatctgtg aaagaaagcc tgactggcgg ttaaattgcc aacgcttatt acccagctcg    2220
atgcaaaaat ccatttcgct ggtggtcaga tgcgggatgg cgtgggacgc ggcggggagc    2280
gtcacactga ggttttccgc cagacgccac tgctgccagg cgctgatgtg cccggcttct    2340
gaccatgcgg tcgcgttcgg ttgcactacg cgtactgtga gccagagttg cccggcgctc    2400
tccggctgcg gtagttcagg cagttcaatc aactgtttac cttgtggagc gacatccaga    2460
ggcacttcac cgcttgccag cggcttacca tccagcgcca ccatccagtg caggagctcg    2520
ttatcgctat gacggaacag gtattcgctg gtcacttcga tggtttgccc ggataaacgg    2580
aactggaaaa actgctgctg gtgttttgct tccgtcagcg ctggatgcgg cgtgcggtcg    2640
gcaaagacca gaccgttcat acagaactgg cgatcgttcg gcgtatcgcc aaaatcaccg    2700
ccgtaagccg accacgggtt gccgttttca tcatatttaa tcagcgactg atccacccag    2760
tcccagacga agccgccctg taaacgggga tactgacgaa acgcctgcca gtatttagcg    2820
aaaccgccaa gactgttacc catcgcgtgg gcgtattcgc aaaggatcag cgggcgcgtc    2880
tctccaggta gcgaaagcca ttttttgatg gaccatttcg gcacagccgg gaagggctgg    2940
tcttcatcca cgcgcgcgta catcgggcaa ataatatcgg tggccgtggt gtcggctccg    3000
ccgccttcat actgcaccgg gcgggaagga tcgacagatt tgatccagcg atacagcgcg    3060
tcgtgattag cgccgtggcc tgattcattc cccagcgacc agatgatcac actcgggtga    3120
ttacgatcgc gctgcaccat tcgcgttacg cgttcgctca tcgccggtag ccagcgcgga    3180
tcatcggtca gacgattcat tggcaccatg ccgtgggttt caatattggc ttcatccacc    3240
acatacaggc cgtagcggtc gcacagcgtg taccacagcg gatggttcgg ataatgcgaa    3300
cagcgcacgg cgttaaagtt gttctgcttc atcagcagga tatcctgcac catcgtctgc    3360
tcatccatga cctgaccatg cagaggatga tgctcgtgac ggttaacgcc tcgaatcagc    3420
aacggcttgc cgttcagcag cagcagacca ttttcaatcc gcacctcgcg gaaaccgaca    3480
tcgcaggctt ctgcttcaat cagcgtgccg tcggcggtgt gcagttcaac caccgcacga    3540
tagagattcg ggatttcggc gctccacagt ttcgggtttt cgacgttcag acgtagtgtg    3600
acgcgatcgg cataaccacc acgctcatcg ataatttcac cgccgaaagg cgcggtgccg    3660
ctggcgacct gcgtttcacc ctgccataaa gaaactgtta cccgtaggta gtcacgcaac    3720
tcgccgcaca tctgaacttc agcctccagt acagcgcggc tgaaatcatc attaaagcga    3780
gtggcaacat ggaaatcgct gatttgtgta gtcggtttat gcagcaacga gacgtcacgg    3840
aaaatgccgc tcatccgcca catatcctga tcttccagat aactgccgtc actccaacgc    3900
agcaccatca ccgcgaggcg gttttctccg gcgcgtaaaa atgcgctcag gtcaaattca    3960
gacggcaaac gactgtcctg gccgtaaccg acccagcgcc cgttgcacca cagatgaaac    4020
gccgagttaa cgccatcaaa aataattcgc gtctggcctt cctgtagcca gctttcatca    4080
acattaaatg tgagcgagta acaacccgtc ggattctccg tgggaacaaa cggcggattg    4140
accgtaatgg gataggttac gttggtgtag atgggcgcat cgtaaccgtg catctgccag    4200
```

```
tttgagggga cgacgacagt atcggcctca ggaagatcgc actccagcca gctttccggc    4260
accgcttctg gtgccggaaa ccaggcaaag cgccattcgc cattcaggct gcgcaactgt    4320
tgggaagggc gatcggtgcg ggcctcttcg ctattacgcc agctggcgaa aggggatgt     4380
gctgcaaggc gattaagttg ggtaacgcca gggttttccc agtcacgacg ttgtaaaacg    4440
acgggatcag ccatttttt ctccttactt acttaggatc cccgggtacc gagctcgaat     4500
tggggatctt gaagttccta ttccgaagtt cctattctct agaaagtata ggaacttcag    4560
agcgcttttg aagctaattc gagctcggta cccggggatc ccccgggctc gactgcatta    4620
atgaatcggc caacgcgcgg ggagaggcgg tttgcgtatt gggcgctctt ccgctcgaat    4680
tgacataagc ctgttcggtt cgtaaactgt aatgcaagta gcgtatgcgc tcacgcaact    4740
ggtccagaac cttgaccgaa cgcagcgtg gtaacggcgc agtggcggtt ttcatggctt     4800
gttatgactg ttttttttgta ctcgagcaga aagtcaaaag cctccgaccg gaggcttttg   4860
acttgagggg gatcgatccc ttatggctct gcacccggct ccatcaccaa caggtcgcgc    4920
acgcgcttca ctcggttgcg gatcgacact gccagcccaa caaagccggt tgccgccgcc    4980
gccaggatcg cgccgatgat gccggccaca ccggccatcg cccaccaggt cgccgccttc    5040
cggttccatt cctgctggta ctgcttcgca atgctggacc tcggctcacc ataggctgac    5100
cgctcgatgg cgtatgccgc ttctccccatt ggcgtaaaac ccagcgccgc aggcggcatt   5160
gccatgctgc ccgccgcttt cccgaccacg acgcgcgcac caggcttgcg gtccagacct    5220
tcggccacgg cgagctgcgc aaggacataa tcagccgccg acttggctcc acgcgcctcg    5280
atcagctctt gcactcgcgc gaaatccttg gcctccacgg ccgccatgaa tcgcgcacgc    5340
ggcgaaggct ccgcagggcc ggcgtcgtga tcgccgccga gaatgccctt caccaagttc    5400
gacgacacga aaatcatgct gacggctatc accatcatgc agacggatcg cacgaacccg    5460
cagaactcac ccccgaacac gagcacggca cccgcgacca ctatgccaag aatgcccaag    5520
gtaaaaattg ccggccccgc catgaagtcc gtgaatgccc cgacggccga agtgaagggc    5580
aggccgccac ccaggccgcc gccctcactg cccggcacct ggtcgctgaa tgtcgatgcc    5640
agcacctgcg gcacgtcaat gcttccgggc gtcgcgctcg ggctgatcgc ccatcccgtt    5700
actgccccga tcccgcaat ggcaaggact gccagcgccg cgatgaggaa gcgggtgccc     5760
cgcttcttca tcttcgcgcc tcgggcctcc aggccgccta cctgggcgaa acatcggtg     5820
tttgtggcat tcatacggac tcctgttggg ccagctcgcg cacgggctgg cgggtcagct    5880
tggcttgaag atcgccacgc attgcggcga tctgcttctc ggcatccttg cgcttctgca    5940
cgccttcctg ctggatgcga ataacgtcct cgacggtctt gatgagcgtc gtctgaacct    6000
gcttgagcgt gtccacgtcg atcaccaggc gttggttctc cttcgccgtc tcgacggacg    6060
tgcgatgcag cagggccgca ttgcgcttca tcaggtcgtt ggtggtgtcg tcgatggccg    6120
tggccagttc gacggcgttc ttctgctcgt tgaggctcaa ggccagcatg aattgccgct    6180
tccacgccgg cacggtgatt tcgcggatgg tgtggaattt atcgaccagc atctggttgt    6240
tggcctggat catgcggatg gtcggcaggc tctgcatggc cgaatgttgc aaggcgatca    6300
ggtcgccgat gcgcttgtcc aggttggcaa ccatcgcatc gaggtcggcc agctcctgca    6360
cgcggccagg gtcgttcccg acattgccgc gcagaccctc ggcctgctcg cgcagctcgg    6420
caaggcggac cttgccggcc gcgatgtgga cgccaagaag gcggtgttcc tcgcacggg    6480
ctgcgaacat ttcgtcgagc gaggcattgc gctgcgcgat gccttgctgg gtggtctgca    6540
```

```
cttcgctgac caggtgttcg atctgctcgc gggtcgtgtc gaagcgcgcc atgaagcccg    6600
tcgaacggac gcggaagcgg tcgatcagcg ggccaatcag gggcaggcgg aacggttgt    6660 cggacaaagg gccgacgttc agggaacggg ccttggcgac aacctgggtc agtttctcgc    6720
ctgcttcgtc caggtcgctg ttgcgcacct ggtccagcag gctatcggcg tagcgggacg    6780
tgtgctcggc cacgtcgcgg ccgaactcgg caacggtctg cggactgccg acctcgatcc    6840
gctgcgcgac cgcatggact tccggcacgt cgctttcctg caagcccagc tcgcgcaggg    6900
ttgccggggt catgtcgaag gcgacgatag gggccttggc gtcgtgcgtc gttttcagtg    6960
cgttcatagg gttctcccgc cgtgttattg gttgatgcct tccaggctct gcgaaaggct    7020
ccgcatgagc gcctggtgag ctttggccgc ctcggcgacc attgccggat tcatgttctt    7080
ggtggtgatg agcgcgaggg tgtgctgacg ccagacgggc accaggacgg atgccgtttc    7140
agagaagcgg tccagcatgt ccacggcctg cgcccgcgtg agcttcatct gagtgacgct    7200
catttcatgg gacgccatga gggttgccag gttggcgagc ttgcgcgcga agcgttcgcg    7260
cggcttgtcg aactcgatca cgccggcctt ggccgcgccg gcctcggggt tctcgtccag    7320
gaactcgcgc ccggcttgaa tgtaggctct gagccggtct acctcggcct catgcgtatt    7380
gagcatgtca tccaaggcgc gcaacgtgtc ccgcacgcgc tgcgctacgc cctcggcttc    7440
gtccagcaac tggtcgagcg tcttgcgggc gacctgatac ctcacctggc gttcaacctc    7500
acggccaagc atcttctcga accaggtagg ctttccgcg atcttgcggg ggtccgcgtc    7560
ggccagcttc gccacgatct ggctgatttt gtcggccagc gcggcaactg cgccgtgctc    7620
catcagattc gacagctcgt tgagggaatc cgccccgtcg atgccggccc cgtactcgcc    7680
aatcgtcgcc ggcgacgcga gagggcggg caaaacctcc cccttcaatc gcgccatgtt    7740
cacgctttgt tcttccatgg tatatctcct tcttaaagtt aaacaaaatt attcggaacc    7800
cagcatgata ttccggaaat accaactaag tcaacggctg atggccaatt cggcttcctc    7860
gctcactgac tcgctgcgct cggtcgttcg gctgcggcga gcggtatcag ctcactcaaa    7920
ggcggtaata cggttatcca cagaatcagg ggataacgca ggaaagaaca tgtgagatcg    7980
atcagcagtt caacctgttg atagtacgta ctaagctctc atgtttcacg tactaagctc    8040
tcatgtttaa cgtactaagc tctcatgttt aacgaactaa accctcatgg ctaacgtact    8100
aagctctcat ggctaacgta ctaagctctc atgtttcacg tactaagctc tcatgtttga    8160
acaataaaat taatataaat cagcaactta atagcctct aaggttttaa gttttataag    8220
aaaaaaaaga atatataagg cttttaaagc tagcttttaa ggtttaacgg ttgtggacaa    8280
caagccaggg atgtaacgca ctgagaagcc cttagagcct ctcaaagcaa ttttcagtga    8340
cacaggaaca cttaacggct gacatgacgc tcagtggaac gaaaactc                8388
```

<210> SEQ ID NO 19  
<211> LENGTH: 483  
<212> TYPE: DNA  
<213> ORGANISM: Artificial Sequence  
<220> FEATURE:  
<223> OTHER INFORMATION: Synthetic construct streptavidin gene

<400> SEQUENCE: 19

```
gacccgagca aagattctaa agcacaagta tctgctgcag aagcaggaat tacaggcaca     60
tggtataatc agctgggatc tacatttatt gttacagccg cgcagatgg agctcttaca    120 ggaacatatg aatctgctgt tggaaatgca gaatctagat acgtgcttac aggaagatat    180
gattctgcac ctgcaacaga tggatccgga acagcacttg gatggacagt tgcatggaaa    240
```

```
aacaattata gaaacgcaca tagcgctaca acatggtctg gccaatatgt gggaggtgca    300
gaagcaagaa ttaacacaca atggctttta acatctggaa caacagaagc aaatgcatgg    360
aaaagtactc ttgttggaca tgatacattt acaaaagtta aacctagcgc agcatctatc    420
gatgcagcga aaaaagcagg agttaacaat ggcaatcctt tagatgcagt tcaacaataa    480
tga                                                                  483
```